United States Patent [19]

Dhanoa et al.

[11] Patent Number: 5,420,133

[45] Date of Patent: May 30, 1995

[54] QUINAZOLINONES SUBSTITUTED WITH PHENOXYPHENYLACETIC ACID DERIVATIVES

[75] Inventors: Daljit S. Dhanoa, Secaucus; Kenneth J. Fitch, Cranford, both of N.J.; Daniel F. Veber, Ambler, Pa.; Thomas F. Walsh, Watchung, N.J.; David L. Williams, Jr., Telford, Pa.

[73] Assignee: Merck & Co., Inc., Rahway, N.J.

[21] Appl. No.: 34,448

[22] Filed: Mar. 19, 1993

[51] Int. Cl.$^6$ .............. A61K 31/41; A01N 43/64; C07D 413/00; C07D 413/14

[52] U.S. Cl. .............. 514/256; 514/229.5; 514/230.5; 514/247; 514/258; 514/269; 514/826; 514/893; 544/242; 544/245; 544/253; 544/283; 544/295; 544/298; 544/299; 544/300; 544/301; 544/302; 544/304; 544/305; 544/309; 544/310; 544/311; 548/100; 548/124; 548/146; 548/181; 548/182; 548/184; 548/190

[58] Field of Search .............. 514/256, 229.5, 230.5, 514/247, 258, 269, 826, 893; 544/242, 253, 298, 299, 300, 301; 548/181

[56] References Cited

U.S. PATENT DOCUMENTS

| | | | |
|---|---|---|---|
| 4,166,851 | 9/1979 | Baldwin et al. | 44/248.55 |
| 4,543,356 | 9/1985 | Ueda et al. | 514/259 |
| 4,599,336 | 7/1986 | Carson et al. | 514/259 |
| 4,761,416 | 8/1988 | Fried et al. | 514/260 |
| 4,886,801 | 12/1989 | Grozinger et al. | 514/247 |
| 5,008,266 | 4/1991 | Takahashi et al. | 514/259 |
| 5,082,838 | 1/1992 | Naka et al. | 514/211 |
| 5,114,918 | 5/1992 | Ishikawa et al. | 514/11 |
| 5,177,095 | 1/1993 | Greenlee et al. | 514/384 |
| 5,183,810 | 2/1993 | Greenlee et al. | 514/63 |
| 5,187,195 | 2/1993 | Oohata et al. | 514/510 |

FOREIGN PATENT DOCUMENTS

| | | |
|---|---|---|
| 0436189A1 | 7/1990 | European Pat. Off. |
| 0457195A2 | 11/1991 | European Pat. Off. |
| 0460679A2 | 12/1991 | European Pat. Off. |
| 0496452A1 | 7/1992 | European Pat. Off. |
| 0510526A1 | 10/1992 | European Pat. Off. |
| 0526642A1 | 2/1993 | European Pat. Off. |
| 0526708A1 | 2/1993 | European Pat. Off. |
| 2259450 | 3/1993 | United Kingdom |
| WO91/12001 | 8/1991 | WIPO |
| WO92/20706 | 11/1992 | WIPO |
| WO92/15321 | 9/1993 | WIPO |

OTHER PUBLICATIONS

J. of Pharmacology & Experimental Therapeutics, vol. 270, No. 1, pp. 228–235 (1994), by M. Clozel, et al.
J. of Cardiovascular Pharmacology, vol. 22 (Suppl.8), pp. S377–S379 (1993), by M. Clozel, et al.
Proc. Natl. Acad. Sci. USA, vol. 91, pp. 8052–8056 (Aug. 1994) Pharmacology, by E. H. Ohlstein, et al.

(List continued on next page.)

*Primary Examiner*—Arthur C. Prescott
*Attorney, Agent, or Firm*—Valerie J. Camara; Mark R. Daniel; Joseph F. DiPrima

[57] ABSTRACT

Phenoxyphenylacetic acids and derivatives of general structural formula I

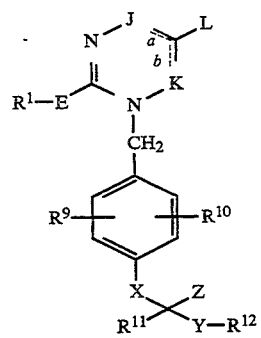

have endothelin antagonist activity and are therefore useful in treating cardiovascular disorders, such as hypertension, postischemic renal failure, vasospasm, cerebral and cardiac ischemia, myocardial infarction, inflammatory diseases, Raynaud's disease, and endotoxic shock, and asthma.

14 Claims, No Drawings

OTHER PUBLICATIONS

Nature, vol. 365, pp. 759–761 (21 Oct. 1993), by M. Clozel, et al.

1993 Federation of European Biochemical Societies, vol. 334, No. 2, pp. 210–214 (Nov. 1993), by V. Breu, et al.

U.S. patent application Ser. No. 8/033,595 filed Mar. 1993 by Bagley et al.

U.S. patent application Ser. No. 8/035,340 filed Mar. 3, 1993 by Bagley et al.

U.S. patent application Ser. No. 8/034,456 filed Mar. 1993 by Dhanoa et al.

U.S. patent application Ser. No. 8/029,745 filed Mar. 1993 by Bills et al.

U.S. patent application Ser. No. 08/034,455 filed Mar. 1993 by Bagley et al.

U.S. patent application Ser. No. 07/744,138 filed Aug. 1991 by Greenlee et al.

QUINAZOLINONES SUBSTITUTED WITH PHENOXYPHENYLACETIC ACID DERIVATIVES

SUMMARY OF THE INVENTION

This invention is concerned with non-peptidic endothelin receptor antagonists and their method of use. The compounds of the present invention are therapeutic agents particularly useful for the treatment of asthma, hypertension, pulmonary hypertension, arteriosclerosis, congestive heart failure, renal failure, particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin.

BACKGROUND OF THE INVENTION

Endothelin is a 21-amino acid peptide produced by endothelial cells. The peptide is secreted not only by endothelial cells but also by tracheal epithelial cells or from kidney cells. Endothelin (ET-1) has a potent vasoconstrictor effect. The vasoconstricting effect is caused by the binding of endothelin to its receptor on the vascular smooth muscle cells.[1-3]

Endothelin-1 (ET-1) is one of three recently identified potent vasoconstricting peptides which also includes endothelin-2 (ET-2) and endothelin-3 (ET-3) which differ from ET-1 by two and six amino acids, respectively.[4]

Increased levels of endothelin are found in the blood of patients with essential hypertension, acute myocardial infarction, pulmonary hypertension, Raynaud's disease or atherosclerosis or in the washing fluids of the respiratory tract of patients with asthma compared to normal levels.[5-8]

An experimental model of cerebral vasospasm and a second model of acute renal failure have led to the conclusion that endothelin is one of the mediators causing cerebral vasospasm following a subarachnoid hemorrhage, and renal failure.[9-10]

Endothelin was also found to control the release of many physiological substances such as renin, atrial natriuretic peptide, endothelium-derived relaxing factor (EDRF), thromboxane $A_2$,[14] prostacyclin, norepinephrine, angiotensin II and substance P.[11-16] Further, endothelin causes contraction of the smooth muscle of the gastrointestinal tract and the uterine smooth muscle.[17-19] Endothelin has also been shown to promote the growth of rat vascular smooth muscle cells which would suggest a possible relevance to arterial hypertrophy.[20]

Endothelin receptors are present in high concentration in the peripheral tissues and also in the central nervous system, and cerebral administration of endothelin has been shown to induce behavioral changes in animals, suggesting that endothelin may play an important role in controlling neural functions.[21]

Endotoxin has been shown to promote the release of endothelin. This finding has suggested that endothelin is an important mediator for endotoxin-induced diseases.[22-23]

A study has shown that cyclosporin added to a renal cell culture, increased endothelin secretion.[24] Another study has shown that administration of cyclosporin to rats led to a decrease in the glomerular filtration rate and an increase in the blood pressure, in association with a remarkable increase in the circulating endothelin level. This cyclosporin-induced renal failure can be suppressed by the administration of anti-endothelin antibody.[25] These studies suggest that endothelin is significantly involved in the pathogenesis of cyclosporin-induced renal disease.

A recent study in patients with congestive heart failure demonstrated a good correlation between the elevated levels of endothelin in the plasma and the severity of the disease.[26]

Substances which specifically inhibit the binding of endothelin to its receptor are believed to block the physiological effects of endothelin and would be useful in treating patients with endothelin related disorders. The present invention discloses potent non-peptidic endothelin antagonists.

Endothelin is an endogenous substance which directly or indirectly (through the controlled release of various other endogenous substances) induces sustained contraction of vascular or non-vascular smooth muscles. Its excess production or excess secretion is believed to be one of the factors responsible for hypertension, pulmonary hypertension, Raynaud's disease, bronchial asthma, acute renal failure, myocardial infarction, angina pectoris, arteriosclerosis, cerebral vasospasm and cerebral infarction.

The novel compounds of the present invention are useful as non-peptidic endothelin antagonists, and have not been disclosed in any issued patents or patent applications. Fujisawa in European Patent Application EP 457,195, Banyu in EP 436,189 and 460,679, and Takeda in Patent Cooperation Treaty International Publication No. WO 91/13089 have applications disclosing linear and cyclic peptidic compounds as endothelin antagonists. Fujisawa has also disclosed anthraquinone derivatives produced by a fermentation process using Streptomyces sp. No. 89009 in EP 405,421.

A Roussel-Uclaf European Patent Application (EP 498,723) disclosed a series of substituted (1,4-quinolinoxy)methylbiphenylcarboxylic acids as both endothelin antagonists and angiotensin II antagonists. A patent from Hoffmann-La Roche (EP 510,526) has also appeared claiming the endothelin antagonist properties of a series of N-(4-pyrimidinyl)benzenesulfonamides.

REFERENCES

1 Nature, 332, 411–415 (1988).
2 FEBS Letters, 231, 440–444 (1988).
3 Biochem. Biophys. Res. Commun. 154, 868–875 (1988).
4 TiPS, 13, 103–108, March 1992.
5 Japan J. Hypertension 12, 79 (1989).
6 J. Vascular Medicine Biology, 2, 207 (1990).
7 J. Am. Med. Association, 264, 2868 (1990).
8 The Lancet, ii, 207 (1990) and The Lancet, ii, 747–748 (1989).
9 Japan. Soc. Cereb. Blood Flow & Metabol. 1, 73 (1989).
10 J. Clin. Invest., 83, 1762–1767 (1989).
11 Biochem. Biophys. Res. Comm. 157, 1164–1168 (1988).
12 Biochem. Biophys. Res. Comm. 155, 167–172 (1989).
13 Proc. Natl. Acad. Sci. USA, 85, 9797–9800 (1989).
14 J. Cardiovasc. Pharmacol., 13, 589–592 (1989).
15 Japan. J. Hypertension 12, 76 (1989).
16 Neuroscience Letters, 102, 179–184 (1989).
17 FEBS Letters, 247, 337–340 (1989).
18 Eur. J. Pharmacol. 154, 227–228 (1988).

19 Biochem. Biophys. Res. Commun., 159, 317–323 (1989).
20 Atherosclerosis, 78, 225–228 (1989).
21 Neuroscience Letters, 97, 276–279 (1989).
22 Biochem. Biophys. Res. Commun. 161, 1220–1227 (1989).
23 Acta. Physiol. Scand., 137, 317–318 (1989).
24 Eur. J. Pharmacol., 180, 191–192 (1990).
25 Kidney Int. 37, 1487–1491 (1990).
26 Mayo Clinic Proc., 67, 719–724 (1992).

DETAILED DESCRIPTION OF THE INVENTION

This invention relates to compounds of the general Formula I useful in this novel method of treatment:

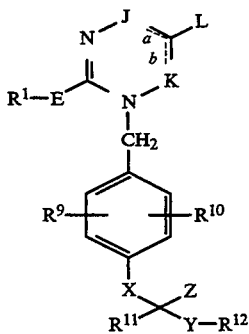

I or a pharmaceutically acceptable salt thereof, wherein:

$R^1$ is:
(a) $(C_1-C_6)$-alkyl, $(C_2-C_6)$-alkenyl or $(C_2-C_6)$-alkynyl each of which is unsubstituted or substituted with a substituent selected from the group consisting of:
  i) aryl as defined below,
  ii) $(C_3-C_7)$-cycloalkyl,
  iii) Cl, Br, I, F,
  iv) OH,
  v) $NH_2$,
  vi) $NH(C_1-C_4)$-alkyl,
  vii) $N[(C_1-C_4)\text{-alkyl}]_2$,
  viii) $NHSO_2R^2$,
  ix) $CF_3$,
  x) $COOR^2$, or
  xi) $SO_2NHR^{2a}$; and
(b) aryl, wherein aryl is defined as phenyl or naphthyl unsubstituted or substituted with 1 or 2 substituents selected from the group consisting of:
  i) Br, I, Cl, F,
  ii) $(C_1-C_4)$-alkyl,
  iii) $(C_1-C_4)$-alkoxy,
  iv) $NO_2$
  v) $CF_3$
  vi) $SO_2NR^{2a}R^{2a}$,
  vii) $(C_1-C_4)$-alkylthio,
  viii) hydroxy,
  ix) amino,
  x) $(C_3-C_7)$-cycloalkyl,
  xi) $(C_3-C_{10})$-alkenyl; and
(c) heteroaryl, wherein heteroaryl is defined as an unsubstituted, monosubstituted or disubstituted heteroaromatic 5- or 6-membered cyclic moiety, which can contain one or two members selected from the group consisting of N, O, S and wherein the substituents are members selected from the group consisting of:
  i) Cl, Br, I, or F,
  ii) OH,
  iii) SH,
  iv) $NO_2$,
  v) $(C_1-C_4)$-alkyl,
  vi) $(C_2-C_4)$-alkenyl,
  vii) $(C_2-C_4)$-alkynyl,
  viii) $(C_1-C_4)$-alkoxy, or
  ix) $CF_3$, or
(d) $(C_1-C_4)$-perfluoroalkyl; and E is:
(a) a single bond,
(b) $-S(O)_n(CH_2)_s-$, or
(c) $-O-$; and
n is: 0 to 2; and
s is: 0 to 5; and
J is: (a) $-C(=M)-$, (b) J and L are connected together to form a 6-membered aromatic ring substituted with $R^{7a}$, $R^{7b}$, $R^{8a}$ and $R^{8b}$ or (c) J and L are connected together to form a 6-membered aromatic ring containing one nitrogen atom not at $J^1$, substituted with $R^{7a}$, $R^{7b}$, $R^{8a}$ and R8b; and K is: (a) $-C(=M)-$, (b) K and L are connected together to form a 6-membered aromatic ring substituted with $R^{7a}$, $R^{7b}$, $R^{8a}$ and $R^{8b}$, or (c) K and L are connected together to form a 6-membered aromatic ring containing one nitrogen atom, substituted on the carbon atoms with $R^{7a}$, $R^{7b}$ and R8b; and one of a or b is a double bond in Formula I provided that when J is $-C(=M)-$ then b is a double bond and when K is $-C(=M)-$ then a is a double bond.

L is the point of attachment of the 6-membered fused aromatic ring optionally containing one nitrogen atom; and M is: O, S or $NR^{15}$; and
$R^2$ is:
(a) H, or
(b) $(C_1-C_6)$-alkyl; and
$R^{2a}$ is:
(a) $R^2$,
(b) $CH_2$-aryl, or
(c) aryl; and
$R^{7a}$ and $R^{7b}$ are independently:
(a) H,
(b) $(C_1-C_6)$-alkyl, $(C_2-C_6)$-alkenyl or $(C_2-C_6)$-alkynyl,
(c) Cl, Br, I, F,
(d) $CF_3$, or
(e) when $R^{7a}$ and $R^{7b}$ are bonded to adjacent carbon atoms, they can be joined to form a phenyl ring;
$R^{8a}$ and $R^{8b}$ are independently:
(a) H,
(b) aryl-$(C_1-C_4)$-alkyl,
(c) heteroaryl-$(C_1-C_4)$-alkyl,
(d) $(C_1-C_6)$-alkyl, which is unsubstituted or substituted with a substituent selected from the group consisting of: $-CON(R^{2a})_2$, $-$heteroaryl, $-S(O)_n-R^{16}$, $-$tetrazol-5-yl, $-CONHSO_2R^{16}$, $-SO_2NH$-heteroaryl, $-SO_2NHCOR^{16}$, $-PO(OR^2)_2$, $-PO(OR^{2a})_2$, $-SO_2NH-CN$, $-NR^2COOR^{16}$, $-OH$, $-NH_2$, guanidino, $(C_1-C_4)$-alkoxy, $(C_1-C_4)$-alkylthio, $(C_1-C_4)$-alkylamino, $(C_1-C_4)$-dialkylamino, $-COOR^{2a}$, $-CONHR^{2a}$, $-O-COR^{2a}$, or aryl,
(e) $-CO$-aryl,
(f) $(C_3-C_7)$-cycloalkyl, (g) Cl, Br, I, F,
(h) —OH,
(i) —OR$^{16}$,
(j) —SH,
(k) —S(O)$_n$—(C$_1$–C$_4$)-alkyl,
(l) —COR$^{2a}$,
(m) —CO$_2$H,
(n) —CO$_2$—(C$_1$–C$_4$)-alkyl,
(o) —SO$_3$H,
(p) —NR$^2$R$^{16}$,
(q) —NR$^2$COR$^{16}$,
(r) —NR$^2$COOR$^{16}$,
(s) —SO$_2$NHR$^{2a}$,
(t) —SO$_2$NR$^2$R$^{2a}$,
(u) —NO$_2$,
(v) —NHSO$_2$CF$_3$,
(w) —CONR$^{2a}$R$^{2a}$,
(x) —(C$_1$–C$_4$)-perfluoroalkyl,
(y) —COOR$^2$,
(z) —SO$_3$H,
(aa) —N(R$^2$)SO$_2$R$^{16}$,
(bb) —NR$^2$CONR$^4$R$^{16}$,
(cc) —OC(=O)NR$^{16}$R$^{2a}$,
(dd) —aryl,
(ee) —NHSO$_2$CF$_3$,
(ff) —SO$_2$NH-heteroaryl,
(gg) —SO$_2$NHCOR$^{16}$,
(hh) —CONHSO$_2$R$^{16}$,
(ii) —PO(OR$^2$)$_2$,
(jj) —tetrazol-5-yl,
(kk) —CONH(tetrazol-5-yl),
(ll) —SO$_2$NHCN, or
(mm) —heteroaryl; and
R$^9$ and R$^{10}$ are independently:
(a) H,
(b) (C$_1$–C$_6$)-alkyl, unsubstituted or substituted with (C$_3$–C$_7$)-cycloalkyl,
(c) (C$_2$–C$_6$)-alkenyl,
(d) (C$_2$–C$_6$)-alkynyl,
(e) Cl, Br, F, I,
(f) (C$_1$–C$_6$)-alkoxy,
(g) when R$^9$ and R$^{10}$ are on adjacent carbons, they can be joined to form a phenyl ring,
(h) perfluoro-(C$_1$–C$_6$)-alkyl,
(i) (C$_3$–C$_7$)-cycloalkyl, unsubstituted or substituted with (C$_1$–C$_6$)-alkyl,
(j) aryl,
(k) (C$_1$–C$_6$)-alkyl-S(O)$_n$—(CH$_2$)$_n$—,
(l) hydroxy-(C$_1$–C$_6$)-alkyl,
(m) —CF$_3$,
(n) —CO$_2$R$^{2a}$,
(o) —OH,
(p) —NR$^2$R$^{16}$,
(q) —[(C$_1$–C$_6$-alkyl]NR$^2$R$^{16}$,
(r) —NO$_2$,
(s) —(CH$_2$)$_n$—SO$_2$—N(R$^2$)$_2$,
(t) —NR$^2$CO—(C$_1$–C$_4$)-alkyl, or
(u) —CON(R$^2$)$_2$;
X is:
(a) —O—,
(b) —S(O)$_n$—,
(c) —NR$^{13}$—,
(d) —CH$_2$O—,
(e) —CH$_2$S(O)$_n$,
(f) —CH$_2$NR$^{13}$—,
(g) —OCH$_2$—,
(h) —NR$^{13}$CH$_2$—,
(i) —S(O)$_n$CH$_2$—,
(j) single bond, or
Y is:
(a) single bond,
(b) —O—,
(c) —S(O)$_n$—, or
(d) —NR$^{13}$—; and
except that X and Y are not defined in such a way that the carbon atom to which Z is attached also simultaneously is bonded to two heteroatoms (O, N, S, SO, SO$_2$);
R$^{11}$ and R$^{12}$ are independently:
(a) H,
(b) (C$_1$–C$_6$)-alkyl, unsubstituted or substituted with a substituent selected from the group consisting of:
(i) aryl,
(ii) (C$_3$–C$_7$)-cycloalkyl,
(iii) NR$^2$R$^{21}$,
(iv) morpholin-4-yl,
(v) OH,
(vi) CO$_2$R$^{2a}$, or
(vii) CON(R$^2$)$_2$,
(c) aryl or aryl-(C$_1$–C$_2$)-alkyl, unsubstituted or substituted with 1 to 3 substitutents selected from the group consisting of:
(i) Cl, Br, I, F,
(ii) (C$_1$–C$_6$)-alkyl,
(iii) [(C$_1$–C$_5$)-alkenyl]CH$_2$—,
(iv) [(C$_1$–C$_5$)-alkynyl]CH$_2$—,
(v) (C$_1$–C$_6$)-alkyl-S(O)$_n$—(CH$_2$)$_n$—,
(vi) —CF$_3$,
(vii) —CO$_2$R$^{2a}$,
(viii) —OH,
(ix) —NR$^2$R$^{16}$,
(x) —NO$_2$,
(xi) —NR$^2$COR$^2$,
(xii) —CON(R$^2$)$_2$,
(xiii) —G—[(C$_1$–C$_6$)-alkyl]-R$^{18}$,
(xiv) —N[CH$_2$CH$_2$]$_2$Q, or
(xv) —P(O)[O—(C$_1$–C$_4$)-alkyl]$_2$, and can additionally be substituted with 1 or 2 substituents selected from the group consisting of: Br, Cl or F,
(d) (C$_3$–C$_7$)-cycloalkyl, or
(e) when Y is single bond, R$^{11}$ and R$^{12}$ can be joined to form a ring of 5 to 7 carbon atoms, the ring can be benzo-fused and one carbon of which can be replaced with a heteroatom selected from the group consisting of: O, S(O)$_n$ and NR$^{17}$; and
G is: a single bond, O, S(O)$_n$ or NR$^{18}$; and
Q is: O, S(O)$_n$ or NR$^{17}$; and
R$^{13}$ is:
(a) H,
(b) (C$_1$–C$_6$)-alkyl,
(c) aryl,
(d) aryl-(C$_1$–C$_6$)-alkyl-(C=O)—,
(e) (C$_1$–C$_6$)-alkyl-(C=O)—,
(f) [(C$_2$–C$_5$)-alkenyl]CH$_2$—,
(g) [(C$_2$–C$_5$)-alkynyl]CH$_2$—, or
(h) aryl-CH$_2$—; and
Z is:
(a) —CO$_2$H,
(b) —CO$_2$R$^{19}$,
(c) —tetrazol-5-yl,
(d) —CONH(tetrazol-5-yl)
(e) —CONHSO$_2$-aryl, wherein aryl is phenyl or naphthyl, which is unsubstituted or substituted as defined in R$^1$(b),
(f) —CONHSO$_2$—(C$_1$–C$_8$)-alkyl, wherein the alkyl group is unsubstituted or substituted with a substituent selected from the group consisting of: —OH, —SH, —O($C_1$–$C_4$)-alkyl, —S—($C_1$–$C_4$)-alkyl, —$CF_3$, Cl, Br, F, I, —$NO_2$, —$CO_2H$, —$CO_2$—($C_1$–$C_4$)-alkyl, —$NH_2$, —NH[($C_1$–$C_4$)-alkyl], —N[($C_1$–$C_4$)-alkyl]$_2$; and (g) —$CONHSO_2$—($C_1$–$C_4$)-perfluoroalkyl, (h) —$CONHSO_2$-heteroaryl, wherein heteroaryl is unsubstituted or substituted as defined in $R^1$(c), (i) —$CONHSO_2NR^{2a}R^{2a}$; and (j) —$SO_2NHCO$-aryl, wherein aryl is phenyl or naphthyl, which is unsubstituted or substituted as defined in $R^1$(b);

(k) —$SO_2NHCO$-($C_1$–$C_8$)-alkyl, wherein the alkyl group is unsubstituted or substituted with a substituent selected from the group consisting of: —OH, —SH, —O($C_1$–$C_4$)-alkyl, —S—($C_1$–$C_4$)-alkyl, —$CF_3$, Cl, Br, F, I, —$NO_2$, —$CO_2H$, —$CO_2$—($C_1$–$C_4$)-alkyl, —$NH_2$, —NH[($C_1$–$C_4$)-alkyl], —N[($C_1$–$C_4$)-alkyl]$_2$; and (l) —$SO_2NHCO$-($C_1$–$C_4$)-perfluoroalkyl, (m) —$SO_2NHCO$-heteroaryl, wherein heteroaryl is unsubstituted or substituted as defined in $R^1$(c), (n) —$SO_2NHCONR^{2a}R^{2a}$;

(o) —$PO(OH)_2$, (p) —$PO(OR^2)_2$, or (q) —$PO(OH)(OR^2)$; and $R^{14}$ is:
(a) H,
(b) ($C_1$–$C_8$)-alkyl,
(c) ($C_1$–$C_8$)-perfluoroalkyl,
(d) ($C_3$–$C_6$)-cycloalkyl,
(e) phenyl, or
(f) benzyl; and $R^{15}$ is:
(a) H,
(b) aryl, which is unsubstituted or substituted with 1 or 2 substituents selected from the group consisting of: Cl, Br, I, F, —O—($C_1$–$C_4$)-alkyl, ($C_1$–$C_4$)-alkyl, —$NO_2$, —$CF_3$, —$SO_2NR^2R^{2a}$, —S—($C_1$–$C_4$)-alkyl, —OH, —$NH_2$, ($C_3$–$C_7$)-cycloalkyl, ($C_3$–$C_{10}$)-alkenyl;
(c) ($C_1$–$C_6$)-alkyl, ($C_2$–$C_6$)-alkenyl or ($C_2$–$C_6$)-alkynyl each of which is unsubstituted or substituted with one or more substituents selected from the group consisting of: aryl, ($C_3$–$C_7$)-cycloalkyl, Cl, Br, I, F, —OH, —$NH_2$, —NH[($C_1$–$C_4$)-alkyl], —N[($C_1$–$C_4$)-alkyl]$_2$, —NH—$SO_2R^{2a}$, —$COOR^{2a}$, —$SO_2NHR^{2a}$; or
(d) an unsubstituted, monosubstituted or disubstituted aromatic 5 or 6 membered ring which can contain one or two heteroatoms selected from the group consisting of N, O, S, and wherein the substituents are members selected from the group consisting of —OH, —SH, ($C_1$–$C_4$)-alkyl, ($C_1$–$C_4$)-alkyloxy, —$CF_3$, Cl, Br, I, F, or $NO_2$; and $R^{16}$ is:
(a) aryl, or
(b) ($C_1$–$C_4$)-alkyl, is unsubstituted or substituted with:
  i) $NH_2$,
  ii) NH[($C_1$–$C_4$)-alkyl],
  iii) N[($C_1$–$C_4$)-alkyl]$_2$,
  iv) $CO_2H$,
  v) $CO_2$($C_1$–$C_4$)-alkyl,
  vi) OH,
  vii) $SO_3H$, or
  viii) $SO_2NH_2$; and $R^{17}$ is:
(a) H,
(b) ($C_1$–$C_4$)-alkyl,
(c) ($C_1$–$C_4$)-alkoxyl,
(d) aryl,
(e) aryl-($C_1$–$C_4$)-alkyl,
(f) $CO_2R^{2a}$,
(g) $CON(R^2)_2$,
(h) $SO_2R^{2a}$,
(i) $SO_2N(R^2)_2$,
(j) $P(O)[(C_1$–$C_4$)-alkoxyl]$_2$, or
(k) imidazol-2-yl or imidazol-4-yl, in which the imidazolyl can be substituted with ($C_1$–$C_4$)-alkyl; and $R^{18}$ is:
(a) OH,
(b) $NR^2R^{16}$,
(c) $CO_2R^{2a}$,
(d) $CON(R^2)_2$,
(e) $S(O)_n$—($C_1$–$C_4$)-alkyl, or
(f) $N(CH_2CH_2)_2Q$, $R^{19}$ is:
(a) ($C_1$–$C_4$)-alkyl,
(b) $CHR^{20}$—O—$COR^{21}$,
(c) $CH_2CH_2$—N[($C_1$–$C_2$)-alkyl]$_2$,
(d) $CH_2CH_2$—N[$CH_2CH_2$]$_2$O,
(e) ($CH_2CH_2O)_y$—O—[($C_1$–$C_4$)-alkyl], wherein y is 1 or 2,
(f) aryl or $CH_2$-aryl, where aryl is as defined above or optionally substituted with $CO_2(C_1$–$C_4$)-alkyl,

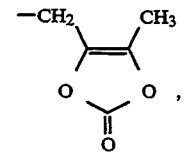

(g)

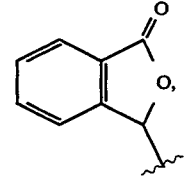

(h)

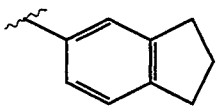

(i)

or

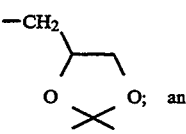

; and $R^{20}$ and $R^{21}$ independently are: ($C_1$–$C_6$)-alkyl or phenyl.

Wherein an embodiment is:

$R^1$ is:
(a) ($C_1$–$C_6$)-alkyl or ($C_2$–$C_6$)-alkenyl or ($C_2$–$C_6$)-alkynyl each of which is unsubstituted or substituted with a substituent selected from the group consisting of:
  i) ($C_1$–$C_4$)-alkylthio,
  ii) ($C_1$–$C_4$)-alkoxy,
  iii) $CF_3$,
  iv) $CF_2CF_3$, or v) ($C_3$–$C_5$)-cycloalkyl,
(b) ($C_1$–$C_4$)-perfluoroalkyl, or
(c) ($C_3$–$C_5$)-cycloalkyl; and E is:
(a) single bond,
(b) —S—, or
(c) —O—; and n is: 0, 1, or 2; and J is: (a) —C(=M)—, (b) J and L are connected together to form a 6-membered aromatic ring substituted with $R^{7a}$, $R^{7b}$, $R^{8a}$ and $R^{8b}$ or (c) J and L are connected together to form a 6-membered aromatic ring containing one nitrogen atom not at J, substituted with $R^{7a}$, $R^{7b}$, $R^{8a}$ and $R^{8b}$; and K is: (a) —C(=M)—, or (b) K and L are connected together to form a 6-membered aromatic ring substituted with $R^{7a}$, $R^{7b}$, $R^{8a}$ and $R^{8b}$, or (c) K and L are connected together to form a six-membered aromatic ring containing one nitrogen atom substituted with $R^{7a}$, $R^{7b}$ and $R^{8a}$ provided that one and only one of J and K is —C(=M)—; and one of a or b is a double bond in Formula I provided that when J is —C(=M)— then b is a double bond and when K is —C(=M)— then a is a double bond;

L is: the point of attachment of the 6-membered fused aromatic ring optionally containing one nitrogen atom; and M is: O, S or $NR^{15}$; and $R^2$ is:
(a) H,
(b) ($C_1$–$C_6$)-alkyl; and $R^{2a}$ is:
(a) $R^2$,
(b) $CH_2$aryl, or
(c) aryl; and $R^{7a}$ and $R^{7b}$ are independently:
(a) H,
(b) ($C_1$–$C_6$)-alkyl, ($C_2$–$C_6$)-alkenyl or ($C_2$–$C_6$)-alkynyl,
(c) Cl, Br, I, F,
(d) $CF_3$, or
(e) when $R^{7a}$ and $R^{7b}$ are bonded to adjacent carbon atoms, they can be joined to form a phenyl ring;

$R^{8a}$ and $R^{8b}$ are independently:
(a) H,
(b) aryl-($C_1$–$C_4$)-alkyl,
(c) heteroarylo($C_1$–$C_4$)-alkyl,
(d) ($C_1$–$C_6$)-alkyl, is unsubstituted or substituted with a substituent selected from the group consisting of: —CON($R^{2a}$)$_2$, —heteroaryl, —S(O)$_n$—$R^{16}$, —tetrazol-5-yl, —CONHSO$_2R^{16}$, —SO$_2$NH-heteroaryl, —SO$_2$NHCOR$^{16}$, —PO(OR$^2$)$_2$, —PO(OR$^{2a}$)$_2$, —SO$_2$NH—CN, —NR$^2$COOR$^{16}$, —OH, —NH$_2$, guanidino, ($C_1$–$C_4$)-alkoxy, ($C_1$–$C_4$)-alkylthio, ($C_1$–$C_4$)-alkylamino, ($C_1$–$C_4$)-dialkylamino, —COOR$^{2a}$, —CONHR$^{2a}$, —O—COR$^{2a}$, or aryl,
(e) —CO-aryl,
(f) ($C_3$–$C_7$)-cycloalkyl,
(g) Cl, Br, I, F,
(h) —OH,
(i) —OR$^{16}$,
(j) —SH,
(k) —S(O)$_n$—($C_1$–$C_4$)-alkyl,
(l) —COR$^{2a}$,
(m) —CO$_2$H,
(n) —CO$_2$-($C_1$–$C_4$)-alkyl,
(o) —SO$_3$H,
(p) —NR$^2R^{16}$,
(q) —NR$^2$COR$^{16}$,
(r) —NR$^2$COOR$^{16}$,
(s) —SO$_2$NR$^{2a}$,
(t) —SO$_2$NR$^2R^{2a}$,
(u) —NO$_2$,
(v) —NHSO$_2$CF$_3$,
(w) —CONR$^{2a}R^{2a}$,
(x) —($C_1$–$C_4$)-perfluoroalkyl,
(y) —COOR$^2$,
(z) —SO$_3$H,
(aa) —N(R$^2$)SO$_2R^{16}$,
(bb) —NR$^2$CONR$^{2a}R^{16}$,
(cc) —OC(=O)NR$^{16}R^{2a}$,
(dd) —aryl,
(ee) —NHSO$_2$CF$_3$,
(ff) —SO$_2$NH-heteroaryl,
(gg) —SO$_2$NHCOR$^{16}$,
(hh) —CONHSO$_2R^{16}$,
(ii) —PO(OR$^2$)$_2$,
(jj) —tetrazol-5-yl,
(kk) —CONH(tetrazol-5-yl),
(ll) —SO$_2$NHCN, or
(mm) —heteroaryl; and $R^9$ and $R^{10}$ are independently:
(a) H,
(b) ($C_1$–$C_6$)-alkyl, unsubstituted or substituted with ($C_3$–$C_7$)-cycloalkyl,
(c) ($C_2$–$C_6$)-alkenyl,
(d) ($C_2$–$C_6$)-alkynyl,
(e) Cl, Br, F, I,
(f) ($C_1$–$C_6$)-alkoxy,
(g) when $R^9$ and $R^{10}$ are on adjacent carbons, they can be joined to form a phenyl ring,
(h) ($C_1$–$C_6$)-perfluoroalkyl,
(i) ($C_3$–$C_7$)-cycloalkyl, unsubstituted or substituted with ($C_1$–$C_6$)-alkyl,
(j) aryl,
(k) ($C_1$–$C_6$)-alkyl-S(O)$_n$—(CH$_2$)$_n$—,
(l) hydroxy-($C_1$–$C_6$)-alkyl,
(m) —CF$_3$,
(n) —CO$_2R^{2a}$,
(o) —OH,
(p) —NR$^2R^{16}$,
(q) —[($C_1$–$C_6$)-alkyl]NR$^2R^{16}$,
(r) —NO$_2$,
(s) —(CH$_2$)$_n$—SO$_2$—N(R$^2$)$_2$,
(t) —NR$^2$CO—($C_1$–$C_4$)-alkyl, or
(u) —CON(R$^2$)$_2$; and X is:
(a) —O—,
(b) —S(O)$_n$—,
(c) —NR$^{13}$—,
(d) —CH$_2$O—,
(e) —CH$_2$S(O)$_n$,
(f) —CH$_2$NR$^{13}$—,
(g) —OCH$_2$—,
(h) —NR$^{13}$CH$_2$—,
(i) —S(O)$_n$CH$_2$—, or p1 (j) single bond; and Y is:
(a) single bond,
(b) —O—,
(c) —S(O)n—, or
(d) —NR$^{13}$—; and except that X and Y are not defined in such a way that the carbon atom to which Z is attached also simultaneously is bonded to two heteroatoms (O, N, S, SO, SO$_2$);

$R^{11}$ and $R^{12}$ are independently:

(a) H,
(b) $(C_1-C_6)$-alkyl, unsubstituted or substituted with a substituent selected from the group consisting of:
  (i) aryl,
  (ii) $(C_3-C_7)$-cycloalkyl,
  (iii) $NR^2R^{16}$,
  (iv) morpholin-4-yl,
  (v) OH,
  (vi) $CO_2R^{2a}$, or
  (vii) $CON(R^2)_2$,
(c) aryl or aryl-$(C_1-C_2)$-alkyl, unsubstituted or substituted with 1 to 3 substituents selected from the group consisting of:
  (i) Cl, Br, I, F,
  (ii) $(C_1-C_6)$-alkyl,
  (iii) $[(C_1-C_5)$-alkenyl]$CH_2$—,
  (iv) $[(C_1-C_5)$-alkynyl]$CH_2$—,
  (v) $(C_1-C_6)$-alkyl-$S(O)_n$—$(CH_2)_n$—,
  (vi) —$CF_3$,
  (vii) —$CO_2R^{2a}$,
  (viii) —OH,
  (ix) —$NR^2R^{16}$,
  (x) —$NO_2$,
  (xi) —$NR^2COR^2$,
  (xii) —$CON(R^2)_2$,
  (xiii) —G—$[(C_1-C_6)$-alkyl]-$R^{18}$,
  (xiv) —$N[CH_2CH_2]_2Q$, or
  (xv) —$P(O)[O-(C_1-C_4)$-alkyl]$_2$, and additionally be substituted with 1 or 2 substituents selected from the group consisting of: Br, Cl or F,
(d) $(C_3-C_7)$-cycloalkyl, or
(e) when Y is single bond, $R^{11}$ and $R^{12}$ can be joined to form a ring of 5 to 7 carbon atoms, the ring can be benzo-fused and one carbon of which can be replaced with a heteroatom selected from the group consisting of: O, $S(O)_n$ and $NR^{17}$; and
G is: a single bond, O, $S(O)_n$ or $NR^{18}$; and
Q is: O, $S(O)_n$ or $NR^{17}$; and
$R^{13}$ is:
(a) H,
(b) $(C_1-C_6)$-alkyl,
(c) aryl,
(d) aryl-$(C_1-C_6)$-alkyl-$(C=O)$—,
(e) $(C_1-C_6)$-alkyl-$(C=O)$—,
(f) $[(C_2-C_5)$-alkenyl]$CH_2$—,
(g) $[(C_2-C_5)$-alkynyl]$CH_2$—, or
(h) aryl-$CH_2$—; and
Z is:
(a) —$CO_2H$,
(b) —$CO_2R^{19}$,
(c) —tetrazol-5-yl,
(d) —CONH(tetrazol-5-yl),
(e) —$CONHSO_2$-aryl, wherein aryl is phenyl or naphthyl, which is unsubstituted or substituted as defined in $R^1$(b),
(f) —$CONHSO_2$-$(C_1-C_8)$-alkyl, wherein the alkyl group is unsubstituted or substituted with a substituent selected from the group consisting of: —OH, —SH, —$O(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —$NH[(C_1-C_4)$-alkyl], —$N[(C_1-C_4)$-alkyl]$_2$; and
(g) —$CONHSO_2$-$(C_1-C_4)$-perfluoroalkyl,
(h) —$CONHSO_2$-heteroaryl, wherein heteroaryl is unsubstituted or substituted as defined in $R^1$(c),
(i) —$CONHSO_2NR^{2a}R^{2a}$,
(j) —$SO_2NHCO$-aryl, wherein aryl is phenyl or naphthyl, which is unsubstituted or substituted as defined in $R^1$(b),
(k) —$SO_2NHCO$-$(C_1-C_8)$-alkyl, wherein the alkyl group is unsubstituted or substituted with a substituent selected from the group consisting of: —OH, —SH, —$O(C_1-C_4)$-alkyl, —S—$(C_1-C_4)$-alkyl, —$CF_3$, Cl, Br, F, I, —$NO_2$, —$CO_2H$, —$CO_2$-$(C_1-C_4)$-alkyl, —$NH_2$, —$NH[(C_1-C_4)$-alkyl], —$N[(C_1-C_4)$-alkyl]$_2$; and
(l) —$SO_2NHCO$-$(C_1-C_4)$-perfluoroalkyl,
(m) —$SO_2NHCO$-heteroaryl, wherein heteroaryl is unsubstituted or substituted as defined in $R^1$(c), or
(n) —$SO_2NHCONR^{2a}R^{2a}$; and
$R^{15}$ is:
(a) H,
(b) aryl, is unsubstituted or substituted with 1 or 2 substituents selected from the group consisting of Cl, Br, I, F, —O—$(C_1-C_4)$-alkyl, $(C_1-C_4)$-alkyl, —$NO_2$, —$CF_3$, —$SO_2NR^2R^{2a}$, —S—$(C_1-C_4)$-alkyl, —OH, —$NH_2$, $(C_3-C_7)$-cycloalkyl, $(C_3-C_{10})$-alkenyl;
(c) $(C_1-C_6)$-alkyl, $(C_2-C_6)$-alkenyl or $(C_2-C_6)$-alkynyl each of which is unsubstituted or substituted with one or more substituents selected from the group consisting of: aryl, $(C_3-C_7)$-cycloalkyl, Cl, Br, I, F, —OH, —$NH_2$, —$NH[(C_1-C_4)$-alkyl], —$N[(C_1-C_4)$-alkyl]$_2$, —NH—$SO_2R^{2a}$, —$COOR^{2a}$, —$SO_2NHR^{2a}$; or
(d) an unsubstituted, monosubstituted or disubstituted aromatic 5 or 6 membered ring which contains one or two heteroatoms selected from the group consisting of N, O, S, and wherein the substituents are members selected from the group consisting of —OH, —SH, $(C_1-C_4)$-alkyl, $(C_1-C_4)$-alkyloxy —$CF_3$, Cl, Br, I, F, or $NO_2$; and
$R^{16}$ is:
(a) aryl, or
(b) $(C_1-C_4)$-alkyl which is unsubstituted or substituted with:
  i) $NH_2$,
  ii) $NH[(C_1-C_4)$-alkyl],
  iii) $N[(C_1-C_4)$-alkyl]$_2$,
  iv) $CO_2H$,
  v) $CO_2(C_1-C_4)$-alkyl,
  vi) OH,
  vii) $SO_3H$, or
  viii) $SO_2NH_2$; and
$R^{17}$ is:
(a) H,
(b) $(C_1-C_4)$-alkyl,
(c) $(C_1-C_4)$-alkoxyl,
(d) aryl,
(e) aryl-$(C_1-C_4)$-alkyl,
(f) $CO_2R^{2a}$,
(g) $CON(R^2)_2$,
(h) $SO_2R^{2a}$,
(i) $SO_2N(R^2)_2$,
(j) $P(O)[(C_1-C_4)$-alkoxyl]$_2$, or
(k) imidazol-2-yl or imidazol-4-yl, in which the imidazolyl can be substituted with $(C_1-C_4)$-alkyl; and
$R^{18}$ is:
(a) OH,
(b) $NR^2R^{16}$,
(c) $CO_2R^{2a}$,
(d) $CON(R^2)_2$,
(e) $S(O)_n$—$(C_1-C_4)$-alkyl, or
(f) $N[CH_2CH_2]_2Q$; and $R^{19}$ is:
(a) $(C_1$-$C_4)$-alkyl,
(b) $CHR^{20}$—O—$COR^{21}$,
(c) $CH_2CH_2$-$N[(C_1$-$C_2)$-alkyl]$_2$,
(d) $CH_2CH_2$-$N[CH_2CH_2]_2O$,
(e) $(CH_2CH_2O)_y$—O—[$(C_1$-$C_4)$-alkyl], wherein y is 1 or 2,
(f) aryl or $CH_2$-aryl, where aryl is as defined above or optionally substituted with $CO_2(C_1$-$C_4)$-alkyl,

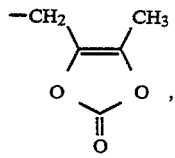
(g)

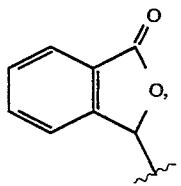
(h)

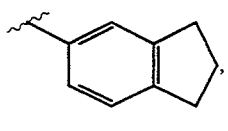
(i)

or

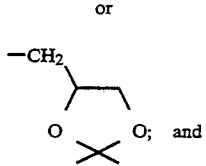
and $R^{20}$ and $R^{21}$ independently are: $(C_1$-$C_6)$-alkyl or phenyl.

Wherein another embodiment of the invention is when:
$R^1$ is:
(a) $(C_1$-$C_6)$-alkyl or $(C_2$-$C_6)$-alkenyl or $(C_2$-$C_6)$-alkynyl each of which is unsubstituted or substituted with a substituent selected from the group consisting of:
  i) $(C_1$-$C_4)$-alkylthio,
  ii) $(C_1$-$C_4)$-alkoxy,
  iii) $CF_3$,
  iv) $CF_2CF_3$, or
  v) $(C_3$—$C_5)$-cycloalkyl,
(b) $(C_1$-$C_4)$-perfluoroalkyl, or
(c) $(C_3$—$C_5)$-cycloalkyl; and
E is:
(a) single bond,
(b) —S—, or
(c) —O—; and
n is 0, 1, or 2; and J is: (a) —C(=M)—, (b) J and L are connected together to form a 6-membered aromatic ring substituted with $R^{7a}$, $R^{7b}$, $R^{8a}$ and $R^{8b}$ or (c) J and L are connected together to form a 6-membered aromatic ring containing one nitrogen atom not at J, substituted with $R^{7a}$, $R^{7b}$, $R^{8a}$ and R8b; and K is: (a) —C(=M)—, or (b) K and L are connected together to form a 6-membered aromatic ring substituted with $R^{7a}$, $R^{7b}$, $R^{8a}$ and $R^{8b}$, or (c) K and L are connected together to form a six-membered aromatic ring containing one nitrogen atom substituted with $R^{7a}$, $R^{7b}$ and $R^{8a}$ provided that one and only one of J and K is —C(=M)—; and one of a or b is a double bond in Formula I provided that when J is —C(=M)— then b is a double bond and when K is —C(=M)— then a is a double bond;

L is the point of attachment of the 6-membered fused aromatic ring optionally containing one nitrogen atom; and M is: O, S or $NR^{15}$; and
$R^2$ is:
(a) H,
(b) $(C_1$-$C_6)$-alkyl; and
$R^{2a}$ is:
(a) $R^2$,
(b) $CH_2$aryl, or
(c) aryl; and
$R^{7a}$ and $R^{7b}$ are independently:
(a) H,
(b) $(C_1$-$C_6)$-alkyl, $(C_2$-$C_6)$-alkenyl or $(C_2$-$C_6)$-alkynyl,
(c) Cl, Br, I, F,
(d) $CF_3$, or
(e) when $R^{7a}$ and $R^{7b}$ are bonded to adjacent carbon atoms, they can be joined to form a phenyl ring;
$R^{8a}$ and $R^{8b}$ are independently:
(a) H,
(b) aryl-$(C_1$-$C_4)$-alkyl,
(c) heteroaryl-$(C_1$-$C_4)$-alkyl,
(d) $(C_1$-$C_6)$-alkyl, is unsubstituted or substituted with a substituent selected from the group consisting of: —$CON(R^{2a})_2$, —heteroaryl, —$S(O)_n$—$R^{16}$, —tetrazol-5-yl, —$CONHSO_2R^{16}$, —$SO_2NH$-heteroaryl, —$SO_2NHCOR^{16}$, —$PO(OR^2)_2$, —$PO(OR^{2a})_2$, —$SO_2NH$—CN, —$NR^2COOR^{16}$, —OH, —$NH_2$, guanidino, $(C_1$-$C_4)$-alkoxy, $(C_1$-$C_4)$-alkylthio, $(C_1$-$C_4)$-alkylamino, $(C_1$-$C_4)$-dialkylamino, —$COOR^{2a}$, —$CONHR^{2a}$, —O—$COR^{2a}$, or aryl,
(e) —CO-aryl,
(f) $(C_3$-$C_7)$-cycloalkyl,
(g) Cl, Br, I, F,
(h) —OH,
(i) —$OR^{16}$,
(j) —SH,
(k) —$S(O)_n$—$(C_1$-$C_4)$-alkyl,
(l) —$COR^{2a}$,
(m) —$CO_2H$,
(n) —$CO_2$—$(C_1$-$C_4)$-alkyl,
(o) —$SO_3H$,
(p) —$NR^2R^{16}$,
(q) —$NR^2COR^{16}$,
(r) —$NR^2COOR^{16}$,
(s) —$SO_2NR^{2a}$,
(t) —$SO_2NR^2R^{2a}$,
(u) —$NO_2$,
(v) —$NHSO_2CF_3$,
(w) —$CONR^{2a}R^{2a}$,
(x) —$(C_1$-$C_4)$-perfluoroalkyl,
(y) —$COOR^2$,
(z) —$SO_3H$,
(aa) —$N(R^2)SO_2R^{16}$,
(bb) —$NR^2CONR^{2a}R^{16}$,
(cc) —$OC(=O)NR^{16}R^{2a}$,
(dd) —aryl,
(ee) —$NHSO_2CF_3$,
(ff) —$SO_2NH$-heteroaryl,
(gg) —$SO_2NHCOR^{16}$,
(hh) —$CONHSO_2R^{16}$, (ii) —PO(OR$^2$)$_2$,
(jj) —tetrazol-5-yl,
(kk) —CONH(tetrazol-5-yl),
(ll) —SO$_2$NHCN, or
(mm) —heteroaryl; and R$^9$ and R$^{10}$ are independently:
(a) H,
(b) (C$_1$–C$_6$)-alkyl, unsubstituted or substituted with (C$_3$–C$_7$)-cycloalkyl,
(c) (C$_2$–C$_6$)-alkenyl,
(d) (C$_2$–C$_6$)-alkynyl,
(e) Cl, Br, F, I,
(f) (C$_1$–C$_6$)-alkoxy,
(g) when R$^9$ and R$^{10}$ are on adjacent carbons, they can be joined to form a phenyl ring,
(h) (C$_1$–C$_6$)-perfluoroalkyl,
(i) (C$_3$–C$_7$)-cycloalkyl, unsubstituted or substituted with (C$_1$–C$_6$)-alkyl,
(j) aryl,
(k) (C$_1$–C$_6$)-alkyl-S(O)$_n$—(CH$_2$)$_n$—,
(l) hydroxy-(C$_1$–C$_6$)-alkyl,
(m) —CF$_3$,
(n) —CO$_2$R$^{2a}$,
(o) —OH,
(p) —NR$^2$R$^{16}$,
(q) —[(C$_1$–C$_6$)-alkyl]NR$^2$R$^{16}$,
(r) —NO$_2$,
(s) —(CH$_2$)$_n$—SO$_2$—N(R$^2$)$_2$,
(t) —NR$^2$CO-(C$_1$–C$_4$)-alkyl, or
(u) —CON(R$^2$)$_2$; and X is:
(a) —O—,
(b) —S(O)$_n$—,
(c) —NR$^{13}$—,
(d) —CH$_2$O—,
(e) —CH$_2$S(O)$_n$,
(f) —CH$_2$NR$^{13}$—,
(g) —OCH$_2$—,
(h) —NR$^{13}$CH$_2$—,
(i) —S(O)$_n$CH$_2$—, or
(j) single bond; and Y is:
(a) single bond,
(b) —O—,
(c) —S(O)$_n$—, or
(d) —NR$^{13}$—; and except that X and Y are not defined in such a way that the carbon atom to which Z is attached also simultaneously is bonded to two heteroatoms (O, N, S, SO, SO$_2$);

R$^{11}$ and R$^{12}$ are independently:
(a) H,
(b) (C$_1$–C$_6$)-alkyl, unsubstituted or substituted with a substituent selected from the group consisting of:
 (i) aryl,
 (ii) (C$_3$–C$_7$)-cycloalkyl,
 (iii) NR$^2$R$^{16}$,
 (iv) morpholin-4-yl,
 (v) OH,
 (vi) CO$_2$R$^{2a}$, or
 (vii) CON(R$^2$)$_2$,
(c) aryl or aryl-(C$_1$–C$_2$)-alkyl, unsubstituted or substituted with 1 to 3 substituents selected from the group consisting of:
 (i) Cl, Br, I, F,
 (ii) (C$_1$–C$_6$)-alkyl,
 (iii) [(C$_1$–C$_5$)-alkenyl]CH$_2$—,
 (iv) [(C$_1$–C$_5$)-alkynyl]CH$_2$—,
 (v) (C$_1$–C$_6$)-alkyl-S(O)$_n$—(CH$_2$)$_n$—,
 (vi) —CF$_3$,
 (vii) —CO$_2$R$^{2a}$,
 (viii) —OH,
 (ix) —NR$^2$R$^{16}$,
 (x) —NO$_2$,
 (xi) —NR$^2$COR$^2$,
 (xii) —CON(R$^2$)$_2$,
 (xiii) —G—[(C$_1$–C$_6$)-alkyl]-R$^{18}$,
 (xiv) —N[CH$_2$CH$_2$]$_2$Q, or
 (xv) —P(O)[O-(C$_1$–C$_4$)-alkyl]$_2$, and can additionally be substituted with 1 or 2 substituents selected from the group consisting of: Br, Cl or F,
(d) (C$_3$–C$_7$)-cycloalkyl, or
(e) when Y is single bond, R$^{11}$ and R$^{12}$ can be joined to form a ring of 5 to 7 carbon atoms, the ring can be benzo-fused and one carbon of which can be replaced with a heteroatom selected from the group consisting of: O, S(O)$_n$ and NR$^{17}$; and G is: a single bond, O, S(O)$_n$ or NR$^{18}$; and
Q is: O, S(O)$_n$ or NR$^{17}$; and
R$^{13}$ is:
(a) H,
(b) (C$_1$–C$_6$)-alkyl,
(c) aryl,
(d) aryl-(C$_1$–C$_6$)-alkyl-(C=O)—,
(e) (C$_1$–C$_6$)-alkyl-(C=O)—,
(f) [(C$_2$–C$_5$)-alkenyl]CH$_2$—,
(g) [(C$_2$–C$_5$)-alkynyl]CH$_2$—, or
(h) aryl—CH$_2$—; and Z is:
(a) —CO$_2$H,
(b) —CO$_2$R$^{19}$,
(c) —tetrazol-5-yl,
(d) —CONH(tetrazol-5-yl),
(e) —CONHSO$_2$-aryl, wherein aryl is phenyl or naphthyl, which is unsubstituted or substituted as defined in R$^1$(b),
(f) —CONHSO$_2$-(C$_1$–C$_8$)-alkyl, wherein the alkyl group is unsubstituted or substituted with a substituent selected from the group consisting of: —OH, —SH, —O(C$_1$–C$_4$)-alkyl, —S—(C$_1$–C$_4$)-alkyl, —CF$_3$, Cl, Br, F, I, —NO$_2$, —CO$_2$H, —CO$_2$-(C$_1$–C$_4$)-alkyl, —NH$_2$, —NH[(C$_1$–C$_4$)-alkyl], —N[(C$_1$–C$_4$)-alkyl]$_2$; and
(g) —CONHSO$_2$-(C$_1$–C$_4$)-perfluoroalkyl,
(h) —CONHSO$_2$-heteroaryl, wherein heteroaryl is unsubstituted or substituted as defined in R$^1$(c),
(i) —CONHSO$_2$NR$^{2a}$R$^{2a}$,
(j) —SO$_2$NHCO-aryl, wherein aryl is phenyl or naphthyl, which is unsubstituted or substituted as defined in R$^1$(b),
(k) —SO$_2$NHCO-(C$_1$–C$_8$)-alkyl, wherein the alkyl group is unsubstituted or substituted with a substituent selected from the group consisting of: —OH, —SH, —O(C$_1$–C$_4$)-alkyl], —S—(C$_1$–C$_4$)-alkyl, —CF$_3$, Cl, Br, F, I, —NO$_2$, —CO$_2$H, —CO$_2$-(C$_1$–C$_4$)-alkyl, —NH$_2$, —NH[(C$_1$–C$_4$)-alkyl], —N[(C$_1$–C$_4$)-alkyl]$_2$; and
(l) —SO$_2$NHCO-(C$_1$–C$_4$)-perfluoroalkyl,
(m) —SO$_2$NHCO-heteroaryl, wherein heteroaryl is unsubstituted or substituted as defined in R$^1$(c), or
(n) —SO$_2$NHCONR$^{2a}$R$^{2a}$; and R$^{15}$ is:
(a) H,
(b) aryl, is unsubstituted or substituted with 1 or 2 substituents selected from the group consisting of Cl, Br, I, F, —O—(C$_1$–C$_4$)-alkyl, (C$_1$–C$_4$)-alkyl, —NO$_2$, —CF$_3$, —SO$_2$NR$^2$R$^{2a}$, —S—(C$_1$–C$_4$)-alkyl, —OH, —NH$_2$, (C$_3$–C$_7$)-cycloalkyl, (C$_3$–C$_{10}$)-alkenyl;

(c) (C$_1$–C$_6$)-alkyl, (C$_2$–C$_6$)-alkenyl or (C$_2$–C$_6$)-alkynyl each of which is unsubstituted or substituted with one or more substituents selected from the group consisting of: aryl, (C$_3$–C$_7$)-cycloalkyl, Cl, Br, I, F, —OH, —NH$_2$, —NH[(C$_1$–C$_4$)-alkyl], —N[(C$_1$–C$_4$)-alkyl]$_2$, —NH—SO$_2$R$^{2a}$, —COOR$^{2a}$, —SO$_2$NHR$^{2a}$; or (d) an unsubstituted, monosubstituted or disubstituted aromatic 5 or 6 membered ring which contains one or two heteroatoms selected from the group consisting of N, O, S, and wherein the substituents are members selected from the group consisting of —OH, —SH, (C$_1$–C$_4$)-alkyl, (C$_1$–C$_4$)-alkyloxy —CF$_3$, Cl, Br, I, F, or NO$_2$; and R$^{16}$ is:
(a) aryl, or
(b) (C$_1$–C$_4$)-alkyl which is unsubstituted or substituted with:
  i) NH$_2$,
  ii) NH[(C$_1$–C$_4$)-alkyl],
  iii) N[(C$_1$–C$_4$)-alkyl]$_2$,
  iv) CO$_2$H,
  v) CO$_2$(C$_1$–C$_4$)-alkyl,
  vi) OH,
  vii) SO$_3$H, or
  viii) SO$_2$NH$_2$; and R$^{17}$ is:
(a) H,
(b) (C$_1$–C$_4$)-alkyl,
(c) (C$_1$–C$_4$)-alkoxyl,
(d) aryl,
(e) aryl-(C$_1$–C$_4$)-alkyl,
(f) CO$_2$R$^{2a}$,
(g) CON(R$^2$)$_2$,
(h) SO$_2$R$^{2a}$,
(i) SO$_2$N(R$^2$)$_2$,
(j) P(O)[(C$_1$–C$_4$)-alkoxyl]$_2$, or
(k) imidazol-2-yl or imidazol-4-yl, in which the imidazolyl can be substituted with (C$_1$–C$_4$)-alkyl; and R$^{18}$ is:
(a) OH,
(b) NR$^2$R$^{16}$,
(c) CO$_2$R$^{2a}$,
(d) CON(R$^2$)$_2$,
(e) S(O)$_x$—(C$_1$–C$_4$)-alkyl, or
(f) N[CH$_2$CH$_2$]$_2$Q; and R$^{19}$ is:
(a) (C$_1$–C$_4$)-alkyl,
(b) CHR$^{20}$—O—COR$^{21}$,
(c) CH$_2$CH$_2$—N[(C$_1$–C$_2$)-alkyl]$_2$,
(d) CH$_2$CH$_2$—N[CH$_2$CH$_2$]$_2$O,
(e) (CH$_2$CH$_2$O)$_y$—O—[(C$_1$–C$_4$)-alkyl], wherein y is 1 or 2,
(f) aryl or CH$_2$-aryl, where aryl is as defined above or optionally substituted with CO$_2$(C$_1$–C$_4$)-alkyl,

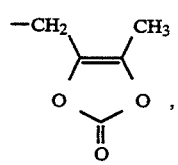 (g)

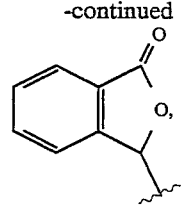 (h)

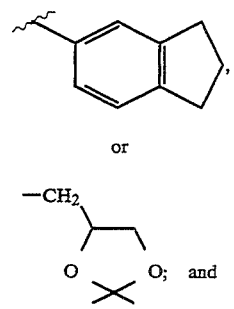 (i)

or

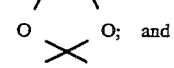

R$^{20}$ and R$^{21}$ independently are (C$_1$–C$_6$)-alkyl or phenyl.

The alkyl substituents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methylene groups, each of which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl substituent recited above represents any 5- or 6-membered aromatic ring containing from one to three heteroatoms selected from the group consisting of nitrogen, oxygen, and sulfur, for example, pyridyl, furyl, pyrrolyl, thienyl, isothiazolyl, imidazolyl, pyrazinyl, pyrimidyl, pyrazolyl, purinyl, carbazolyl, isoxazolyl, thiazolyl, and oxazolyl.

The compounds of Formula (I) can be synthesized using the reactions and techniques described in the International Application WO91/12001 published under the Patent Cooperation Treaty (to Merck & Co.) on Aug. 22, 1991. The above mentioned application discloses the compounds of this invention where they are described as angiotensin II receptor antagonists useful in the treatment of hypertension and ocular hypertension.

The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

The compounds useful in the novel method treatment of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, H$_2$SO$_4$, H$_3$PO$_4$, methanesulfonic, toluenesulfonic, maleic, fumaric, camphorsulfonic.

The salts can be formed by conventional means, such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be appreciated that the compounds of general Formula I in this invention may be derivatised at functional groups to provide prodrug derivatives which are capable of conversion back to the parent compounds in vivo. The concept of prodrug administration has been extensively reviewed (e.g. A. A. Sinkula in *Annual Reports in Medicinal Chemistry*, Vol 10, R. V. Heinzelman, Ed., Academic Press, New York London, 1975, Ch. 31, pp. 306–326), H. Ferres, *Drugs of Today*, Vol 19, 499–538 (1983) and *J. Med. Chem.*, 18, 172 (1975). Examples of such prodrugs include the physiologically acceptable and metabolically labile ester derivatives, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

It will be further appreciated that the majority of compounds of general Formula I claimed herein are asymmetric and are produced as racemic mixtures of enantiomers and that both the racemic compounds and the resolved individual enantiomers are considered to be in the scope of this invention. The racemic compounds of this invention may be resolved to provide individual enantiomers utilizing methods known to those skilled in the art of organic synthesis. For example, diastereoisomeric salts, esters or imides may be obtained from a racemic compound of general Formula I and a suitable optically active amine, amino acid, alcohol or the like. The diastereoisomeric salts, esters or imides are separated and purified, the optically active enantiomers are regenerated and the preferred enantiomer is the more potent isomer. The resolved enantiomers of the compounds of general Formula I, their pharmaceutically acceptable salts and their prodrug forms are also included within the scope of this invention.

Endothelin (ET-1), and two closely related bioactive peptides, ET-2 and ET-3, are widely distributed in mammalian tissues, and they can induce numerous biological responses in non-vascular as well as vascular tissues by binding to at least two distinct endothelin receptor subtypes. In addition to cardiovascular smooth muscle, neural and atrial sites, endothelin receptors may also be found in gastrointestinal, kidney, lung, urogenital, uteral and placental tissues.

Endothelin is a potent vasoconstrictor peptide and thus plays a role in vivo in arterial pressure-volume homeostasis. Not only peripheral, but coronary vascular resistance as well, is increased by endothelin. Cardiac output is decreased, while plasma renin activity is increased. There is a reduction in renal blood flow and glomerular filtration rate, while levels of atrial natriuretic factor, vasopressin, and aldosterone become elevated.

It is also considered, in accordance with the present invention, that antagonists for the endothelin receptor may be useful in preventing or reducing restenosis subsequent to denudation following angioplasty. Such denudation results from myointimal thickening following angioplasty, which is caused by increased endothelin release. Endothelin acts as a growth factor with respect to smooth muscle and fibroblastic cells, and possibly other types of cells, as well.

Endothelin is also a neuropeptide, acting on the posterior pituitary, where it modulates the release of the neurosecretory hormones vasopressin and oxytocin. Endothelin released from the posterior pituitary also acts as a circulating hormone, having a wide range of actions as discussed further above. This includes effects on the endocrine system, especially the adrenal glands. Endothelin increases plasma levels of epinephrine.

Consequently, the novel compounds of the present invention, which are receptor antagonists of endothelin, have therapeutic usefulness in preventing, decreasing or modulating the various physiological effects of endothelin discussed above, by wholly or partially blocking access of endothelin to its receptor.

Endothelin Receptor Binding Assays

The binding of the novel compound of this invention to the endothelin receptor was determined in accordance with the assay described in detail immediately below. It is similar to the assay described in Ambar et al. (1989) *Biochem. Biophys. Res. Commun.* 158, 195–201; and Kloog et al. (1989) *FEBS Letters*, 253, 199–202.

The endothelins (ETs) have a number of potent effects on a variety of cells, and exert their action by interacting with specific receptors present on cell membranes. The compounds described in the present invention act as antagonists of ET at the receptors. In order to identify ET antagonists and determine their efficacy in vitro, the following three ligand receptor assays were established.

Receptor Binding Assay Using Cow Aorta Membrane Preparation

Thoracic aortae were obtained from freshly slaughtered calves and brought to the lab on wet ice. The adventitia were removed, and the aorta was opened up lengthwise. The lumenal surface of the tissue was scrubbed with cheesecloth to remove the endothelial layer. The tissue was ground in a meat grinder, and suspended in ice-cold 0.25M sucrose, 5 mM tris-HCl, pH 7.4, containing 0.5 µg/mL leupeptin and 7 µg/mL pepstatin A. Tissue was homogenized twice and then centrifuged for 10 minutes at 750×g at 4° C. The supernatant was filtered through cheesecloth and centrifuged again for 30 minutes at 48,000×g at 4° C. The membrane pellet thus obtained was resuspended in the buffer solution described above (including the protease inhibitors), and aliquots were quick-frozen and stored at −70° C. until use. Membranes were diluted into 50 mM KPi, 5 mM EDTA pH 7.5 containing 0.01% human serum albumin. Assays were done in triplicate. Test compounds and 100 pM [$^{125}$I]-endothelin-1 (2000–2200 Ci/μmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration (IC$_{50}$) which gives 50% displacement of the total specifically bound [$^{125}$I]-endothelin-1 was presented as a measure of the potency of such compound as ET antagonist.

Receptor Binding Assay Using Rat Hippocampal Membrane Preparation

Rat hippocampi were obtained from freshly sacrificed male Sprague-Dawley rats and placed in ice cold 0.25M sucrose, 5 mM tris-HCl, pH 7.4 containing 0.5 μg/mL leupeptin, 7 μg/mL pepstatin A. Hippocampi were weighed and placed in a Dounce homogenizer with 25 volumes (wet weight to volume) ice-cold sucrose buffer in the presence of protease inhibitors. Hippocampi were homogenized using the Dounce (glass-glass) homogenizer with type A pestle, with the homogenizer immersed in ice. Tissue homogenate was centrifuged at 750×g for 10 min at 4° C. Supernatant was filtered through dampened cheesecloth, and centrifuged again at 48,000×g for 30 min at 4° C. Membrane pellets were resuspended in sucrose buffer with protease inhibitors. Aliquots of this preparation were quick frozen and stored at −70° C. until use. Membranes were diluted into 50 mM KPi, 5 mM EDTA pH 7.5 containing 0.01% human serum albumin. Assays were done in triplicate. Test compounds and 25 pM [$^{125}$I]-endothelin-1 (2000–2200 Ci/μmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration (IC$_{50}$) which gives 50% displacement of the total specifically bound [$^{125}$I]-endothelin-1 was presented as a measure of the potency of such compounds as endothelin antagonists.

Receptor Binding Assay Using Cloned Human ET Receptors Expressed In Chinese Hamster Ovary Cells Both endothelin receptor subtypes were cloned from a human cDNA library and were individually expressed in Chinese Hamster Ovary cells. Cells were harvested by addition of 126 mM NaCl, 5 mM KCl, 2 mM EDTA, 1 mM NaH$_2$PO$_4$, 15 mM glucose, 10 mM tris/HEPES pH 7.4 Cells were centrifuged at 250×g for 5 minutes. The supernatant was aspirated off, and the cells were resuspended in the 50 mM KPi, 5 mM EDTA pH 7.5 containing 0.01% human serum albumin. Assays were done in triplicate. Test compounds and 25–100 pM [$^{125}$I]-endothelin-1 (2000–2200 Ci/μmole, obtained from New England Nuclear or Amersham) were placed in a tube containing 50 mM KPi, 5 mM EDTA pH 7.5 containing 0.01% human serum albumin, and the cells prepared above were added last. The samples were incubated for 60 min at 37° C. At the end of this incubation, samples were filtered onto prewetted (with 2% BSA in water) glass fiber filter pad and washed with 150 mM NaCl, 0.1% BSA.

The filters were assayed for $^{125}$I radioactivity in a gamma counter. Nondisplaceable binding of [$^{125}$I]-endothelin-1 was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration (IC$_{50}$) which gives 50% displacement of the total specifically bound [$^{125}$I]-endothelin-1 was presented as a measure of the potency of such compounds as endothelin antagonists.

The binding assays described above were used to evaluate the potency of interaction of the compound of the invention with endothelin receptors. To determine whether these compounds are endothelin antagonists, assays which measure the ability of these compounds to inhibit endothelin-stimulated phosphatidylinositol hydrolysis were established. Rat uterus contains predominantly one of the known endothelin receptor subtypes (ET$_A$).

Phosphatidylinositol Hydrolysis Assays Using Rat Uterine Slices

Diethylstilbestrol primed female Sprague-Dawley rats were sacrificed and their uteri were collected, dissected of fat and connective tissue and minced. Minced tissue was added to oxygenated (95% O$_2$, 5% CO$_2$) 127 mM NaCl, 25 mM NaHCO$_3$, 10 mM Glucose, 2.5 mM KCl, 1.2 mM KH$_2$PO$_4$, 1.2 mM MgSO$_4$, 1.8 mM CaCl$_2$. To the tissue mince, 1.2 μM myo-[$^3$H]-inositol (Amersham) was added. The mince was incubated 90 min at 37° C., with constant oxygenation. After incubation, the loaded tissue mince was washed five times with the same oxygenated buffer to remove excess radiolabelled inositol. The tissue mince was resuspended in the above buffer, containing 10 mM LiCl, aliquotted into tubes, and 3 nM endothelin-1 with and without test compounds was added to a final concentration of 3 nM to start the assay. Assays were done in quadruplicate. Samples were incubated at 37° C. under blowing O$_2$ in a hooded water bath for 30 minutes. Reaction was stopped by addition of trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 μL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Sarafotoxin S6c is a member of the endothelin family which binds preferentially to one of the known endothelin receptor subtypes ($ET_B$).

Phosphatidylinositol Hydrolysis Assays Using Rat Lung Slices

Male Sprague-Dawley rats were sacrificed and their lungs were collected, dissected of fat and connective tissue and minced. Minced tissue was added to oxygenated (95% $O_2$, 5% $CO_2$) 127 mM NaCl, 25 mM NaHCO$_3$, 10 mM Glucose, 2.5 mM KCl, 1.2 mM KH$_2$PO$_4$, 1.2 mM MgSO$_4$, 1.8 mM CaCl$_2$. To the tissue mince, 1.2 $\mu$M myo-[$^3$H]-inositol was added. The mince was incubated 60 min at 37° C., with constant oxygenation. After incubation, loaded tissue mince was washed five times with the same oxygenated buffer to remove excess radiolabelled inositol. Tissue mince was resuspended in the above buffer, containing 10 mM LiCl, aliquotted into tubes, and sarafotoxin S6c (to a final concentration of 3 nM) with and without test compounds was added to start the assay. Assays were done in quadruplicate. Samples were incubated at 37° C. under blowing $O_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 $\mu$L aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of sarafotoxin minus the values in the absence of sarafotoxin (basal). Test sample values are the values in the presence of sarafotoxin and test sample minus basal. Inhibitory concentration ($IC_{50}$) is the concentration of test compound required to give a sample activity of 50% of control value.

Phosphatidylinositol Hydrolysis Assays Using Cloned Human Endothelin Receptors Expressed In Chinese Hamster Ovary Cells Endothelin receptors of both receptor subtypes were cloned from a human cDNA library and were individually expressed in Chinese Hamster Ovary cells. Cells were loaded overnight by the addition of 1.2 $\mu$M myo-[$^3$H]-inositol to their growth medium. Cells were harvested by addition of 126 mM NaCl, 5 mM KCl, 2 mM EDTA, 1 mM NaH$_2$PO$_4$, 15 mM glucose, 10 mM tris-/-HEPES pH 7.4 Cells were washed five times by centrifugation at 250×g for 5 minutes to remove excess radiolabelled inositol. The supernatant was aspirated off, and the cells were resuspended in the same oxygenated (95% $O_2$, 5% $CO_2$) buffer containing 10 mM LiCl, aliquotted into tubes, and endothelin-1 (to a final concentration of 0.3 nM) with and without test compounds was added to start the assay. Assays were done in quadruplicate. Samples were incubated at 37° C. under blowing $O_2$ in a hooded water bath for 30 minutes. Reaction was stopped by addition of 0.5mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 $\mu$L aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Using the methodology described above, the compounds of the invention were evaluated and found to exhibit $IC_{50}$ values of at least <50 $\mu$M thereby demonstrating and confirming the utility of the compounds of this invention as endothelin antagonists.

Accordingly the novel compounds of the present invention are useful in human therapy for treating asthma, hypertension, pulmonary hypertension, arterioscelerosis, heart failure, renal failure particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin, by adminstration to a patient in need of such treatment of a therapeutically effective amount thereof.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 0.5 mg.–1.0 g. per patient per day which can be administered in single or multiple doses. Preferably, the dosage range will be about 0.5–500 mg. per patient per day; more preferably about 0.5–100 mg. per patient per day.

The present invention also relates to pharmaceutical compositions for treating asthma, hypertension, pulmonary hypertension, arterioscelerosis, heart failure, renal failure particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin, comprising a therapeutically effective amount of the novel compound of this invention together with a pharmaceutically acceptable carder therefor.

About 0.5 mg to 1.0 g. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of Formula I and their incorporation into pharmaceutical compositions and as such are not to be considered as limiting the invention set forth in the claims appended hereto.

EXAMPLE 1

2-Butyl-3-[4-(1-Carboxy-1-Phenyl)Methoxyphenyl]-Methyl-6-Methylquinazolin -4(3H)-One

Step A

Preparation of
2-n-Butyl-6-Methylquinazolin-4(1H)-One

To a solution of 3.0 g (20 mmol) of 2-amino-5-methyl benzoic acid in 20 mL of dry DMF at 0° C. was added 200 mg of DMAP followed by 6.07 g (60 mmol) of triethylamine and 5.02 g (40 mmol) of valeryl chloride. The resulting mixture was stirred at 0° C. for 30 min. The mixture was heated to 110° C. and monitored by TLC for the formation of the intermediate quinoxazolone ($R_f$=0.8, 40% EtOAc/hexane). Following complete formation of the intermediate 10 g (100 mmol) of $(NH_4)_2CO_3$ was added cautiously. Heating was continued to ensure consumption of the quinoxazolone and formation of the polar ($R_f$=0.4, 40% EtOAc/hexane) quinazolin-4(1H)-one. The reaction mixture was concentrated in vacuo and the residue was taken up in 50 mL of ether and 50 mL of water. The mixture was filtered and the filtrate discarded after washing the residue with 20 mL of ether. The residue was recrystalized from MeOH to give 1.07 g (25%) of the title compound as a white crystalline solid.

$^1$H NMR (300 MHz, $CDCl_3$, ppm): δ0.94 (t, 3H, J=6.7 Hz), 1.50 (m, 2H), 1.83 (m, 2H), 2.49 (s, 3H), 2.78 (t, 2H), 7.60 (m, 2H), 8.05 (m, 1H).

Anal ($C_{13}H_{16}N_2O$), C, H, N.

Step B

Preparation of Methyl
2-(4-Methylphenoxy)Phenylacetate

To a suspension of KH (212 mg, 1.0 eq) in DMF (3 mL) was added a solution of p-cresol (200 mg; 1.85 mmol) in DMF (2 mL) followed by 18-crown-6 (50 mg, 0.2 eq). After stirring the reaction 45 minutes until the foaming subsides, a solution of methyl 2-bromophenylacetate (424 mg, 1.0 eq) in DMF (1 mL) was added, resulting in a purple solution that slowly faded to yellow. The reaction mixture was stirred 2.5 hours and was then concentrated in vacuo. The residue was chromatographed on a flash silica column (130×30 mm) eluted with 5% ethyl actate/hexane to yield 281 mg (62%) of the title compound ($R_f$=0.38, 5% ethyl acetate/hexane).

$^1$H NMR (300 MHz, $CDCl_3$, ppm): δ2.3 (s, 3H), 3.75 (s, 3H), 5.6 (s, 1H), 6.8–6.9 (d, 2H), 7.0–7.1 (d, 2H), 7.3–7.45 (m, 3H), 7.5–7.6 (d, 2H).

FAB-MS: m/e 257 (M+1).

Step C

Preparation of Methyl
2-(4-Bromomethylphenoxy)Phenylacetate

A solution of the product of Step B (50 mg, 0.205 mmol) NBS (33 mg, 0.9 eq) and AIBN (5 mg, catalytic amount) in $CCl_4$ (2 mL) was heated to reflux for 2 hours, and then concentrated in vacuo. The residue was chromatographed on a flash silica column (20×140 mm) eluted with 5% ethyl acetate/hexane to yield 32 mg (48%) of product ($R_f$=0.17, 5% ethyl acetate/hexane).

$^1$H NMR (300 MHz, $CDCl_3$, ppm): δ3.75 (s, 3H), 4.5 (s, 2H), 5.65 (s, 1H), 6.9–7.0 (d, 2H), 7.3–7.35 (d, 2H), 7.35–7.5 (m, 3H), 7.5–7.6 (d, 2H).

Step D

Preparation of
2-Butyl-3-[4-(1-Carbomethoxy-1-Phenyl)
-Methoxyphenyl]Methyl-6-Methyl
Quinazolin-4(3H)-One To a suspension of NaH (3 mg, 1.05 eq) in DMF (800 mL) at 0° C. was added 20 mg (0.0925 mmol) of the product of Step A and the reaction mixture was stirred for 15 minutes until the turbidity subsided. Next a solution of the product of Step C (31 mg, 1.0 eq) in DMF (0.2 mL) was added, the reaction was stirred for 18 hours, and then concentrated in vacuo. The residue was chromatographed on a flash silica gel column (120×20 mm) eluted with 15% ethyl acetate/hexane to yield 23 mg (53%) of the title compound ($R_f$=0.15, 15% ethyl acetate/hexane).

$^1$H NMR (300 MHz, CDCl$_3$, ppm): δ0.9–1.0 (t, 3H), 1.3–1.5 (m, 2H), 1.65–1.8 (m, 2H), 2.5 (s, 3H), 2.7–2.8 (t, 2H), 3.75 (s, 3H), 5.3 (s, 2H), 5.6 (s, 1H), 6.85–6.95 (d, 2H), 7.05–7.15 (d, 2H), 7.35–7.45 (m, 3H), 7.5–7.6 (m, 4H), 8.1 (s, 1H).

FAB-MS: m/e 47 1 (M+1).

Step E

Preparation of
2-Butyl-3-[4-(1-Carboxy-1-Phenyl)Methoxyphenyl]-Methyl -6-Methylquinazolin-4(3H)-One To a solution of the product of Step D (22 mg, 0.047 mmol) in MeOH (5 mL) was added 1N NaOH (2 mL). The reaction mixture was stirred 0.5 hours, and was then concentrated in vacuo. The residue was taken up in water and acidified to pH=2 with 1N HCl. Next, the aqueous layer was partitioned with chloroform and extracted 3 times. The combined organic layers were dried (MgSO$_4$), filtered and the filtrate concentrated in vacuo to yield 15 mg (65%) of the title compound ($R_f$=0.40, hexane/ethyl acetate/acetic acid (75:23.5:1.5)).

$^1$H NMR (300 MHz, CDCl$_3$, ppm): δ0.8–0.9 (t, 3H), 1.2–1.4 (m, 2H), 1.55–1.7 (m, 2H), 2.45 (s, 3H), 2.65–2.75 (t, 2H), 5.2–5.4 (br s, 2H), 5.6 (s, 1H), 6.9–7.0 (d, 2H), 7.05–7.15 (d, 2H), 7.35–7.45 (m, 3H), 7.5–7.65 (m, 4H), 8.1 (s, 1H).

FAB-MS: m/e 457 (M+1).

EXAMPLE 2

2-Butyl-3-[4-((1-carboxy-1-Phenyl)Methoxy)-3-Allyl]-Phenyl]Methyl-6-Methylquinazolin -4(3H)-One

Step A

Preparation of 4-(2-Propen-1-Yl-oxy)Benzyl Alcohol

To a suspension of NaH (130 mg; 4.33 mmol) in DMF (5 mL) at 0° C. under nitrogen was added a solution of 4-hydroxmethylphenol (512 mg; 4.12 mmol) in DMF (5 mL). After stirring 5 minutes at room temperature, a solution of allyl bromide (375 mL, 4.33 mmol) in DMF (5 mL) was added dropwise. The reaction was stirred for 20 minutes at 0° C., then quenched with water and concentrated in vacuo. The residue was partitioned between water and ethyl acetate. The combined organic layers were washed with 4% HCl, saturated NaHCO$_3$, and then brine, and dried (MgSO$_4$), filtered and concentrated in vacuo to yield 650 mg (97%) of the title compound.

$^1$H NMR (300 MHz, CDCl$_3$, ppm): δ7.27 (dd, 2H), 6.90 (apparent d, 2H), 6.12–5.98 (m, 1H), 5.41 (apparent dd, 1H), 5.29 (dd, 1H), 4.58 (s, 2H), 4.52 (dd, 2H), 1.93 (br s, 1H).

Step B

Preparation of
4-Tert-Butyldimethylsilyloxymethylphenyl-(2-Propen-1-Yl) Ether

To a solution of the product of Step A (650 mg, 3.96 mmol) in CH$_2$Cl$_2$ (20 mL), cooled to 0° C. under nitrogen, was added triethylamine (612 mL, 4.39 mmol) and a solution of tert-butyldimethylsilyl chloride (631 mg; 4.19 mmol) in CH$_2$Cl$_2$ (2 mL). After stirring at room temperature for 18 hours, the reaction mixture was diluted with ethyl acetate (60 mL), washed with water, and saturated sodium bicarbonate, and then dried (MgSO$_4$). The filtrate was concentrated in vacuo to afford 1.1 g of the title compound which was used crude in the next reaction ($R_f$=0.45, 5% ethyl acetate/hexanes).

$^1$H NMR (300 MHz, CDCl$_3$, ppm): δ7.24 (d, 2H), 6.89 (d, 2H), 6.15–6.00 (m, 1H), 5.42 (apparent d, 1H), 5.30 (apparent d, 1H), 4.68 (s, 2H), 4.53 (apparent dd, 2H), 0.95 (s, 9H), 0.12 (s, 6H).

Step C

Preparation of
4-Tert-Butyldimethylsilyloxymethyl-2-Allylphenol

The product of Step B (0.51 g, 1.83 mmol) was heated to 200° C. under a nitrogen atmosphere for 5 hours. The crude reaction mixture was dissolved in eluant and chromatographed on silica (MPLC, 5/95 ethyl acetate/hexane) to afford 178 mg (35%) of the title compound ($R_f$=0.11, 5% ethyl acetate/hexanes).

$^1$H NMR (300 MHz, CDCl$_3$, ppm): δ7.10 (unsymmetrical d, 2H), 6.78 (d, 2H), 6.09–5.94 (m, 2H), 5.21–5.11 (m, 2H), 5.00 (s, 1H), 4.67 (s, 2H), 3.40 (d, 2H), 0.95 (s, 9H), 0.11 (s, 6H).

FAB MS: m/e=277 (M+1).

Step D

Preparation of Methyl
2-(4-Tert-Butyldimethylsilyloxymethyl -2-Allylphenoxy)-2-Phenylacetate To a suspension of KH (1.3 eq) in DMF (1 mL) was added a solution of the product of Step C (157 mg, 0.566 mmol) in DMF (1 mL), followed by 18-crown-6 (30 mg; 0.2 eq). The reaction mixture was stirred for 5 minutes at room temperature. A solution of methyl 2-bromophenylacetate (168 mg, 0.735 mmol) in DMF (1 mL) was added, followed by a catalytic amount of potassium iodide. The reaction was heated to 80° C. for 0.5 hours then stirred at room temperature for 16 hours. After concentration in vacuo, the residue was partitioned between water and ethyl acetate. The combined organic layers were washed with water, brine, then dried (MgSO$_4$). After filtration and concentration in vacuo, the residue was chromatographed on silica (MPLC, ethyl acetate/hexanes (5/95)) to afford 158 mg (66%) of the title compound ($R_f$=0.22, 5% ethyl acetate/hexanes).

$^1$H NMR (300 MHz, CDCl$_3$, ppm): δ7.64–7.57 (dd, 2H), 7.46–7.35 (m, 3H), 7.17–7.06 (m, 2H), 6.72 (d, 1H), 6.12–5.98 (m, 1H), 5.65 (s, 1H), 5.11–5.04 (m, 2H), 4.66 (s, 2H), 3.72 (s, 3H), 3.53 (d, 2H), 0.95 (s, 9H), 0.10 (s, 6H).

FAB MS: consistent with structure.

Step E

Preparation of Methyl
2-(4-Bromomethyl-2-Allylphenoxy)-2-Phenylacetate

To a cooled (0° C.) solution of the product of Step D (156 mg, 0.366 mmol) in CH$_3$CN (2 mL), were added carbon tetrabromide (182 mg, 0.55 mmol) and triphenylphosphine (144 mg, 0.55 mmol). After 30 minutes at 0° C., the reaction mixture was allowed to warm to room temperature, at which point acetone (40 mL, 0.55 mmol) was added. After 16 hours at room temperature, the reaction mixture was filtered, the filtrate was concentrated in vacuo, and the residue was purified on a silica gel flash chromatography column eluted with 5% ethyl acetate/hexanes to afford 86 mg (63 %) of the title compound ($R_f$=0.13, 5% ethyl acetate/hexanes).

$^1$H NMR (300 MHz, CDCl$_3$, ppm): δ7.67–7.57 (dd, 2H), 7.47–7.37 (m, 3H), 7.27–7.13 (m, 2H), 6.72 (d, 1H), 6.16–5.98 (m, 1H), 5.68 (s, 1H), 5.20–5.08 (m, 2H), 4.49 (s, 2H), 3.73 (s, 3H), 3.54 (d, 2H).

FAB MS: consistent with structure.

Step F

Preparation of 2-Butyl-3-[4-((1-Carbomethoxy-1-Phenyl)Methoxy)-3-Allylphenyl]Methyl-6-Methylquinazolin-4(3H)-One To a suspension of NaH (0.514 mmol) in DMF (2 mL) was added 92 mg (0.428 mmol) of 2-butyl-6-methylquinazolin-4(3H)-one (Step A of Example 1) and the reaction mixture was stirred for 30 minutes at room temperature. A solution of the product of Step E (177 mg, 0.47 1 mmol) in DMF (1.5 mL) was added, and the reaction was stirred at room temperature for 18 hours. The reaction mixture was then concentrated in vacuo and partitioned between water and ethyl acetate. The combined organic layers were washed with water then brine, dried (MgSO$_4$), filtered, and concentrated in vacuo. The residue was chromatographed on silica (MPLC, hexanes/ethyl acetate (4/1)) to afford 96 mg (44 %) of the title compound.

$^1$H NMR (300 MHz, CDCl$_3$, ppm): δ8.08 (s, 1H), 7.6–7.49 (br s, 4H), 7.42–7.28 (m, 3H), 7.09–7.01 (br s, 1H), 6.93–6.83 (br dd, 1H), 6.66 (d, 1H), 6.08–5.92 (m, 1H), 5.60 (s, 1H), 5.36–5.22 (br s, 2H), 5.12–4.98 (m, 2H), 3.68 (s, 3H), 3.48 (d, 2H), 3.48 (d, 2H), 2.72 (t, 2H), 2.48 (s, 3H), 1.80–1.65 (m, 2H), 1.40 (q, 2H), 0.90 (t, 3H).

FAB MS: m/e =511 (M+1).

Step G

Preparation of 2-Butyl-3-[4-((1-Carboxy-1-Phenyl)Methoxy)-3-Allylphenyl]Methyl-6-Methylquinazolin-4(3H)-One To a solution of the product of Step F (20 mg, 0.039 mmol) in MeOH (2 mL), were added 4 drops of water and 2.0N NaOH (22 μL, 0.043 mmol). After stirring for 18 hours at room temperature, the reaction mixture was concentrated in vacuo, dissolved in water/THF, and treated with HCl (0.15 mL, 1.0N) at room temperature for 30 minutes. The reaction mixture was then concentrated in vacuo and chromatographed on a Sephadex LH-20 column eluted with MeOH to afford 19 mg of crude product, which was recrystallized from MeOH to yield 2 mg(10%) of the title compound.

$^1$H NMR (300 MHz, CD$_3$OD, ppm): δ8.05 (s, 1H), 7.70 (d, 1H), 7.63–7.48 (m, 3H), 7.44–7.28 (m, 3H), 7.08 (s, 1H), 6.99–6.92 (m, 1H), 6.83 (d, 1H), 6.07–5.92 (m, 3H), 5.73 (s, 1H), 5.40 (s, 2H), 5.08–5.88 (m, 2H), 3.46 (br s, 2H), 2.80 (t, 2H), 2.51 (s, 3H), 1.68–1.57 (m, 2H), 1.43–1.28 (m, 2H), 0.88 (t, 3H).

FAB MS: m/e =497 (M+1).

EXAMPLE 3

2-Butyl-3-[4-((1-Carboxy-1-Phenyl)Methoxy)-3-Propylphenyl]Methyl-6-Methylquinazolin-4(3 H)-One

Step A

Preparation of 2-Butyl-3-[4-((1-Carbomethoxy-1-Phenyl)Methoxy)-3-Propylphenyl]Methyl-6-Methylquinazolin-4(3H)-One To a solution of the product of Example 2, Step F (20 mg, 0.039 mmol) in CH$_2$Cl$_2$ (2 mL), was added Wilkinson's catalyst (7.6 mg). The reaction mixture was hydrogenated at 40 psi, room temperature for 4.5 hours. After concentration in vacuo, the residue was chromatographed on silica (MPLC, hexanes/ethyl acetate (4/1) to afford 15 mg (78%) of the title compound.

$^1$H NMR (300 MHz, CDCl$_3$, ppm): δ8.10 (s, 1H), 7.63–7.54 (m, 4H), 7.46–7.36 (m, 3H), 7.02 (apparent s, 1H), 6.89 (dd, 1H), 6.63 (d, 1H), 5.62 (s, 1H), 5.32 (br s, 2H), 3.71 (s, 3H), 2.79–2.63 (m, 4H), 2.50 (s, 3H), 1.80–1.60 (m, 2H), 1.48–1.34 (m, 2H), 1.02–0.87 (m, 6H).

FAB-MS: m/e =513 (M+1).

Step B

Preparation of 2-Butyl-3-[4-((1-Carboxy-1-Phenyl)Methoxy)-3-Propylphenyl]Methyl-6-Methylquinazolin-4(3H)-One To a solution the product of Example 3, Step A (11 mg; 0.22 mmol) in MeOH (2 mL) was added NaOH (1.5 eq, 2.0N) and a few drops of water. After stirring for 20 hours at room temperature, the reaction mixture was concentrated in vacuo, dissolved in water/THF, treated with HCl (5 eq) for 30 minutes at room temperature, concentrated in vacuo, and chromatographed on a Sephadex LH-20 column eluting with MeOH to afford 11 mg (99%) of the title compound.

$^1$H NMR (300 MHz, CD$_3$OD, ppm): δ8.19 (s, 1H), 7.88 (d, 1H), 7,68 (d, 1H), 7.58 (dd, 2H), 7.48–7.33 (m, 3H), 7.18 (s, 1H), 7.08 (d, 1H), 6.84 (d, 1H), 5.70 (s, 1H), 5.48 (s, 2H), 3.15–3.03 (m, 2H), 2.69 (t, 2H), 2.53 (s, 3H), 1.72–1.5 (m, 4H), 1.49–1.34 (m, 2H), 0.98–0.84 (m, 6H).

FAB-MS: m/e =499 (M+1).

EXAMPLE 4

2-Butyl-3-[4-((1-Carboxy-1-Phenyl)Methoxy)-3-Chlorophenyl]Methyl-6-Methylquinazolin-4(3 H)-One

Step A

Preparation of Methyl 2-(2-Chloro-4-Methylphenoxy)-2-Phenylacetate

To a suspension of 0.282 g (7.04 mmol) of a 60% oil dispersion of sodium hydride in DMF was added 1.00 g (7.04 mmol) of 2-chloro-4-methylphenol and the mixture was stirred under an N$_2$ atmosphere at room temperature. After 10 minutes, a solution of 1.94 g (8.45 mmol) of methyl 2-bromophenylacetate dissolved in 10 mL of DMF was added and the reaction was stirred an additional 1.5 hours. The reaction was then diluted into ethyl acetate, washed with water, dried (MgSO$_4$), filtered and evaporated. The residue was purified on a silica gel flash chromatography column eluted with 4% ethyl acetate/hexane to afford 1.70 g (83%) of the title compound.

$^1$H NMR (300 MHz, CDCl$_3$, ppm): δ2.20 (s, 3H), 3.70 (s, 3H), 5.60 (s, 1H), 6.70–6.80 (d, 1H), 6.85–6.95 (d, 1H)L 7.20 (br s, 1H), 7.20–7.30 (m, 3H), 7.55–7.65 (m, 2H).

EI-MS: m/e 290 (M+).

Step B

Preparation of Methyl 2-(2-Chloro-4-Bromomethylphenoxy)-2-Phenylacetate

To a solution of 1.70 g (5.86 mmol) of the product from Step A dissolved in 20 mL of $CCl_4$ was added 1.04 g (5.86 mmol) of N-bromosuccinimide and 50 mg (catalytic amount) of AIBN. The reaction mixture was stirred and heated at reflux for 7 hours, then an additional 0.20 g of NBS was added. The reaction was refluxed for 48 hours, then cooled and concentrated in vacuo. The residue was purified on a silica gel flash chromatography column eluted with 10% ethyl acetate/hexane to afford 0.730 g (34%) of the title compound.

$^1$H NMR (300 MHz, $CDCl_3$, ppm): δ3.70 (s, 3H), 4.40 (s, 2H), 5.65 (s, 1H), 6.75–6.85 (d, 1H), 7.10–7.20 (d, 1H), 7.30–7.45 (m, 4H), 7.55–7.65 (m, 2H).

FAB-MS: m/e 369 (M+1).

Step C

Preparation of 2-Butyl-3-[4-((1-Carbomethoxy-1-Phenyl)Methoxy)-3-Chlorophenyl]-Methyl-6-methylquinazolin-4(3H)-One To a half suspension of 62 mg (0.287 mmol) of the product of Step A of Example 1 in 1.0 mL of anhydrous DMF was added 12 mg (1.05 eq) of a 60% oil dispersion of sodium hydride and the reaction mixture was stirred under an $N_2$ atmosphere. After stirring 10 minutes at room temperature, a solution of 0.127 g (1.2 eq) of the product of Step B dissolved in 1.0 mL DMF was added to the solution of the anion. The reaction mixture was then stirred overnight, then partitioned between water and ethyl acetate. The organic layer was separated, dried ($MgSO_4$) filtered and evaporated in vacuo. The residual oil was purified on a silica gel flash chromatography column eluted with 30% ethyl acetate/hexane to afford 76 mg (52%) of the title compound.

$^1$H NMR (300 MHz, $CDCl_3$, ppm): δ0.87–0.94 (t, 3H), 1.32–1.45 (m, 2H), 1.67–1.78 (m, 2H), 2.42 (s, 3H), 2.66–2.72 (t, 2H), 3.70 (s, 3H), 5.30 (br s, 2H), 5.60 (s, 1H), 6.77 (d, 1H), 6.94 (dd, 1H), 7.18 (s, 1H), 7.33–7.42 (m, 3H), 7.53–7.61 (m, 4H), 8.06 (s, 1H).

FAB-MS: m/e 505, 507 (M+1, 3:1 ratio).

Step D

Preparation of 2-Butyl-3-[4-((1-Carboxy-1-Phenyl)Methoxy)-3-Chlorophenyl]Methyl-6-Methylquinazolin-4(3 H)-One To a solution of 72 mg of the product of Step C dissolved in 2 mL of methanol, was added 0.25 mL of a 1N solution of NaOH and the reaction mixture was stirred at room temperature for 3 days. The reaction mixture was then adjusted to pH 7 with 1N HCl, concentrated in vacuo, and the residue was applied to a silica gel flash chromatography column and eluted with $CHCl_3$/MeOH/$NH_4OH$ (80:15:1). Evaporation of the purified fractions and drying in vacuo afforded 50 mg (71%) of the title compound.

$^1$H NMR (300 MHz, $CD_3OD$, ppm): δ0.92–0.98 (t, 3H), 1.37–1.48 (m, 2H), 1.66–1.77 (m, 2H), 2.54 (s, 3H), 2.78–2.84 (t, 2H), 5.40 (s, 2H), 5.68 (s, 1H), 7.01–7.10 (m, 2H), 7.31–7.44 (m, 4H), 7.58–7.72 (m, 4H), 8.07 (s, 1H).

FAB-MS: m/e 491,493 (M+1, 3:1 ratio).

EXAMPLE 5

3-[4-((1-Carboxy-1-Phenyl)Methoxy)-3-Chloro-5-Methoxyphenyl]Methyl-6-(N-Methyl-N-Iso-Butyloxycarbonyl)-Amino-2-Propylquinazolin-4(3 H)-One

Step A

Preparation of 2-Propyl-6-Nitro-Quinazolin-4(1H)-One

To a suspension of 48.94 g (0.3 tool) of 3-nitro-5-aminobenzonitrile in 500 mL of $CH_2Cl_2$ was added 63 mL of $Et_3N$, 3 g DMAP and lastly, dropwise, 45.5 g (0.45 mol) of butyryl chloride. A mild exothermic reaction ensued. The mixture was allowed to stir for 2 days (monitored by TLC with 50% EtOAc/hexanes). The solution was washed with 1N HCl (2×100 mL), water (1×100 mL), saturated $NaHCO_3$ (2×100 mL), brine (1×100 mL) and dried over $MgSO_4$. The suspension was filtered and concentrated in vacuo. The residue was suspended in a mixture of 600 mL of MeOH and 200 mL of water in a three neck round bottom flask. To this was added gradually 140 mL of 5N NaOH (0.7 mol) solution followed by the dropwise addition of 80 mL of 30% $H_2O_2$ (0.7 mmol) solution (exothermic). The mixture was refluxed overnight, cooled to room temperature and filtered. The filtrate was acidified with 1N HCl cooled to 5° C. and filtered. The quinazolinone was recrystallized from hot MeOH to give 38 g (54%) of the title compound as pale brown fine crystals.

$^1$H NMR (300 MHz, $CDCl_3$, ppm): δ1.10 (t, 3H, J=7.8 Hz), 1.93 (m, 2H), 2.79 (t, 2H, J=7.3 Hz), 7.81 (d, 1H, J=8.9 Hz), 8.55 (dd, 1H, J=2.4, 8.8 Hz), 9.14 (d, 1H, J=2.4 Hz), 10.72 (br s, 1H).

Step B

Preparation of 3-(4,4'-Dimethoxybenzhydryl)-2-Propyl-6-Nitroquinazolin-4 (3 H)-One To a suspension of 1.01 g (33.7 mmol) of 80% sodium hydride in 20 mL of dry DMF was added at 0° C. 7.5 g (32 mmol) of the product of Step A as a solid. The reaction mixture was diluted with a further 50 mL of DMF to assist stirring. After hydrogen evolution was complete, a solution of 8.8 g (33.7 mmol) of 4,4'-dimethoxybenzhydryl chloride in 20 mL of dry DMF was added dropwise. The reaction mixture was stirred overnight and then poured into 300 mL of 0.1N NaOH. The precipitate was collected by filtration and dried under vacuum to give 12.1 g (94%) of a yellow solid.

$^1$H-NMR (300 MHz, $CDCl_3$, ppm): δ0.87 (t, 3H, J=7.3 Hz), 1.58 (br m, 2H), 2.72 (t, 2H, J=7.8 Hz), 3.80 (s, 6H), 6.88 (d, 4H, J=9 Hz), 7.19 (d, 4H, J=9.0 Hz), 7.73 (d, 1H, J=8.9 Hz), 8.48 (dd, 1H, J=2.8, 9.0 Hz), 9.08 (d, 1H, J=2.8 Hz).

Step C

Preparation 6-Amino-3-(4,4'-Dimethoxybenzhydryl)-2-Propyl-Quinazolin-4(3H)-One A solution of 12.1 g (26.0 mmol) of the product of Step B dissolved in 250 mL of EtOAc was hydrogenated under atmospheric pressure over three days in the presence of three portions of 1.2 g of 10% Pd/C added daily. The mixture was filtered through celite and concentrated in vacuo to give an oil. The product was purified by flash chromatography over silica gel eluted with 50% EtOAc/hexanes to give 7.8 g (72%) of the amine.

$^1$H-NMR (300 MHz, CDCl$_3$, ppm): δ0.82 (t, 3H, J=7.2 Hz), 1.49 (br m, 2H), 2.61 (t, 2H, J=7.81 Hz), 3.79 (s, 6H), 3.90 (br s, 2H), 6.85 (d, 4H, J=8.8 Hz), 7.08 (dd, 1H, J=2.8, 8.7 Hz), 7.20 (d, 4H, J=8.4 Hz), 7.42 (d, 1H, J=2.7 Hz), 7.47 (d, 1H, J=8.7 Hz).

Step D

Preparation of
3-(4,4'-Dimethoxybenzhydryl)-6-(N-Methyl
-N-Isobutyloxycarbonyl)Amino-2-Propylquinazolin-
4(3 H)-One To a suspension of 81.5 mg (2.7 mmol) of 80% NaH in 3 mL of dry DMF at 0° C. under nitrogen was added dropwise a solution is of 1.03 g (2.5 mmol) of 6-amino-3-(4,4'-dimethoxybenzhydryl)-2-propylquinazolin-4(3H)-one dissolved in 3 mL of DMF. The resulting mixture was stirred for 30 minutes and then treated with 0.35 mL (2.7 mmol) of neat isobutylchloroformate. The solution was stirred for 30 minutes and then treated with 2.97 mL (2.97 mmol) of a 1M solution of lithium bis(trimethylsilyl)amide in THF. The dark solution was stirred for a further 30 minutes at 0° C. and then was treated with 0.2 mL (3.26 mmol) of neat iodomethane. The mixture was stirred overnight at room temperature, poured into 50 mL of EtOAc and washed consecutively with water (2×10 mL), brine (1×10 mL) and dried over MgSO$_4$. The product was purified by flash chromatography over silica gel eluted with 30% EtOAc/hexanes to give 0.9 g (71%) of the title compound as an oil.

$^1$H-NMR (300 MHz, CDCl$_3$, ppm): a 0.82–0.91 (m, 6H), 0.96 (d, 3H, J=6.8 Hz), 1.52 (m, 2H), 1.88 (m, 1H), 2.67 (br t, 2H), 3.35 (s, 3H), 3.80 (s, 6H), 3.90 (d, 2H, J=6.6 Hz), 6.87 (d, 4H, J=8.8 Hz), 7.20 (d, 4H, J=8.8 Hz), 7.61 (m, 1H), 7.78 (m, 1H), 8.01 (d, 1H, 2H).

Step E

Preparation of
6-(N-Methyl-N-Isobutyloxycarbonyl)Amino-2-Propyl-
quinazolin-4(3 H)-One The product of Step D (0.9 g, 1.7 mmol) was added to 3.0 mL of a 10:1 mixture of trifluoroacetic acid and anisole. The solution was stirred for 4 hours, concentrated in vacuo and the residue was purified by flash chromatography over silica gel eluted with 50% EtOAc/hexanes to give 0.47 g (88%) of the title compound as a white solid.

$^1$H-NMR (300 MHz, CDCl$_3$, ppm): δ0.89 (d, 6H, J=6.7 Hz), 1.07 (t, 3H, J=7.4 Hz), 1.92 (m, 2H), 2.76 (t, 2H, J=7.8 Hz), 3.40 (s, 3H), 3.93 (d, 2H, J=6.6 Hz), 7.70 (m, 2H), 8.10 (d, 1H, J=2.6 Hz).

Step F

Preparation of Methyl
2-(2-Chloro-4-Hydroxymethyl-6-Methoxyphenoxy)-2-
Phenylacetate To a solution of 0.500 g (2.65 mmol) of 3-chloro-4-hydroxy-5-methoxybenzyl alcohol (Bader) and 0.668 g (1.1 eq) of methyl 2-bromophenylacetate dissolved in 5 mL acetone was added 0.733 g (2 eq) of anhydrous potassium carbonate and the reaction mixture was stirred and refluxed overnight. The reaction mixture was cooled to room temperature, filtered and evaporated in vacuo. The residual oil was purified on a silica gel flash chromatography column eluted with 35% ethyl acetate/hexane to afford 0.570 g (64%) of the title compound.

$^1$H NMR (300 MHz, CDCl$_3$, ppm): δ1.65–1.75 (t, 1H), 3.70 (s, 3H), 3.80 (s, 3H), 4.55 (d, 2H), 5.75 (s, 1H), 6.80 (s, 1H), 6.90 (s, 1H), 7.30–7.40 (m, 3H), 7.50–7.60 (m, 2H).

FAB-MS: m/e 337, 339 (M+1, 3:1 ratio).

Step G

Preparation of
2-(4-Bromomethyl-2-Chloro-6-Methoxyphenoxy)-2-
Phenylacetate

To a stirred and cooled (0° C.) solution of 0.570 g (1.69 mmol) of the product of Step F dissolved in 6 mL of CH$_2$Cl$_2$ was added 0.702 g (2.11 mmol) of carbon tetrabromide and 0.555 g (2.11 mmol) of triphenylphosphine. After the addition the reaction mixture was allowed to warm to room temperature and was stirred 4 hours. The mixture was then evaporated in vacuo and purified on a silica gel flash chromatography column eluted with 20% ethyl acetate/hexane to afford 0.580 g (86%) of the title compound.

$^1$H NMR (300 MHz, CDCl$_3$, ppm): δ3.75 (s, 3H), 3.80 (s, 3H), 4.35 (s, 2H), 5.65 (s, 1H), 6.80 (s, 1H), 6.95 (s, 1H), 7.30–7.40 (m, 3H), 7.50–7.60 (m, 2H).

FAB-MS: m/e 398,400, 402 (M+1).

Step H

Preparation of
3-[4-((1-Carbomethoxy-1-Phenyl)Methoxy)
-3-Chloro-5-Methoxyphenyl]-Methyl-6-(N-Methyl-N-
Iso -Butyloxycarbonyl)-Amino-2-Propylquinazolin-4(3
H)-One To a half suspension of 80 mg (0.252 mmol) of the product of Step E in 0.5 mL of anhydrous DMF was added 10.6 mg(1.05 eq) of a 60% oil dispersion of sodium hydride and the reaction mixture was stirred under an N$_2$ atmosphere. After stirring 40 minutes at room temperature, a solution of 0.111 g (1.1 eq) of the product of Step G dissolved in 0.5 mL DMF was added to the solution of the anion. The reaction mixture was stirred overnight, then partitioned between water and ethyl acetate. The organic layer was separated, dried (MgSO$_4$), filtered and evaporated in vacuo. The residual oil was purified on a silica gel flash chromatography column eluted with 40% ethyl acetate/hexane to afford 100 mg (63%) of the title compound.

$^1$H NMR (300 MHz, CDCl$_3$, ppm): δ0.84–1.01 (m, 9H), 1.58–2.02 (m, 3H), 2.63–2.68 (t, 2H), 3.38 (s, 3H), 3.71 (s, 3H), 3.73 (s, 3H), 3.91 (d, 2H), 5.20–5.30 (br s, 2H), 5.72 (s, 1H), 6.58–6.64 (m, 1H), 6.68 (d, 1H), 7.28–7.34 (m, 3H), 7.48–7.55 (m, 2H), 7.61 (d, 1H), 7.72 (d, 1H), 8.07 (d, 1H).

FAB-MS: m/e 636, 638 (M+1, 3:1 ratio).

Step I

Preparation of
3-[4-((1-Carboxy-1-Phenyl)-Methoxy)-3-Chloro-5-
Methoxyphenyl]Methyl-6-(N-Methyl-N-Iso
-butyloxycarbonyl)Amino-2-Propylquinazolin-4(3
H)-One To a solution of 97 mg (0.15 mmol) of the product of Step H dissolved in 2 mL of methanol, was added 0.25 mL of a 1N solution of NaOH and the reaction mixture was stirred at room temperature for 2.5 hours. The reaction mixture was then adjusted to pH 6 with 1N HCl, concentrated in vacuo, and the residue was applied to a silica gel flash chromatography column and eluted with CHCl₃/MeOH/NH₄OH (80:15:1). Evaporation of the purified fractions and drying in vacuo afforded 60 mg (63%) of the title compound.

¹H NMR (300 MHz, CDCl₃, ppm): δ0.88–1.06 (m, 9H), 1.68–1.82 (m, 2H), 1.85–2.04 (m, 1H), 2.76 (t, 2H), 3.43 (s, 3H), 3.68 (s, 3H), 3.95 (d, 2H), 5.38 (s, 2H), 5.67 (s, 1H), 6.68 (d, 1H), 6.74 (d, 1H), 7.26–7.33 (m, 3H), 7.48–7.54 (m, 2H), 7.72 (d, 1H), 7.82 (dd, 1H), 8.14 (d, 1H).

EXAMPLE 6

3-[4-((1-Carboxy-1-Phenyl)Methoxy)-3-Propylphenyl]-Methyl-6-(N-Methyl-N-Iso-Butyloxycarbonyl)Amino-2-Propylquinazolin-4(3H)-One

Step A

Preparation of Methyl 4-(2-Propen-1-Yl)-Oxybenzoate

A 2 L flask was equipped with a mechanical stirrer, a reflux condenser and a stopper, then charged with 50.05 g (0.329 mol) of methyl 4-hydroxybenzoate, 960 mL of acetone, 22.50 g (1.625 mol) of anhydrous potassium carbonate, 80.5 mL (112.6 g, 0.932 mol) of allyl bromide and the mixture was stirred and refluxed for 14 hours. The mixture was cooled to room temperature, filtered and concentrated to an oil. The residual oil was purified by distillation (97° C.@0.03 mm Hg) to afford 53.52 g (86%) of the title compound.

¹H NMR (300 MHz, CDCl₃, ppm): δ3.84 (s, 3H), 4.56 (d, J=7 Hz, 2H), 5.28 (dd, J=3,12 Hz, 1H), 5.40 (dd, J=3,19Hz, 1H), 5.96–6.10 (m, 1H), 6.90 (d, J=10 Hz, 2H), 7.96 (d, J=1 0 Hz, 2H).

FAB-MS: m/e 193 (M+1).

Step B

Preparation of Methyl 4-Hydroxy-3-(2-Propen-1-Yl)-Benzoate

A solution of 15.05 g (78.3 mmol) of the product of Step A in 25 mL of 1,2-dichlorobenzene was magnetically stirred and refluxed (183° C.) under an argon atmosphere for 18 hours. At this point, the reaction mixture was cooled to room temperature and applied to a 6 cm diameter by 18 cm silica gel flash chromatography column and eluted with 25% ethyl acetate-hexane to separate the 1,2-dichlorobenzene, then with 40% ethyl acetate-hexane to elute the product. The product fractions were concentrated in vacuo and the residual oil was crystallized from hexane to afford ! 3.70 g (91%) of the title compound.

¹H NMR (300 MHz, CDCl₃, ppm): δ3.42 (d, J=8 Hz, 2H), 3.88 (s, 3H), 5.14–5.20 (m, 2H), 5.48 (s, 1H), 5.94–6.06 (m, 1H), 6.82 (d, J=12 Hz, 1H), 7.80–7.85 (m, 2H).

FAB-MS: m/e 193 (M+1).

Step C

Preparation of Methyl 4-(Tert-Butyldimethyl-Silyloxy)-3-(2-Propen-1-Yl)Benzoate

To a solution of 5.168 g (26.9 mmol) of the product of Step B in 50 mL of dichloromethane was added 4.40 mL (2.95 mmol) of triethylamine, 4.46 g (2.95 mmol) of tert-butyldimethylchlorosilane, 0.100 g of 4-dimethylaminopyridine, and the reaction mixture was stirred at room temperature for 2 hours. The mixture was then diluted with 50 mL dichloromethane, washed with 100 mL 1N hydrochloric acid, dried (MgSO₄), filtered and evaporated. The residual oil (7.993 g, 97%) was used in the next step without further purification.

¹H NMR (300 MHz, CDCl₃, ppm): δ0.24 (s, 6H), 1.02 (s, 9H), 3.36 (d, J=8 Hz, 2H), 3.84 (s, 3H), 4.98–5.08 (m, 2H), 5.88–6.03 (m, 1H), 6.78 (d, J=1 1 Hz, 1H), 7.76–8.40 (m, 2H).

FAB-MS: m/e 307 (M+1).

Step D

Preparation of 4-(Tert-Butyldimethyl-Silyloxy)-3-(2-Propen-1-Yl)Benzyl Alcohol

To a magnetically stirred solution of 8.523 g (28.0 mmol) of the product from Step C in 35 mL of anhydrous THF was added 15.0 mL of a 1.0M solution of lithium aluminum hydride in THF, and the reaction mixture was stirred under a nitrogen atmosphere for 2 hours. At this point, the reaction was quenched by cautious addition of 10 mL water, the resulting precipitate was dissolved by addition of 1.0N is hydrochloric acid and the product was extracted into ethyl acetate. The organic layer was separated, dried (MgSO₄), filtered and evaporated in vacuo to afford 7.258 g (93%) of the title compound.

¹H NMR (300 MHz, CDCl₃, ppm): δ0.20 (s, 6H), 1.00 (s, 9H), 3.34 (d, J=8 Hz, 2H), 3.84 (s, 1H), 4.57 (s, 2H), 4.97–5.07 (m, 2H), 5.88–6.03 (m, 1H), 6.86 (d, J=10 Hz, 1H), 7.05–7.14 (m, 2H).

FAB-MS: m/e 279, 261 (M+1).

Step E

Preparation of 4-Hydroxy-3-(2-Propen-1-Yl)-Benzyl Alcohol

To a solution of approximately 7.26 g (2.6 mmol) of the crude product of Step D, dissolved in 50 mL of anhydrous THF was added 26 mL (2.6 mmol) of tetra-n-butylammonium fluoride and the reaction mixture was stirred at room temperature for 16 hours. The mixture was then evaporated in vacuo and the residual oil was purified on a silica gel flash chromatography column eluted with 5% methanol/chloroform to afford 3.386 g (79%) of the title compound as a colorless oil.

¹H NMR (300 MHz, CDCl₃, ppm): δ2.12 (br s, 1H), 3.35 (d, J=8 Hz, 2H), 4.54 (s, 3H), 5.05–5.15 (m, 2H), 5.90 (br s, 1H), 5.90–6.05 (m, 1H), 6.70 (d, J=10 Hz, 1H), 7.02–7.10 (m, 2H).

FAB-MS: m/e 165 (M+1).

Step F

Preparation of 4-Hydroxy-3-Propylbenzyl Alcohol

To a solution of 0,370 g (2.25 mmol) of the product of Step E dissolved in 25 mL of absolute ethanol was added 53 mg of a 5% rhodium on carbon catalyst and the mixture was shaken under a 40 psig pressure of hydrogen on a Parr apparatus. After 30 minutes, the reaction mixture was removed, filtered and evaporated in vacuo. The residue was purified on a silica gel flash chromatography column eluted with 35% ethyl acetate/hexane to afford the title compound.

¹H NMR (300 MHz, CDCl₃, ppm): δ0.95 (t, J=8 Hz, 3H), 1.55–1.68 (m, 2H), 2.22 (br s, 1H), 2.57 (t, J=8 Hz, 2H), 4.56 (s, 2H), 5.93 (br s, 1H), 6.66 (d, J=10 Hz, 1H), 7.00 (dd, J=2, 10 Hz, 1H), 7.08 (d, J=2 Hz, 1H).

FAB-MS: m/e 167 (M+1).

Step G

Preparation of Methyl (4-Hydroxymethyl-2-Propyl-Phenoxy)-2-Phenylacetate

To a solution of 0.484 g (2.91 mmol) of the product of Step F dissolved in 12 mL of acetone were added 0.667 g (2.91 mmol) of methyl 2-bromophenylacetate, 0.804 g (5.82 mmol) of anhydrous $K_2CO_3$ and the mixture was stirred and heated at reflux for 5 hours. The mixture was then cooled, filtered and evaporated in vacuo. The residual oil was purified on a silica gel flash chromatography column eluted with 30% ethyl acetate/hexane to afford 0.756 g (83%) of the title compound.

$^1$H NMR (300 MHz, $CDCl_3$, ppm): δ0.95 (t, J=8 Hz, 3H), 1.58 (br s, 1H), 1.60–1.75 (m, 2H), 2.70 (t, J=8 Hz, 2H), 3.68 (s, 3H), 4.57 (m, 2H), 5.62 (s, 1H), 6.68 (d, J=10 Hz, 1H), 7.07 (dd, J=2, 10 Hz, 1H), 7.16 (d, J=2 Hz, 1H), 7.32–7.44 (m, 3H), 7.55–7.60 (m, 2H).

FAB-MS: m/e 315 (M+1).

Step H

Preparation of Methyl (4-Bromomethyl-2-Propylphenoxy)-2-Phenylacetate

To a stirred (0° C.) solution of 0.750 g (2.31 mmol) of the product of Step G, and 0.949 g (2.86 mmol) of carbon tetrabromide dissolved in 7 mL of methylene chloride was added 0.751 g of triphenylphosphine (2.86 mmol) in portions. After the addition was complete, the reaction mixture was stirred and allowed to warm to room temperature over 1 hour. The reaction mixture was then evaporated in vacuo, and the residue was purified on a silica gel flash chromatography column eluted with 10% ethyl acetate/hexane to afford 0.703 g (78%) of the title compound.

$^1$H NMR (300 MHz, $CDCl_3$, ppm): δ0.95 (t, J=8 Hz, 3H), 1.60–1.75 (m, 2H), 2.70 (t, J=8 Hz, 2H), 3.69 (s, 3H), 4.44 (s, 2H), 5.62 (s, 1H), 6.64 (d, J=10 Hz, 1H), 7.12 (dd, J=2, 10 Hz, 1H), 7.18 (d, J=2 Hz, 1H), 7.34–7.44 (m, 3H), 7.53–7.58 (m, 2H).

Step I

Preparation of 3-[4-((1-Carboxmethoxy-1-Phenyl)Methoxy)-3-Propyl-phenyl]Methyl-6-(N-Methyl-N-Isobutyloxycarbonyl)Amino-2-Propylquinazolin-4(3 H)-One

To a solution of 115 mg (0.36 mmol) of the product of Step E from Example 5 in 1.5 mL of anhydrous DMF was added 15.0 mg (0.36 mmol) of a 60% oil dispersion of sodium hydride and the reaction mixture was stirred under an $N_2$ atmosphere. After stirring 45 minutes at room temperature, a solution of 0.137 g (0.36 mmol) of the product of Step H dissolved in 0.5 mL DMF was added to the solution of the anion. The reaction mixture was then stirred an additional hour at room temperature, then partitioned between water and ethyl acetate. The organic layer was separated, dried (MgSO_4), filtered and evaporated in vacuo. The residual oil was purified on a silica gel flash chromatography column eluted with 35% ethyl acetate/hexane to afford 0.060 g (49%) of the title compound.

$^1$H NMR (300 MHz, $CDCl_3$, ppm): δ0.85 (d, 6H), 0.92 (t, 3H), 0.96 (t, 3H), 1.55–2.00 (m, 5H), 2.60–2.75 (m, 4H), 3.36 (s, 3H), 3.77 (s, 3H), 3.90 (d, 2H), 5.28 (br s, 2H), 5.57 (s, 1H), 6.63 (d, 1H), 6.85 (dd, 1H), 6.99 (d, 1H), 7.30–7.42 (m, 3H), 7.50–7.60 (m, 2H), 7.55 (dd, 1H), 7.60 (d, 8.08 (d, 1H).

FAB-MS: m/e 6 14 (M+H).

Step J

Preparation of 3-[4-((1-Carboxy-1-Phenyl)-Methoxy)-3-Propyl-phenyl]Methyl-6-(N-Methyl-N-Isobutyloxy-Carbonyl)Amino-2-Propylquinazolin-4(3 H)-One

To a solution of 60 mg (0.098 mmol) of the product of Step I dissolved in 2 mL of methanol, was added 0.25 mL of a 1N solution of NaOH and the reaction mixture was stirred at room temperature for 4 hours. The reaction mixture was then adjusted to pH 7 with 1N HCl, concentrated in vacuo, and the residue was applied to a silica gel flash chromatography column and eluted with 10% $MeOH/CHCl_3$. Evaporation of the purified fractions and drying in vacuo afforded 33 mg (57%) of the title compound.

$^1$H NMR (300 MHz, $CD_3OD$, ppm): δ0.88–1.05 (complex, 12 H), 1.56–1.67 (m 2H), 1.72–1.84 (m, 2H), 1.87–2.00 (m, 1H), 2.55–2.65 (m, 1H). 2.75–2.86 (m, 3H), 3.42 (s, 3H), 3.95 (d, 2H), 5.38 (br s, 2H), 5.43 (s, 1H), 6.85 (d, 1H), 6.94 (dd, 1H), 7.05 (d, 1H), 7.28–7.38 (m, 3H), 7.62–7.70 (m, 2H), 7.71 (d, 1H), 7.83 (dd, 1H), 8.15 (d, 1H).

FAB-MS: m/e 600 (M+H).

EXAMPLE 7

2-Butyl-3-[4-(1-Carboxy-1-Phenyl)Methoxy-3,5-Dipropylphenyl]Methyl-6-Methylquinazolin-4(3 H)-One

Step A

Preparation of Methyl 2-(2,6-Dipropyl-4-Hydroxymethyl-Phenoxy)Phenylacetate

To a solution of 1.014 g (4.87 mmol) of 2,6-di-propyl-4-hydroxymethylphenol dissolved in 10 mL of anhydrous dimethylformamide was added 2.379 g of cesium carbonate and the reaction mixture was stirred under a nitrogen atmosphere at room temperature for 1 hour. A solution of methyl cx-bromo-phenylacetate dissolved in 2 mL DMF was added and the reaction mixture was stirred at 60° C. overnight. The reaction mixture was cooled to room temperature and partitioned between water and EtOAc. The organic layer was washed with brine, separated, dried (MgSO_4), filtered and evaporated. The residual oil was purified on a silica gel flash chromatography column eluted with 20% EtOAc-hexane and combination of the purified fractions afforded 0.598 g (35%) of the title compound.

$^1$H NMR (300 MHz, $CDCl_3$, ppm): δ0.78 (t, J=7.6 Hz, 6H), 1.46–1.56 (m, 4H), 1.68 (br s, 1H), 2.34–2.40 (m, 4H), 3.73 (s, 3H), 4.56 (s, 2H), 5.09 (s, 1H), 6.98 (s, 2H), 7.35–7.37 (m , 3H), 7.46–7.50 (m, 2H).

Step B

Preparation of Methyl 2-(2,6-Dipropyl-4-Bromomethyl-Phenoxy)Phenylacetate

To a solution of 2.66.1 g (7.46 mmol) of the product of Step A dissolved in 15 mL of carbon tetrachloride was added 0.709 mL (7.47 mmol) of phosphorous tribromide and the reaction mixture was magnetically stirred at room temperature for 30 min as hydrogen bromide was evolved. The magnetic stir bar was removed, and the reaction mixture was concentrated in vacuo. The residue was redissolved and evaporated from carbon tetrachloride several times to remove most of the hydrogen bromide. Finally, the residue was purified by rapid flash chromatography on a silica gel column eluted with 10% EtOAc-hexane. Combination and evaporation of the purified fractions and drying in vacuo afforded 2.129 (68%) of the title compound which was used directly in the next step without further characterization.

Step C

Preparation of
2-Butyl-3-[4-(1-Methoxycarbonyl-1-Phenyl)Methoxy-3,5-Dipropylphenyl]Methyl-6-Methylquinazolin-4(3 H)-One An oven dried 100 mL round bottom flask equipped with a magnetic stir bar and a septum was charged with 3.227 g (14.9 mmol) of 2-n-butyl-6-methylquinazolin-4(1H)-one, and 60 mL of anhydrous dimethylformamide was added. Sodium hydride (0.656 g of a 60% oil dispersion, 16.4 mmol) was added and the reaction mixture was stirred under a nitrogen atmosphere as hydrogen was evolved. After 45 min, a solution of 6.256 g (14.9 mmol) of the product of Step B dissolved in 5 mL DMF was added to the clear solution of the deprotonated quinazolinone and the reaction mixture was then stirred for two hours at room temperature. The reaction mixture was then partitioned between water and EtOAc, and the organic layer was separated, washed with brine, dried (MgSO4), filtered and evaporated. The residual oil was purified on a silica gel flash chromatography column eluted with 15% EtOAc-hexane to afford 4.717 g (57%) of the title compound.

$^1$H NMR (300 MHz, CDCl$_3$, ppm): δ0.73 (t, J=7.20 Hz, 6H), 0.87 (t, J=7.20 Hz, 3H), 1.34–1.48 (m, 6H), 1.69 (m, 2H), 2.24–2.31 (m, 4H), 2.64 (s, 3H), 2.69 (t, J=8.00 Hz, 2H), 3.70 (s, 3H), 5.05 (s, 1H), 5.27 (br s, 2H), 6.75 (s, 2H), 7.33–7.35 (m, 3H), 7.44–7.47 (m, 2H), 7.54 (s, 2H), 8.08 (s, 1H).

Step D

Preparation of
2-Butyl-3-[4-(1-Carboxy-1-Phenyl)Methoxy-3,5-Dipropylphenyl]Methyl-6-Methylquinazolin-4(3 H)-One A 100 mL round bottom flask equipped with a magnetic stirrer was charged with a solution of 8.296 g (14.9 mmol) of the product of Step C in 20 mL of THF and then diluted with 30 mL of methanol. To this solution was added 5.0 mL of a 5.0N solution of sodium hydroxide and the reaction mixture was stirred at room temperature and periodically monitored by TLC (CHCl$_3$-MeOH-NH$_4$OH; 80:15:1). After 3 hours 12.5 mL of a 2.0N solution of hydrochloric acid was added in 1 mL aliquots with stirring to provide a heavy precipitate of the product suspended in pH=6.5 medium. The product was partitioned between saturated brine and THF. The THF layer was separated, washed with brine, dried (Na$_2$SO$_4$), filtered through a 0.45 micron filter, and evaporated in vacuo. The residue was then recrystallized twice from THF-hexane and dried in a vacuum oven to afford 7.197 g (89%) of the title compound.

$^1$H NMR (300 MHz, CD3OD, ppm): δ0.74 (t, J=7.60 Hz, 6H), 0.87 (t, J=7.60 Hz, 3H), 1.32–1.45 (m, 6H), 1.62–1.67 (m, 2H), 2.32 (t, J=7.60 Hz, 4H), 2.74–2.77 (t, J=8.40 Hz, 2H), 5.05 (s, 1H), 5.36 (br s, 2H), 6.80 (s, 2H), 7.36–7.38 (m, 3H), 7.45–7.48 (m, 2H), 7.57 (d, J=8.40 Hz, 1H), 7.66 (dd, J=8.40, 2.00 Hz, 1H), 8.03 (s, 1H).

FAB-MS: m/e 541 (M+H).

EXAMPLE 8

2-Butyl-3-[4-(1-Carboxy-1-(3-Methylphenyl))Methoxy-3,5-Dipropylphenyl]Methyl-6-Methylquinazolin-4(3 H)-One Step A Preparation of Ethyl α-Bromo-3′-Methylphenylacetate To a magnetically stirred solution of 7.20 g (37.1 mmol) of ethyl 3′-methylmandelate and 18.5 g (55.7 mmol) of carbon tetrabromide in 30 mL of methylene chloride was added 14.6 g (55.7 mmol) of triphenylphosphine in portions at 0° C. The reaction mixture was stirred and allowed to slowly warm to room temperature over two hours. The reaction mixture was then evaporated in vacuo and adsorbed onto a silica gel flash chromatography column which was then eluted with 5% EtOAc-hexane. Evaporation of the purified fractions and drying in vacuo afforded 6.90 g (72%) of the title compound.

$^1$H NMR (200 MHz, CDCl$_3$, ppm): δ1.27 (t, J=7.0 Hz, 3H), 2.35 (s, 3H), 4.10–4.32 (m, 2H), 5.31 (s, 1H), 7.12–7.38 (m, 4H).

FAB-MS: m/e 258 (M+H).

Step B

Preparation of Ethyl 2-(2,6-Dipropyl-4-Hydroxymethyl Phenoxy)-2-(3-Methylphenyl)Acetate To a solution of 2.44 g (11.7 mmol) of 2,6-dipropyl-4-hydroxymethylphenol in 10 mL of DMF was added 4.76 g (14.6 mmol) of cesium carbonate, a solution of 3.00 g (11.7 mmol) of the product of Step A dissolved in 10 mL of DMF, and the reaction mixture was stirred and heated at 60° C. overnight. The reaction was then cooled to room temperature and partitioned between EtOAc and water. The organic layer was separated, washed with saturated brine, dried (MgSO$_4$), filtered and evaporated in vacuo. The residue was purified on a silica gel flash chromatography column eluted with 20% EtOAc-hexane. Evaporation of the purified fractions and drying in vacuo afforded 2.93 g (65%) of the title compound.

$^1$H NMR (300 MHz, CDCl$_3$, ppm): δ0.79 (t, J=7.20 Hz, 6H), 1.21 (t, J=7.20 Hz, 3H), 1.40–1.52 (m, 4H), 2.30–2.38 (m, 4H), 2.35 (s, 3H), 2.55 (t, J=5.20 Hz, 1H), 4.10–4.28 (m, 2H), 4.56 (d, J=5.20 Hz, 2H), 5.02 (s, 1H), 6.97 (s, 2H), 7.14–7.16 (m, 1H), 7.21–7.26 (m, 2H), 7.33 (s, 1H).

Step C

Preparation of Ethyl 2-(2,6-Dipropyl-4-Bromomethyl-Phenoxy)-2-(3-Methylphenyl)Acetate To a solution of 2.03 g (5.29 mmol) of the product of Step B dissolved in 10 mL of carbon tetrachloride was added 0.50 mL (5.29 mmol) of phosphorous tribromide and the reaction mixture was magnetically stirred at room temperature for 1 hour as hydrogen bromide was evolved. The magnetic stir bar was removed, and the reaction mixture was concentrated in vacuo. The residue was redissolved and evaporated from methylene chloride three times to remove most of the hydrogen bromide. Finally, the residue was purified by rapid flash chromatography on a silica gel column eluted with 20% EtOAc-hexane. Combination and evaporation of the purified fractions in vacuo afforded 2.27 (96%) of the title compound.

¹H NMR (300 MHz, CDCl₃, ppm): δ0.79 (t, J=7.20 Hz, 6H), 1.21 (t, J=7.20 Hz, 3H), 1.38–1.52 (m, 4H), 2.25–2.38 (m, 4H), 2.33 (s, 3H), 4.10–4.28 (m, 2H), 4.41 (s, 2H), 5.03 (s, 1H), 6.99 (s, 2H), 7.14–7.17 (m, 1H), 7.22–7.28 (m, 2H), 7.32 (s, 1H).

Step D

Preparation of 2-Butyl-3-[4-(1-Methoxycarbonyl-1-(3-Methylphenyl)-)Methoxy-3,5-Dipropylphenyl]Methyl-6-Methyl-quinazolin-4(3 H)-One To a suspension of 0.076 g (0.35 mmol) of 2-n-butyl-6-methylquinazolin-4(1H)-one in 2.0 mL of DMF was added 14 mg (0.35 mmol) of a 60% oil dispersion of sodium hydride and the reaction mixture was stirred at room temperature under a nitrogen atmosphere for 30 minutes. A solution of 0.152 g (0.34 mmol) of the product of Step C dissolved in 1 mL of DMF was added and the reaction mixture was stirred at room temperature for an additional 2 hours. The mixture was then partitioned between EtOAc and water, the organic layer was separated, dried (MgSO₄), filtered and evaporated. The residue was purified on a silica gel flash chromatography column eluted with 20% EtOAc-hexane. Evaporation of the purified fractions and drying in vacuo afforded 0.102 g (51%) of the title compound.

¹H NMR (300 MHz, CDCl₃, ppm): δ0.74 (t, J=7.20 Hz, 6H), 0.88 (t, J=7.20 Hz, 3H), 1.21 (t, J=7.20 Hz, 3H), 1.31–1.48 (m, 6H), 1.65–1.73 (m, 2H), 2.25–2.31 (m, 4H), 2.34 (s, 3H), 2.47 (s, 3H), 2.69–2.76 (m, 2H), 4.08–4.25 (m, 2H), 4.99 (s, 1H), 5.29 (br s, 2H), 6.75 (s, 2H), 7.14–7.26 (m, 3H), 7.28 (s, 1H), 7.56 (br s, 2H), 8.09 (s, 1H).

Step E

Preparation of 2-Butyl-3-[4-(1-Carboxy-1-(3-Methylphenyl))Methoxy-3,5-Dipropylphenyl]Methyl-6-Methyl-quinazolin-4(3 H)-One To a magnetically stirred solution of 0.055g (0.09 mmol) of the product of Step D in 2 mL methanol was added 0.5 mL of a 5.0N solution of sodium hydroxide and the reaction was stirred at room temperature for 5 hours. The reaction mixture was adjusted to pH=6 with 2.0N hydrochloric acid and then partitioned between EtOAc and hexane. The organic layer was separated, washed with saturated brine, dried (MgSO₄), filtered, and evaporated. The residue was then purified on a silica gel flash chromatography column eluted with CHCl₃-MeOH-NH₄OH (80:15:1). Evaporation of the purified fractions and drying in vacuo afforded 0.028 g (55%) of the title compound.

¹H NMR (300 MHz, CD₃OD, ppm): δ0.74 (t, J=7.20 Hz, 6H), 0.87 (t, J=7.20 Hz, 3H), 1.28–1.50 (m, 6H), 1.60–1.68 (m, 2H), 2.28–2.34 (m, 4H), 2.31 (s, 3H), 2.49 (s, 3H), 2.75 (t, J=8.00 Hz, 2H), 4.91 (s, 1H), 5.36 (br s, 2H), 6.78 (s, 2H), 7.12–7.23 (m, 3H), 7.29 (br s, 1H), 7.56 (d, J=8.00 Hz, 1H), 7.65 (dd, J=8.00, 2.40 Hz, 1H), 8.03 (d, J=2.40 Hz, 1H).

EXAMPLE 9

2-Butyl-3-[4-(1-Carboxy-1-(3-Chlorophenyl))Methoxy-3,5-Dipropylphenyl]Methyl-6-Methylquinazolin-4(3 H)-One

Step A

Preparation of Methyl α-bromo-3-Chlorophenylacetate

A 250 mL round bottom flask equipped with a magnetic stirrer and a reflux condenser was charged with 17.06 g (0.10 mol) of 3-chlorophenylacetic acid, 10 mL of carbon tetrachloride, and 28.5 mL of thionyl chloride and then the reaction mixture was stirred and heated at 65° C. for 30 minutes. The reaction mixture was then cooled to room temperature and 21.4 g of powdered N-bromosuccinimide, 50 mL of carbon tetrachloride, and 7 drops of 48% aqueous hydrogen bromide were successively added. The reaction mixture was then heated to 70° C. for 10 minutes, and then to 85° C. for 1.5 hours. The reaction was then recooled to room temperature and the excess carbon tetrachloride and thionyl chloride were removed in vacuo. The residue was dissolved in carbon tetrachloride and filtered, and the filtrate was slowly treated with excess methanol in a flask equipped with a reflux condenser. After the exothermic reaction subsided, the reaction mixture was evaporated in vacuo and then purified by filtration through a 4 inch thick layer of silica gel eluted with 10% EtOAc-hexane. The filtrate was evaporated to afford an oil which was further purified by Kugelrohr distillation to afford 22.710 g (86%) of the title compound.

¹H NMR (300 MHz, CDCl₃, ppm): δ3.78 (s, 3H), 5.28 (s, 1H), 7.25–7.32 (m, 3H), 7.54 (br s, 1H).

Step B

Preparation of Methyl 2-(2,6-Dipropyl-4-Hydroxymethylphenoxy)-2-(3-Chlorophenyl)Acetate To a solution of 1.029 g (4.94 mmol) of 2,6-dimethyl-4-hydroxymethylphenol dissolved in 10 mL of DMF was added 0.217 g (5.43 mmol) of a 60% oil dispersion of sodium hydride and the reaction mixture was stirred at room temperature for 1 hour. A solution of 1.423 g (5.43 mmol) of the product of Step A dissolved in 1 mL of DMF was added and the reaction mixture was stirred an additional 2 hours at room temperature. The reaction mixture was then partitioned between EtOAc and water, extracted, dried (MgSO₄), filtered and evaporated. The residue was purified on a silica gel flash chromatography column eluted with 20% EtOAc-hexane to afford 1.133 g (59%) of the title compound.

¹H NMR (300 MHz, CDCl₃, ppm): δ0.81 (t, J=7.60 Hz, 6H), 1.40–1.56 (m, 4H), 2.30–2.44 (m, 4H), 3.73 (s, 3H), 4.56 (s, 2H), 5.06 (s, 1H), 6.97 (s, 2H), 7.27–7.38 (m, 3H), 7.53 (t, J=1.6 Hz, 1H).

Step C

Preparation of Methyl 2-(2,6-Dipropyl-4-Bromomethylphenoxy)-2-(3-Chlorophenyl)Acetate To a solution of 1.133 g (0.29 mmol) of the product of Step B dissolved in 10 mL of carbon tetrachloride was added 0.138 mL (1.45 mmol) of phosphorous tribromide and the reaction mixture was magnetically stirred at room temperature for 30 min as hydrogen bromide was evolved. The magnetic stir bar was removed, and the reaction mixture was concentrated in vacuo. The residue was redissolved and evaporated from carbon tetrachloride several times to remove most of the hydrogen bromide. Finally, the residue was purified by rapid flash chromatography on a silica gel column eluted with 10% EtOAc-hexane. Combination and evaporation of the purified fractions in vacuo afforded 1.063 (81%) of the title compound.

$^1$H NMR (300 MHz, CDCl$_3$, ppm): δ0.81 (t, J=7.2 Hz, 6H), 1.40-1.57 (m, 4H), 2.28-2.34 (M, 4H), 3.73 (s, 3H), 4.40 (s, 2H), 5.07 (s, 1H), 7.01 (s, 2H), 7.26-7.38 (m, 3H), 7.54 (t, J=1.6 Hz, 1H).

Step D

Preparation of
2-Butyl-3-[4-(1-Methoxycarbonyl-1-(3-Chlorophenyl)-
)Methoxy-3,5-Dipropylphenyl]Methyl-6-Methyl-
quinazolin-4(3 H)-One To a suspension of 0.074 g (0.34 mmol) of 2-n-butyl-6-methylquinazolin-4(1H)-one in 1.4 mL of DMF was added 15 mg of a 60% oil dispersion of sodium hydride and the reaction mixture was stirred with a magnetic stirrer under a nitrogen atmosphere for 45 minutes. The product of Step C (0.186 g, 0.41 mmol) dissolved in 0.5 mL of DMF was then added to the reaction mixture and stirring was continued for an additional 2 hours at room temperature. The reaction mixture was then partitioned between EtOAc and hexane, separated, washed with saturated brine, dried (MgSO$_4$), filtered and evaporated. The residue was purified on a silica gel flash chromatography column eluted with 15% EtOAc-hexane to afford 0.127 g (63%) of the title compound.

$^1$H NMR (300 MHz, CDCl$_3$, ppm): δ0.75 (t, J=7.60 Hz, 6H), 0.87 (t, J=7.20 Hz, 3H), 1.32-1.48 (m, 6H), 1.65-1.73 (m, 2H), 2.24-2.38 (m, 4H), 2.46 (s, 3H), 2.69 (t, J=8.40 Hz, 2H), 3.71 (s, 3H), 5.02 (s, 1H), 5.27 (br s, 2H), 6.76 (s, 2H), 7.24-7.36 (m, 3H), 7.51 (t, J=1.6 Hz, 1H), 7.54 (s, 2H), 8.07 (s, 1H).

FAB-MS: m/e 589 (M+H).

Step E

Preparation of 2-Butyl-3-[4-(1
-Carboxy-1-(3-Chlorophenyl))
Methoxy-3,5-Dipropylphenyl]Methyl-6-Methyl-
quinazolin-4(3H)-One To a magnetically stirred solution of 0.127 g (0.22 mmol) of the product of Step D in 2 mL methanol was added 0.5 mL of a 5.0N solution of sodium hydroxide and the reaction was stirred at room temperature for 3 hours. The reaction mixture was adjusted to pH=6 with 2.0N hydrochloric acid and then partitioned between EtOAc and hexane. The organic layer was separated, washed with saturated brine, dried (MgSO$_4$), filtered, and evaporated. The residue was then purified on a silica gel flash chromatography column eluted with CHCl$_3$—MeOH—NH$_4$OH (80:15:1). Evaporation of the purified fractions and drying in vacuo afforded 0.102 g (82%) of the title compound.

$^1$H NMR (300 MHz, CD$_3$OD, ppm): δ0.76 (t, J=7.20 Hz, 6H), 0.87 (t, J=7.20 Hz, 3H), 1.27-1.38 (m, 4H), 1.42-1.52 (m, 2H), 1.60-1.68 (m, 2H), 2.30-2.36 (m, 4H), 2.49 (s, 3H), 2.75 (t, J=8.40 Hz, 2H), 4.87 (s, 1H), 5.36 (br s, 2H), 6.79 (s, 2H), 7.28-7.37 (m, 3H), 7.52 (br s, 1H), 7.56 (d, J=8.40 Hz, 1H), 7.65 (dd, J=8.40, 2.00 Hz, 1H), 8.02 (d, J=2.00 Hz, 1H).

FAB-MS: m/e 575 (M+H).

EXAMPLE 10

3-[4-(1-Carboxy-1
-(3-Chlorophenyl))Methoxy-3,5-Dipropylphenyl]-
Methyl-2-Propyl-6-(Prop-2-Yl)Quinazolin-4(3H)-One

Step A

Preparation of
3-[4-(1-Methoxycarbonyl-1-(3-Chlorophenyl))
Methoxy-3,5-Dipropylphenyl]Methyl-2-Propyl-6-
(Prop-2-Yl)Quinazolin-4(3 H)-One To a suspension of 0.070 g (0.30 mmol) of 2-propyl-6-(prop-2-yl)quinazolin-4(1H)-one in 1.3 mL of DMF was added 13 mg of a 60% oil dispersion of sodium hydride and the reaction mixture was stirred with a magnetic stirrer under a nitrogen atmosphere for 45 minutes. The product of Step C in Example 9 (0.166 g, 0.37 mmol) dissolved in 0.5 mL of DMF was then added to the reaction mixture and stirring was continued for an additional 2 hours at room temperature. The reaction mixture was then partitioned between EtOAc and hexane, separated, washed with brine, dried (MgSO$_4$), filtered and evaporated. The residue was purified on a silica gel flash chromatography column eluted with 15% EtOAc-hexane to afford 0.108 g (59%) of the title compound.

$^1$H NMR (300 MHz, CDCl$_3$, ppm): δ0.76 (t, J=7.20 Hz, 6H), 0.94 (t, J=7.20 Hz, 3H), 1.30 (d, J=6.80 Hz, 6H), 1.34-1.48 (m, 4H), 1.70-1.78 (m, 2H), 2.25-2.38 (m, 4H), 2.68 (t, J=8.00 Hz, 2H), 3.04 (s, J=6.80 Hz, 1H), 3.71 (s, 3H), 5.03 (s, 1H), 5.28 (br s, 2H), 6.77 (s, 2H), 7.26-7.36 (m, 3H), 7.51 (t, J=2.00 Hz, 1H), 7.58 (d, J=8.40 Hz, 1H), 7.62 (dd, J=8.40, 2.00 Hz, 1H), 8.12 (d, J=2.00 Hz, 1H).

FAB-MS: m/e 603 (M+H).

Step B

Preparation of 3-[4-(1-Carboxy-1-(3-Chloro-Phenyl))
-Methoxy-3,5-Dipropylphenyl]Methyl-2-Propyl-6-
(Prop-2-Yl)Quinazolin-4(3H)-One To a magnetically stirred solution of 0.108 g (0.18 mmol) of the product of Step A in 1.5 mL methanol was added 0.5 mL of a 5.0N solution of sodium hydroxide and the reaction was stirred at room temperature for 3 hours. The reaction mixture was adjusted to pH=6 with 2.0N hydrochloric acid and then partitioned between EtOAc and hexane. The organic layer was separated, washed with saturated brine, dried (MgSO$_4$), filtered, and evaporated. The residue was then purified on a silica gel flash chromatography column eluted with CHCl$_3$—MeOH—NH$_4$OH (80:15:1). Evaporation of the purified fractions and drying in vacuo afforded 0.083 g (79%) of the title compound.

$^1$H NMR (300 MHz, CD3OD, ppm): 8 0.76 (t, J=7.60 Hz, 6H), 0.93 (t, J=7.20 Hz, 3H), 1.32 (d, J=7.20 Hz, 6H), 1.32-1.50 (m, 4H), 1.65-1.73 (m 2H), 2.28-2.36 (m, 4H),-2.73 (t, J=7.60 Hz, 2H), 3.07 (s, J=7.20 Hz, 1H), 4.96 (s, 1H), 5.36 (br s, 2H), 6.81 (s, 2H), 7.31-7.38 (m, 3H), 7.53 (br s, 1H), 7.59 (d, J=8.40 Hz, 1H), 7.72 (dd, J=8.40, 2.00 Hz, 1H), 8.07 (d, J=2.00 Hz, 1H).

FAB-MS: m/e 589 (M+H).

EXAMPLE 11

2-Butyl-3-[4-(1-Carboxy-1-(3-Chlorophenyl))Methoxy-3,5-Dimethylphenyl]Methyl-6-Methylquinazolin-4(3H)-One

Step A

Preparation of Methyl 2-(2,6-Dimethyl-4-Formylphenoxy)-2-(3-Chlorophenyl)Acetate To a solution of 0.600 g (4.0 mmol) of 3,5-dimethyl-4-hydroxybenzaldehyde in 16 mL acetone was added 1.26 g (4.8 mmol) of the product of Step A in Example 9 and 1.10 g (8.0 mmol) of potassium carbonate. The reaction mixture stirred and heated at reflux for 3.5 hours and then cooled to room temperature. The reaction mixture was then filtered, concentrated in vacuo and the residue was purified on a silica gel flash chromatography column eluted with 30% EtOAc-hexane. Evaporation of the purified fractions and drying in vacuo afforded 1.260 g (95%) of the title compound.

$^1$H NMR (300 MHz, CDCl$_3$, ppm): a 2.20 (s, 6H), 3.74 (s, 3H), 5.28 (s, 3H), 7.30–7.39 (m, 3H), 7.51 (br s, 3H), 9.85 (s, 1H).

EI-MS: m/e 332 (M+).

Step B

Preparation of Methyl 2-(2,6-Dimethyl-4-Hydroxymethyl-Phenoxy)-2-(3-Chlorophenyl)Acetate To a magnetically solution of 1.26 g (3.8 mmol) of the product of Step A in 8 mL of methanol was added 0.072 g (1.9 mmol) of sodium borohydride at 0° C. After stirring for 10 minutes, the reaction mixture was partitioned between EtOAc and water. The organic layer was separated, dried (MgSO$_4$), filtered and evaporated. The residue was purified on a silica gel flash chromatography column eluted with 30% EtOAc-hexane. Combination of the purified fractions and drying in vacuo afforded 0.790 g (63%) of the title compound.

$^1$H NMR (300 MHz, CDCl$_3$, ppm): δ1.53 (br s, 1H), 2.10 (s, 6H), 3.73 (s, 3H), 4.55 (s, 2H), 5.15 (s, 1H), 6.96 (s, 2H), 7.28–7.38 (m, 3H), 7.50 (br s, 1H).

EI-MS: m/e 334 (M+).

Step C

Preparation of Methyl 2-(2,6-Dimethyl-4-Bromomethyl-Phenoxy)-2-(3-Chlorophenyl)Acetate To a solution of 0.560 g (1.62 mmol) of the product of Step B dissolved in 5 mL of carbon tetrachloride was added 0.154 mL (1.6 mmol) of phosphorous tribromide and the reaction mixture was stirred at room temperature for 15 minutes. Carbon tetrachloride was evaporated from the reaction mixture several times to remove the hydrogen bromide, then the residue was purified on a silica gel flash chromatography column eluted with 5% EtOAc-hexane. The purified fractions were evaporated in vacuo affording 0.523 g (81%) of the title compound.

$^1$H NMR (300 MHz, CDCl$_3$, ppm): δ2.09 (s, 6H), 3.73 (s, 3H), 4.38 (s, 2H), 5.15 (s, 1H), 6.99 (s, 2H), 7.28–7.38 (m, 3H), 7.51 (br s, 1H).

EI-MS: m/e 396, 398 (M+).

Step D

Preparation of 2-Butyl-3-[4-(1-Methoxycarbonyl-1-(3-Chlorophenyl)-)Methoxy-3,5-Dimethylphenyl]Methyl-6-(2-Propyl)-Quinazolin-4(3H)-One To a suspension of 0.109 g (0.51 mmol) of 2-n-butyl-6-methylquinazolin-4(1H)-one in 7 mL anhydrous DMF was added 20.2 mg (0.51 mmol) of a 60% oil dispersion of sodium hydride and the reaction mixture was stirred under a nitrogen atmosphere at room temperature for 30 minutes. A solution of 0,200 g (0.50 mmol) of the product of Step C in 3.8 mL of DMF was added and the reaction was stirred an additional 1 hour. The reaction mixture was partitioned between EtOAc and water, separated, dried (MgSO$_4$), filtered and evaporated. The residue was purified on a silica gel flash chromatography column eluted with 15% EtOAc-hexane. Evaporation of the purified fractions and drying in vacuo afforded 0.160 g (59%) of the title compound.

$^1$H NMR (300 MHz, CDCl$_3$, ppm): δ0.88 (t, J=7.60 Hz, 3H), 1.33–1.42 (m, 2H), 1.66–1.74 (m, 2H), 2.03 (s, 6H), 2.46 (s, 3H), 2.69 (t, J=8.00 Hz, 2H), 3.72 (s, 3H), 5.11 (s, 1H), 5.26 (br s, 2H), 6.73 (s, 2H), 7.26–7.35 (m, 3H), 7.47 (t, J=1.60 Hz, 1H), 7.55 (s, 2H), 8.07 (s, 1H).

FAB-MS: m/e 533 (M+1).

Step E

Preparation of 2-Butyl-3-[4-(1-Carboxy-1-(3-Chlorophenyl))Methoxy-3,5-Dimethylphenyl]Methyl-6-(2-Propyl)-Quinazolin-4(3H)-One To a magnetically stirred solution of 0.155 g (0.29 mmol) of the product of Step D in 3.0 mL methanol was added 0.5 mL of a 5.0N solution of sodium hydroxide and the reaction was stirred at room temperature for 3 hours. The reaction mixture was adjusted to pH=6 with 2.0N hydrochloric acid and then partitioned between EtOAc and hexane. The organic layer was separated, washed with saturated brine, dried (MgSO$_4$), filtered, and evaporated. The residue was then purified on a silica gel flash chromatography column eluted with CHCl$_3$-MeOH-NH$_4$OH (80:15:1). Evaporation of the purified fractions and drying in vacuo afforded 0.145 g (96%) of the title compound.

$^1$H NMR (300 MHz, CD$_3$OD, ppm): δ0.88 (t, J=7.60 Hz, 3H), 1.32–1.39 (m, 2H), 1.61–1.67 (m, 2H), 2.00 (s, 6H), 2.49 (s, 3H), 2.75 (t, J=8.00 Hz, 2H), 4.99 (s, 1H), 5.33 (br s, 2H), 6.76 (s, 2H), 7.28–7.35 (m, 3H), 7.47 (s, 1H), 7.56 (d, J=8.00 Hz, 1H), 7.65 (dd, J=8.00, 1.60 Hz, 1H), 8.01 (d, J=1.60 Hz, 1H).

FAB-MS: m/e 519 (M+1).

EXAMPLE 12

2-Butyl-3-[4-(1-Carboxy-1-(3-Chlorophenyl))Methoxy-3-(2-Propyl)Phenylmethyl-6-Methylquinazolin-4(3H)-One

Step A

Preparation of Methyl 2-(2-(2-Propyl)-4-Hydroxymethyl-Phenoxy)-2-(3-Chlorophenyl)Acetate To a solution of 0.200 g (1.2 mmol) of 2-i-propyl-4-hydroxymethylphenol in 3.5 mL acetone was added 0.350 g (1.3 mmol) of the product of Step A in Example 9 and 0.333 g (2.4 mmol) of potassium carbonate. The reaction mixture stirred and heated at gentle reflux overnight. The reaction mixture was then cooled to room temperature, filtered, concentrated in vacuo and the residue was purified on a silica gel flash chromatography column eluted with 20% EtOAc-hexane. Evaporation of the purified fractions and drying in vacuo afforded 0.114 g (27%) of the title compound.

$^1$H NMR (300 MHz, CDCl$_3$, ppm): δ1.23 (d, J=6.80 Hz, 3H), 1.29 (d, J=6.80 Hz, 3H), 3.47 (s, J=6.80 Hz, 1H), 3.71 (s, 3H), 4.60 (s, 2H), 5.61 (s, 1H), 6.66 (d, J=8.40 Hz, 1H), 7.08 (dd, J=8.40, 2.00 Hz, 1H), 7.25 (d, J=2.00 Hz, 1H), 7.32-7.34 (m, 2H), 7.45-7.48 (m, 1H), 7.58 (s, 1H).

EI-MS: m/e 348 (M+).

Step B

Preparation of Methyl 2-(2-(2-Propyl)-4-Bromomethyl -Phenoxy)-2-(3-Chlorophenyl)Acetate To a solution of 0.110 g (0.31 mmol) of the product of Step A dissolved in 1.0 mL of carbon tetrachloride was added 0.03 mL (1.6 mmol) of phosphorous tribromide and the reaction mixture was stirred at room temperature for 10 minutes. Carbon tetrachloride was evaporated from the reaction mixture several times to remove the hydrogen bromide, then the residue was purified on a silica gel flash chromatography column eluted with 15% EtOAc-hexane. The purified fractions were evaporated in vacuo affording 0.104 g (80%) of the title compound.

$^1$H NMR (300 MHz, CDCl$_3$, ppm): δ1.23 (d, J=6.80 Hz, 3H), 1.29 (d, J=6.80 Hz, 3H), 3.44 (s, J=6.80 Hz, 1H), 3.71 (s, 3H), 4.96 (s, 2H), 5.59 (s, 1H), 6.62 (d, J=8.40 Hz, 1H), 7.11 (dd, J=8.40, 2.00 Hz, 1H), 7.25 (d, J=2.00 Hz, 1H), 7.32-7.34 (m, 2H), 7.44-7.46 (m, 1H), 7.56 (s, 1H).

FAB-MS: m/e 411, 413 (M+1).

Step C

Preparation of 2-Butyl-3-[4-(1-Carbomethoxy-1 -(3-Chlorophenyl))Methoxy -3-(2-Propyl)Phenyl]Methyl-6-Methylquinazolin -4(3H)-One To a suspension of 0.050 g (0.23 mmol) of 2-n-butyl-6-methylquinazolin-4(1H)-one in 1.5 mL anhydrous DMF was added 9.7 mg (0.24 mmol) of a 60% oil dispersion of sodium hydride and the reaction mixture was stirred under a nitrogen atmosphere at room temperature for 3 hours. A solution of 0.098 g (0.24 mmol) of the product of Step B in 0.5 mL of DMF and 0.5 mL THF was added and the reaction was stirred an additional 3 hours at room temperature. The reaction mixture was partitioned between EtOAc and water, separated, dried (MgSO$_4$), filtered and evaporated. The residue was purified on a silica gel flash chromatography column eluted with 25% EtOAc-hexane. Evaporation of the purified fractions and drying in vacuo afforded 0.031 g (25%) of the title compound.

$^1$H NMR (300 MHz, CDCl$_3$, ppm): a 0.88 (t, J=7.20 Hz, 3H), 1.19 (d, J=6.80 Hz, 3H), 1.25 (d, J=6.80 Hz, 3H), 1.33-1.42 (m, 2H), 1.67-1.75 (m, 2H), 2.46 (s, 3H), 2.71 (t, J=8.40 Hz, 2H), 3.42 (s, J=6.80 Hz, 1H), 3.68 (s, 3H), 5.30 (br s, 2H), 5.54 (s, 1H), 6.56 (d, J=8.40 Hz, 1H), 6.81 (dd, J=8.40, 2.40 Hz, 1H), 7.11 (d, J=2.40 Hz, 1H), 7.28-7.33 (m, 2H), 7.41-7.44 (m, 1H), 7.51-7.54 (m, 3H), 8.06 (s, 1H).

FAB-MS: m/e 547 (M+1).

Step D

Preparation of 2-Butyl-3-[4-(1-Carboxy-1-(3-Chlorophenyl))Methoxy -3-(2-Propyl)Phenyl]Methyl-6-Methylquinazolin- 4(3H)-One To a magnetically stirred solution of 0.031 g (0.06 mmol) of the product of Step C in 1.0 mL methanol was added 0.2 mL of a 5.0N solution of sodium hydroxide and the reaction was stirred at room temperature overnight. The reaction mixture was adjusted to pH=6 with 1.0N hydrochloric acid and then concentrated in vacuo. The residue was then purified on a silica gel flash chromatography column eluted with CHCl$_3$-MeOH-NH$_4$OH (80:15:1). Evaporation of the purified fractions and drying in vacuo afforded 0.027 g (90%) of the title compound.

$^1$H NMR (300 MHz, CD3OD, ppm): a 0.88 (t, J=7.20 Hz, 3H), 1.11 (d, J=6.80 Hz, 3H), 1.22 (d, J=6.80 Hz, 3H), 1.31-1.40 (m, 2H), 1.61-1.69 (m, 2H), 2.49 (s, 3H), 2.76 (t, J=7.80 Hz, 2H), 3.42-3.45 (m, 1H), 5.38 (br s, 2H), 5.50 (br s, 1H), 6.77-6.93 (m, 2H), 7.10 (s, 1H), 7.25-7.31 (m, 2H), 7.50-7.66 (m, 4H), 8.02 (s, 1H).

FAB-MS: 533 (M+1).

What is claimed is:

1. A method of treating a condition in a mammal, the treatment of which is effected or facilitated by a decrease in endothelin mediated actions, comprising the administration, in an amount that is effective for antagonizing the effect of endothelin, of a compound of structural formula I, wherein:

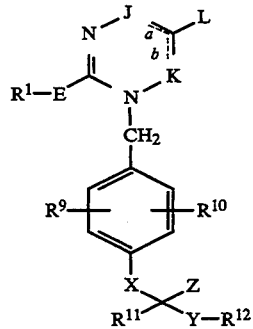

or a pharmaceutically acceptable salt thereof wherein:
R$^1$ is:
(a) (C$_1$-C$_6$)-alkyl, (C$_2$-C$_6$)-alkenyl or (C$_2$-C$_6$)-alkynyl each of which is unsubstituted or substituted with a substituent selected from the group consisting of:
  i) aryl as defined below,
  ii) (C$_3$-C$_7$)-cycloalkyl,
  iii) Cl, Br, I, F,
  iv) OH,
  v) NH$_2$,
  vi) NH(C$_1$-C$_4$)-alkyl,
  vii) N[(C$_1$-C$_4$)-alkyl]$_2$,
  viii) NHSO$_2$R$^2$,
  ix) CF$_3$,
  x) COOR$^2$, or
  xi) SO$_2$NHR$^{2a}$; and
(b) aryl, wherein aryl is defined as phenyl or naphthyl unsubstituted or substituted with 1 or 2 substituents selected from the group consisting of:
  i) Br, I, Cl, F, ii) $(C_1-C_4)$-alkyl,
iii) $(C_1-C_4)$-alkoxy,
iv) $NO_2$,
v) $CF_3$
vi) $SO_2NR^{2a}R^{2a}$,
vii) $(C_1-C_4)$-alkylthio,
viii) hydroxy,
ix) amino,
x) $(C_3-C_7)$-cycloalkyl,
xi) $(C_3-C_{10})$-alkenyl; and (c) heteroaryl, wherein heteroaryl is defined as an unsubstituted, monosubstituted or disubstituted heteroaromatic 5- or 6- membered cyclic moiety, which can contain one or two members selected from the group consisting of N, O, S and wherein the substituents are members selected from the group consisting of:
i) Cl, Br, I, or F,
ii) OH,
iii) SH,
iv) $NO_2$,
v) $(C_1-C_4)$-alkyl,
vi) $(C_2-C_4)$-alkenyl,
vii) $(C_2-C_4)$-alkynyl,
viii) $(C_1-C_4)$-alkoxy, or
ix) $CF_3$, or (d) $(C_1-C_4)$-perfluoroalkyl; and E is:
(a) a single bond,
(b) $-S(O)_n(CH_2)_s-$, or
(c) $-O-$; and n is: 0 to 2; and
s is: 0 to 5; and J is: (a) $-C(=M)-$, (b) J and L are connected together to form a 6-membered aromatic ring substituted with $R^{7a}$, $R^{7b}$, $R^{8a}$ and $R^{8b}$ or (c) J and L are connected together to form a 6-membered aromatic ring containing one nitrogen atom not at $J^1$, substituted with $R^{7a}$, $R^{7b}$, $R^{8a}$ and R8b; and K is: (a) $-C(=M)-$, (b) K and L are connected together to form a 6-membered aromatic ring substituted with $R^{7a}$, $R^{7b}$, $R^{8a}$ and $R^{8b}$, or (c) K and L are connected together to form a 6-membered aromatic ring containing one nitrogen atom, substituted on the carbon atoms with $R^{7a}$, $R^{7b}$ and R8b; and one of a or b is a double bond in Formula I provided that when J is $-C(=M)-$ then b is a double bond and when K is $-C(=M)-$ then a is a double bond;

L is the point of attachment of the 6-membered fused aromatic ring optionally containing one nitrogen atom; and M is: O, S or $NR^{15}$; and $R^2$ is:
(a) H, or
(b) $(C_1-C_6)$-alkyl; and $R^{2a}$ is:
(a) $R^2$,
(b) $CH_2$-aryl, or
(c) aryl; and $R^{7a}$ and $R^{7b}$ are independently:
(a) H,
(b) $(C_1-C_6)$-alkyl, $(C_2-C_6)$-alkenyl or $(C_2-C_6)$-alkynyl,
(c) Cl, Br, I, F,
(d) $CF_3$, or (e) when $R^{7a}$ and $R^{7b}$ are bonded to adjacent carbon atoms, they can be joined to form a phenyl ring;

$R^{8a}$ and $R^{8b}$ are independently:
(a) H,
(b) aryl-$(C_1-C_4)$-alkyl,
(c) heteroaryl-$(C_1-C_4)$-alkyl,
(d) $(C_1-C_6)$-alkyl, which is unsubstituted or substituted with a substituent selected from the group consisting of: $-CON(R^{2a})_2$, $-$heteroaryl, $-S(O)_n-R^{16}$, $-$tetrazol-5-yl, $-CONHSO_2R^{16}$, $-SO_2NH$-heteroaryl, $-SO_2NHCOR^{16}$, $-PO(OR^2)_2$, $-PO(OR^{2a})_2$, $-SO_2NH-CN$, $-NR^2COOR^{16}$, $-OH$, $-NH_2$, guanidino, $(C_1-C_4)$-alkoxy, $(C_1-C_4)$-alkylthio, $(C_1-C_4)$-alkylamino, $(C_1-C_4)$-dialkylamino, $-COOR^{2a}$, $-CONHR^{2a}$, $-O-COR^{2a}$, or aryl,
(e) $-CO$-aryl,
(f) $(C_3-C_7)$-cycloalkyl,
(g) Cl, Br, I, F,
(h) $-OH$,
(i) $-OR^{16}$,
(j) $-SH$,
(k) $-S(O)_n-(C_1-C_4)$-alkyl,
(l) $-COR^{2a}$,
(m) $-CO_2H$,
(n) $-CO_2-(C_1-C_4)$-alkyl,
(o) $-SO_3H$,
(p) $-NR^2R^{16}$,
(q) $-NR^2COR^{16}$,
(r) $-NR^2COOR^{16}$,
(s) $-SO_2NHR^{2a}$,
(t) $-SO_2NR^2R^{2a}$,
(u) $-NO_2$,
(v) $-NHSO_2CF_3$,
(w) $-CONR^{2a}R^{2a}$,
(x) $-(C_1-C_4)$-perfluoroalkyl,
(y) $-COOR^2$,
(z) $-SO_3H$,
(aa) $-N(R^2)SO_2R^{16}$,
(bb) $-NR^2CONR^4R^{16}$,
(cc) $-OC(=O)NR^{16}R^{2a}$,
(dd) $-$aryl,
(ee) $-NHSO_2CF_3$,
(ff) $-SO_2NH$-heteroaryl,
(gg) $-SO_2NHCOR^{16}$,
(hh) $-CONHSO_2R^{16}$,
(ii) $-PO(OR^2)_2$,
(jj) $-$tetrazol-5-yl,
(kk) $-CONH$(tetrazol-5-yl),
(ll) $-SO_2NHCN$, or
(mm) $-$heteroaryl; and $R^9$ and $R^{10}$ are independently:
(a) H,
(b) $(C_1-C_6)$-alkyl, unsubstituted or substituted with $(C_3-C_7)$-cycloalkyl,
(c) $(C_2-C_6)$-alkenyl,
(d) $(C_2-C_6)$-alkynyl,
(e) Cl, Br, F, I,
(f) $(C_1-C_6)$-alkoxy,
(g) when $R^9$ and $R^{10}$ are on adjacent carbons, they can be joined to form a phenyl ring,
(h) perfluoro-$(C_1-C_6)$-alkyl,
(i) $(C_3-C_7)$-cycloalkyl, unsubstituted or substituted with $(C_1-C_6)$-alkyl,
(j) aryl,
(k) $(C_1-C_6)$-alkyl-$S(O)_n-(CH_2)_n-$,
(l) hydroxy-$(C_1-C_6)$-alkyl, (m) —$CF_3$,
(n) —$CO_2R^{2a}$,
(o) —OH,
(p) —$NR^2R^{16}$,
(q) —[($C_1$-$C_6$)-alkyl]$NR^2R^{16}$,
(r) —$NO_2$,
(s) —$(CH_2)_n$—$SO_2$—$N(R^2)_2$,
(t) —$NR^2CO$—($C_1$-$C_4$)-alkyl, or
(u) —$CON(R^2)_2$;

X is:
(a) —O—,
(b) —$S(O)_n$—,
(c) —$NR^{13}$—,
(d) —$CH_2O$—,
(e) —$CH_2S(O)_n$,
(f) —$CH_2NR^{13}$—,
(g) —$OCH_2$—,
(h) —$NR^{13}CH_2$—,
(i) —$S(O)_nCH_2$—,
(j) single bond, or Y is:
(a) single bond,
(b) —O—,
(c) —$S(O)_n$—, or
(d) —$NR^{13}$—; and except that X and Y are not defined in such a way that the carbon atom to which Z is attached also simultaneously is bonded to two heteroatoms (O, N, S, SO, $SO_2$);

$R^{11}$ and $R^{12}$ are independently:
(a) H,
(b) ($C_1$-$C_6$)-alkyl, unsubstituted or substituted with a substituent selected from the group consisting of:
  (i) aryl,
  (ii) ($C_3$-$C_7$)-cycloalkyl,
  (iii) $NR^2R^{21}$,
  (iv) morpholin-4-yl,
  (v) OH,
  (vi) $CO_2R^{2a}$, or
  (vii) $CON(R^2)_2$,
(c) aryl or aryl-($C_1$-$C_2$)-alkyl, unsubstituted or substituted with 1 to 3 substituents selected from the group consisting of:
  (i) Cl, Br, I, F,
  (ii) ($C_1$-$C_6$)-alkyl,
  (iii) [($C_1$-$C_5$)-alkenyl]$CH_2$—,
  (iv) [($C_1$-$C_5$)-alkynyl]$CH_2$—,
  (v) ($C_1$-$C_6$)-alkyl—$S(O)_n$—$(CH_2)_n$—,
  (vi) —$CF_3$,
  (vii) —$CO_2R^{2a}$,
  (viii) —OH,
  (ix) —$NR^2R^{16}$,
  (x) —$NO_2$,
  (xi) —$NR^2COR^2$,
  (xii) —$CON(R^2)_2$,
  (xiii) —G—[($C_1$-$C_6$)-alkyl]-$R^{18}$,
  (xiv) —$N[CH_2CH_2]_2Q$, or
  (xv) —$P(O)[O-(C_1-C_4)-alkyl]_2$, and can additionally be substituted with 1 or 2 substituents selected from the group consisting of: Br, Cl or F,
(d) ($C_3$-$C_7$)-cycloalkyl, or
(e) when Y is single bond, $R^{11}$ and $R^{12}$ can be joined to form a ring of 5 to 7 carbon atoms, the ring can be benzo-fused and one carbon of which can be replaced with a heteroatom selected from the group consisting of: O, $S(O)_n$ and $NR^{17}$; and G is: a single bond, O, $S(O)_n$ or $NR^{18}$; and
Q is: O, $S(O)_n$ or $NR^{17}$; and
$R^{13}$ is:
(a) H,
(b) ($C_1$-$C_6$)-alkyl,
(c) aryl,
(d) aryl-($C_1$-$C_6$)-alkyl-(C=O)—,
(e) ($C_1$-$C_6$)-alkyl-(C=O)—,
(f) [($C_2$-$C_5$)-alkenyl]$CH_2$—,
(g) [($C_2$-$C_5$)-alkynyl]$CH_2$—, or
(h) aryl-$CH_2$—; and Z is:
(a) —$CO_2H$,
(b) —$CO_2R^{19}$,
(c) —tetrazol-5-yl,
(d) —CONH(tetrazol-5-yl)
(e) —$CONHSO_2$-aryl, wherein aryl is phenyl or naphthyl, which is unsubstituted or substituted as defined in $R^1$(b),
(f) —$CONHSO_2$—($C_1$-$C_8$)-alkyl, wherein the alkyl group is unsubstituted or substituted with a substituent selected from the group consisting of: —OH, —SH, —O($C_1$-$C_4$)-alkyl, —S—($C_1$-$C_4$)-alkyl, —$CF_3$, Cl, Br, F, I, —$NO_2$, —$CO_2H$, —$CO_2$—($C_1$-$C_4$)-alkyl, —$NH_2$, —NH[($C_1$-$C_4$)-alkyl], —N[($C_1$-$C_4$)-alkyl]$_2$; and
(g) —$CONHSO_2$—($C_1$-$C_4$)-perfluoroalkyl,
(h) —$CONHSO_2$-heteroaryl, wherein heteroaryl is unsubstituted or substituted as defined in $R^1$(c),
(i) —$CONHSO_2NR^{2a}R^{2a}$; and
(j) —$SO_2NHCO$-aryl, wherein aryl is phenyl or naphthyl, which is unsubstituted or substituted as defined in $R^1$(b);
(k) —$SO_2NHCO$-($C_1$-$C_8$)-alkyl, wherein the alkyl group is unsubstituted or substituted with a substituent selected from the group consisting of: —OH, —SH, —O($C_1$-$C_4$)-alkyl, —S—($C_1$-$C_4$)-alkyl, —$CF_3$, Cl, Br, F, I, —$NO_2$, —$CO_2H$, —$CO_2$—($C_1$-$C_4$)-alkyl, —$NH_2$, —NH[($C_1$-$C_4$)-alkyl], —N[($C_1$-$C_4$)-alkyl]$_2$; and
(l) —$SO_2NHCO$-($C_1$-$C_4$)-perfluoroalkyl,
(m) —$SO_2NHCO$-heteroaryl, wherein heteroaryl is unsubstituted or substituted as defined in $R^1$(c),
(n) —$SO_2NHCONR^{2a}R^{2a}$;
(o) —$PO(OH)_2$,
(p) —$PO(OR^2)_2$, or
(q) —$PO(OH)(OR^2)$; and $R^{14}$ is:
(a) H,
(b) ($C_1$-$C_8$)-alkyl,
(c) ($C_1$-$C_8$)-perfluoroalkyl,
(d) ($C_3$-$C_6$)-cycloalkyl,
(e) phenyl, or
(f) benzyl; and $R^{15}$ is:
(a) H,
(b) aryl, which is unsubstituted or substituted with 1 or 2 substituents selected from the group consisting of: Cl, Br, I, F, —O—($C_1$-$C_4$)-alkyl, ($C_1$-$C_4$)-alkyl, —$NO_2$, —$CF_3$, —$SO_2NR^2R^{2a}$, —S—($C_1$-$C_4$)-alkyl, —OH, —$NH_2$, ($C_3$-$C_7$)-cycloalkyl, ($C_3$-$C_{10}$)-alkenyl;
(c) ($C_1$-$C_6$)-alkyl, ($C_2$-$C_6$)-alkenyl or ($C_2$-$C_6$)-alkynyl each of which is unsubstituted or substituted with one or more substituents selected from the group consisting of: aryl, ($C_3$-$C_7$)-cycloalkyl, Cl, Br, I, F, —OH, —$NH_2$, —NH[($C_1$-$C_4$)alkyl], —N[($C_1$-$C_4$)-alkyl]$_2$, —NH—SO$_2$R$^{2a}$,
—COOR$^{2a}$, —SO$_2$NHR$^{2a}$; or (d) an unsubstituted, monosubstituted or disubstituted aromatic 5 or 6 membered ring which can contain one or two heteroatoms selected from the group consisting of N, O, S, and wherein the substituents are members selected from the group consisting of —OH, —SH, ($C_1$-$C_4$)-alkyl, ($C_1$-$C_4$)-alkyloxy, —CF$_3$, Cl, Br, I, F, or NO$_2$; and R$^{16}$ is:
(a) aryl, or
(b) ($C_1$-$C_4$)-alkyl, is unsubstituted or substituted with:
  i) NH$_2$,
  ii) NH[($C_1$-$C_4$)-alkyl],
  iii) N[($C_1$-$C_4$)-alkyl]$_2$,
  iv) CO$_2$H,
  v) CO$_2$($C_1$-$C_4$)-alkyl,
  vi) OH,
  vii) SO$_3$H, or
  viii) SO$_2$NH$_2$; and R$^{17}$ is:
(a) H,
(b) ($C_1$-$C_4$)-alkyl,
(c) ($C_1$-$C_4$)-alkoxyl,
(d) aryl,
(e) aryl-($C_1$-$C_4$)-alkyl,
(f) CO$_2$R$^{2a}$,
(g) CON(R$^2$)$_2$,
(h) SO$_2$R$^{2a}$,
(i) SO$_2$N(R$^2$)$_2$,
(j) P(O)[($C_1$-$C_4$)-alkoxyl]$_2$, or
(k) imidazol-2-yl or imidazol-4-yl, in which the imidazolyl can be substituted with ($C_1$-$C_4$)-alkyl; and R$^{18}$ is:
(a) OH,
(b) NR$^2$R$^{16}$,
(c) CO$_2$R$^{2a}$,
(d) CON(R$^2$)$_2$,
(e) S(O)$_n$—($C_1$-$C_4$)-alkyl, or
(f) N(CH$_2$CH$_2$)$_2$Q, R$^{19}$ is:
(a) ($C_1$-$C_4$)-alkyl,
(b) CHR$^{20}$—O—COR$^{21}$,
(c) CH$_2$CH$_2$—N[($C_1$-$C_2$)-alkyl]$_2$,
(d) CH$_2$CH$_2$—N[CH$_2$CH$_2$]$_2$O,
(e) (CH$_2$CH$_2$O)$_y$—O—[($C_1$-$C_4$)-alkyl], wherein y is 1 or 2,
(f) aryl or CH$_2$-aryl, where aryl is as defined above or optionally substituted with CO$_2$($C_1$-$C_4$)-alkyl,

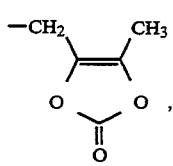 (g)

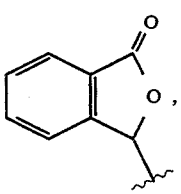 (h)

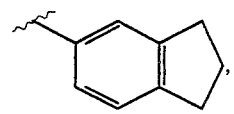 (i)

or

—CH$_2$ 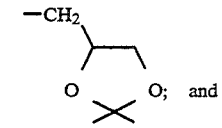 (j)

R$^{20}$ and R$^{21}$ independently are: ($C_1$-$C_6$)-alkyl or phenyl.

2. The method as recited in claim 1, wherein:
R$^1$ is:
(a) ($C_1$-$C_6$)-alkyl or ($C_2$-$C_6$)-alkenyl or ($C_2$-$C_6$)-alkynyl each of which is unsubstituted or substituted with a substituent selected from the group consisting of:
  i) ($C_1$-$C_4$)-alkylthio,
  ii) ($C_1$-$C_4$)-alkoxy,
  iii) CF$_3$,
  iv) CF$_2$CF$_3$, or
  v) ($C_3$-$C_5$)-cycloalkyl,
(b) ($C_1$-$C_4$)-perfluoroalkyl, or
(c) ($C_3$-$C_5$)-cycloalkyl; and E is:
(a) single bond,
(b) —S—, or
(c) —O—; and n is: 0, 1, or 2; and J is: (a) —C(=M)-,
(b) J and L are connected together to form a 6-membered aromatic ring substituted with R$^{7a}$, R$^{7b}$, R$^{8a}$ and R$^{8b}$ or (c) J and L are connected together to form a 6-membered aromatic ring containing one nitrogen atom not at J, substituted with R$^{7a}$, R$^{7b}$, R$^{8a}$ and R8b; and K is: (a) —C(=M)—, or (b) K and L are connected together to form a 6-membered aromatic ring substituted with R$^{7a}$, R$^{7b}$, R$^{8a}$ and R$^{8b}$, or (c) K and L are connected together to form a six-membered aromatic ring containing one nitrogen atom substituted with R$^{7a}$, R$^{7b}$ and R$^{8a}$ provided that one and only one of J and K is —C(=M)—; and one of a or b is a double bond in Formula I provided that when J is —C(=M)— then b is a double bond and when K is —C(=M)— then a is a double bond;

L is: the point of attachment of the 6-membered fused aromatic ring optionally containing one nitrogen atom; and M is: O, S or NR$^{15}$; and R$^2$ is:
(a) H,
(b) ($C_1$-$C_6$)-alkyl; and R$^{2a}$ is:
(a) R$^2$,
(b) CH$_2$aryl, or
(c) aryl; and R$^{7a}$ and R$^{7b}$ are independently:
(a) H,
(b) ($C_1$-$C_6$)-alkyl, ($C_2$-$C_6$)-alkenyl or ($C_2$C$_6$)-alkynyl,
(c) Cl, Br, I, F, (d) CF$_3$, or
(e) when R$^{7a}$ and R$^{7b}$ are bonded to adjacent carbon atoms, they can be joined to form a phenyl ring;

R$^{8a}$ and R$^{8b}$ are independently:
(a) H,
(b) aryl-(C$_1$-C$_4$)-alkyl,
(c) heteroaryl-(C$_1$-C$_4$)-alkyl,
(d) (C$_1$-C$_6$)-alkyl, is unsubstituted or substituted with a substituent selected from the group consisting of: —CON(R$^{2a}$)$_2$, —heteroaryl, —S(O)$_n$—R$^{16}$, —tetrazol-5-yl, —CONHSO$_2$R$^{16}$, —SO$_2$NH-heteroaryl, —SO$_2$NHCOR$^{16}$, —PO(OR$^2$)$_2$, —PO(OR$^{2a}$)$_2$, —SO$_2$NH—CN, —NR$^2$COOR$^{16}$, —OH, —NH$_2$, guanidino, (C$_1$-C$_4$)-alkoxy, (C$_1$-C$_4$)-alkylthio, (C$_1$-C$_4$)-alkylamino, (C$_1$-C$_4$)-dialkylamino, —COOR$^{2a}$, —CONHR$^{2a}$, —O—COR$^{2a}$, or aryl,
(e) —CO-aryl,
(f) (C$_3$-C$_7$)-cycloalkyl,
(g) Cl, Br, I, F,
(h) —OH,
(i) —OR$^{16}$,
(j) —SH,
(k) —S(O)$_n$—(C$_1$-C$_4$)-alkyl,
(l) —COR$^{2a}$,
(m) —CO$_2$H,
(n) —CO$_2$—(C$_1$-C$_4$)-alkyl,
(o) —SO$_3$H,
(p) —NR$^2$R$^{16}$,
(q) —NR$^2$COR$^{16}$,
(r) —NR$^2$COOR$^{16}$,
(s) —SO$_2$NR$^{2a}$,
(t) —SO$_2$NR$^2$R$^{2a}$,
(u) —NO$_2$,
(v) —NHSO$_2$CF$_3$,
(w) —CONR$^{2a}$R$^{2a}$,
(x) —(C$_1$-C$_4$)-perfluoroalkyl,
(y) —COOR$^2$,
(z) —SO$_3$H,
(aa) —N(R$^2$)SO$_2$R$^{16}$,
(bb) —NR$^2$CONR$^{2a}$R$^{16}$,
(cc) —OC(=O)NR$^{16}$R$^{2a}$,
(dd) —aryl,
(ee) —NHSO$_2$CF$_3$,
(ff) —SO$_2$NH-heteroaryl,
(gg) —SO$_2$NHCOR$^{16}$,
(hh) —CONHSO$_2$R$^{16}$,
(ii) —PO(OR$^2$)$_2$,
(jj) —tetrazol-5-yl,
(kk) —CONH(tetrazol-5-yl),
(ll) —SO$_2$NHCN, or
(mm) —heteroaryl; and R$^9$ and R$^{10}$ are independently:
(a) H,
(b) (C$_1$-C$_6$)-alkyl, unsubstituted or substituted with (C$_3$-C$_7$)cycloalkyl,
(c) (C$_2$-C$_6$)-alkenyl,
(d) (C$_2$-C$_6$)-alkynyl,
(e) Cl, Br, F, I,
(f) (C$_1$-C$_6$)-alkoxy,
(g) when R$^9$ and R$^{10}$ are on adjacent carbons, they can be joined to form a phenyl ring,
(h) (C$_1$-C$_6$)-perfluoroalkyl,
(i) (C$_3$-C$_7$)-cycloalkyl, unsubstituted or substituted with (C$_1$-C$_6$)-alkyl,
(j) aryl,
(k) (C$_1$-C$_6$)-alkyl—S(O)$_n$—(CH$_2$)$_n$—,
(l) hydroxy-(C$_1$-C$_6$)-alkyl,
(m) —CF$_3$,
(n) —CO$_2$R$^{2a}$,
(o) —OH,
(p) —NR$^2$R$^{21}$,
(q) —[(C$_1$-C$_6$)-alkyl]NR$^2$R$^{16}$,
(r) —NO$_2$,
(s) —(CH$_2$)$_n$—SO$_2$—N(R$^2$)$_2$,
(t) —NR$^2$CO—(C$_1$-C$_4$)-alkyl, or
(u) —CON(R$^2$)$_2$; and X is:
(a) —O—,
(b) —S(O)$_n$—,
(c) —NR$^{13}$—,
(d) —CH$_2$O—,
(e) —CH$_2$S(O)$_n$,
(f) —CH$_2$NR$^{13}$—,
(g) —OCH$_2$—,
(h) —NR$^{13}$CH$_2$—,
(i) —S(O)$_n$CH$_2$—, or
(j) single bond; and Y is:
(a) single bond,
(b) —O—,
(c) —S(O)n—, or
(d) —NR$^{13}$—; and
except that X and Y are not defined in such a way that the carbon atom to which Z is attached also simultaneously is bonded to two heteroatoms (O, N, S, SO, SO$_2$);

R$^{11}$ and R$^{12}$ are independently:
(a) H,
(b) (C$_1$-C$_6$)-alkyl, unsubstituted or substituted with a substituent selected from the group consisting of:
 (i) aryl,
 (ii) (C$_3$-C$_7$)-cycloalkyl,
 (iii) NR$^2$R$^{16}$,
 (iv) morpholin-4-yl,
 (v) OH,
 (vi) CO$_2$R$^{2a}$, or
 (vii) CON(R$^2$)$_2$,
(c) aryl or aryl-(C$_1$-C$_2$)-alkyl, unsubstituted or substituted with 1 to 3 substitutents selected from the group consisting of:
 (i) Cl, Br, I, F,
 (ii) (C$_1$-C$_6$)-alkyl,
 (iii) [(C$_1$-C$_5$)-alkenyl]CH$_2$—,
 (iv) [(C$_1$-C$_5$)-alkynyl]CH$_2$—,
 (v) (C$_1$-C$_6$)-alkyl—S(O)$_n$—(CH$_2$)$_n$—,
 (vi) —CF$_3$,
 (vii) —CO$_2$R$^{2a}$,
 (viii) —OH,
 (ix) —NR$^2$R$^{16}$,
 (x) —NO$_2$,
 (xi) —NR$^2$COR$^2$,
 (xii) —CON(R$^2$)$_2$,
 (xiii) —G—[(C$_1$-C$_6$)-alkyl]-R$^{18}$,
 (xiv) —N[CH$_2$CH$_2$]$_2$Q, or
 (xv) —P(O)[O—(C$_1$-C$_4$)-alkyl]$_2$,
 and can additionally be substituted with 1 or 2 substituents selected from the group consisting of: Br, Cl or F,
(d) (C$_3$-C$_7$)-cycloalkyl, or
(e) when Y is single bond, R$^{11}$ and R$^{12}$ can be joined to form a ring of 5 to 7 carbon atoms, the ring can be benzo-fused and one carbon of which can be replaced with a heteroatom selected from the group consisting of: O, $S(O)_n$ and $NR^{17}$; and G is: a single bond, O, $S(O)_n$ or $NR^{18}$; and Q is: O, $S(O)_n$ or $NR^{17}$; and $R^{13}$ is:
- (a) H,
- (b) $(C_1-C_6)$-alkyl,
- (c) aryl,
- (d) aryl-$(C_1-C_6)$-alkyl-(C=O)—,
- (e) $(C_1-C_6)$-alkyl-(C=O)—,
- (f) [$(C_2-C_5)$-alkenyl]$CH_2$—, or
- (g) [$(C_2-C_5)$-alkynyl]$CH_2$—, or
- (h) aryl-$CH_2$—; and Z is:
- (a) —$CO_2H$,
- (b) —$CO_2R^{19}$,
- (c) —tetrazol-5-yl,
- (d) —CONH(tetrazol-5-yl),
- (e) —$CONHSO_2$-aryl, wherein aryl is phenyl or naphthyl, which is unsubstituted or substituted as defined in $R^1(b)$,
- (f) —$CONHSO_2$-$(C_1-C_8)$-alkyl, wherein the alkyl group is unsubstituted or substituted with a substituent selected from the group consisting of: —OH, —SH, —O$(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —NH[$(C_1-C_4)$-alkyl], —N[$(C_1-C_4)$-alkyl]$_2$; and
- (g) —$CONHSO_2$-$(C_1-C_4)$-perfluoroalkyl,
- (h) —$CONHSO_2$-heteroaryl, wherein heteroaryl is unsubstituted or substituted as defined in $R^1(c)$,
- (i) —$CONHSO_2NR^{2a}R^{2a}$,
- (j) —$SO_2NHCO$-aryl, wherein aryl is phenyl or naphthyl, which is unsubstituted or substituted as defined in $R^1(b)$,
- (k) —$SO_2NHCO$-$(C_1-C_8)$-alkyl, wherein the alkyl group is unsubstituted or substituted with a substituent selected from the group consisting of: —OH, —SH, —O$(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —NH[$(C_1-C_4)$-alkyl], —N[$(C_1-C_4)$-alkyl]$_2$; and
- (l) —$SO_2NHCO$-$(C_1-C_4)$-perfluoroalkyl,
- (m) —$SO_2NHCO$-heteroaryl, wherein heteroaryl is unsubstituted or substituted as defined in $R^1(c)$, or
- (n) —$SO_2NHCONR^{2a}R^{2a}$; and $R^{15}$ is:
- (a) H,
- (b) aryl, is unsubstituted or substituted with 1 or 2 substituents selected from the group consisting of Cl, Br, I, F, —O—$(C_1-C_4)$-alkyl, $(C_1-C_4)$-alkyl, —$NO_2$, —$CF_3$, —$SO_2NR^2R^{2a}$, —S—$(C_1-C_4)$-alkyl, —OH, —$NH_2$, $(C_3-C_7)$-cycloalkyl, $(C_3-C_{10})$-alkenyl;
- (c) $(C_1-C_6)$-alkyl, $(C_2-C_6)$-alkenyl or $(C_2-C_6)$-alkynyl each of which is unsubstituted or substituted with one or more substituents selected from the group consisting of: aryl, $(C_3-C_7)$-cycloalkyl, Cl, Br, I, F, —OH, —$NH_2$, —NH[$(C_1-C_4)$-alkyl], —N[$(C_1-C_4)$-alkyl]$_2$, —NH—$SO_2R^{2a}$, —$COOR^{2a}$, —$SO_2NHR^{2a}$; or
- (d) an unsubstituted, monosubstituted or disubstituted aromatic 5 or 6 membered ring which contains one or two heteroatoms selected from the group consisting of N, O, S, and wherein the substituents are members selected from the group consisting of —OH, —SH, $(C_1-C_4)$-alkyl, $(C_1-C_4)$-alkyloxy —$CF_3$, Cl, Br, I, F, or $NO_2$; and $R^{16}$ is:
- (a) aryl, or
- (b) $(C_1-C_4)$-alkyl which is unsubstituted or substituted with:
  - i) $NH_2$,
  - ii) NH[$(C_1-C_4)$-alkyl],
  - iii) N[$(C_1-C_4)$-alkyl]$_2$,
  - iv) $CO_2H$,
  - v) $CO_2(C_1-C_4)$-alkyl,
  - vi) OH,
  - vii) $SO_3H$, or
  - viii) $SO_2NH_2$; and $R^{17}$ is:
- (a) H,
- (b) $(C_1-C_4)$-alkyl,
- (c) $(C_1-C_4)$-alkoxyl,
- (d) aryl,
- (e) aryl-$(C_1-C_4)$-alkyl,
- (f) $CO_2R^{2a}$,
- (g) $CON(R^2)_2$,
- (h) $SO_2R^{2a}$,
- (i) $SO_2N(R^2)_2$,
- (j) P(O)[$(C_1-C_4)$-alkoxyl]$_2$, or
- (k) imidazol-2-yl or imidazol-4-yl, in which the imidazolyl can be substituted with $(C_1-C_4)$-alkyl; and $R^{18}$ is:
- (a) OH,
- (b) $NR^2R^{16}$,
- (c) $CO_2R^{2a}$,
- (d) $CON(R^2)_2$,
- (e) $S(O)n$-$(C_1-C_4)$-alkyl, or
- (f) N[$CH_2CH_2$]$_2$Q; and $R^{19}$ is:
- (a) $(C_1-C_4)$-alkyl,
- (b) $CHR^{20}$—O—$COR^{21}$,
- (c) $CH_2CH_2$—N[$(C_1-C_2)$-alkyl]$_2$,
- (d) $CH_2CH_2$—N[$CH_2CH_2$]$_2$O,
- (e) $(CH_2CH_2O)_y$—O—[$(C_1-C_4)$-alkyl], wherein y is 1 or 2,
- (f) aryl or $CH_2$-aryl, where aryl is as defined above or optionally substituted with $CO_2(C_1-C_4)$-alkyl,

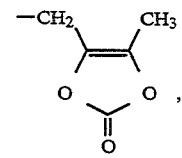 (g)

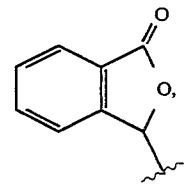 (h)

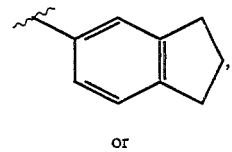 (i)

or

-continued

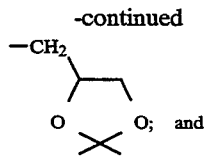

$R^{20}$ and $R^{21}$ independently are: $(C_1-C_6)$-alkyl or phenyl.

3. The method as recited in claim 2, wherein:

$R^1$ is:
- (a) $(C_1-C_6)$-alkyl or $(C_2-C_6)$-alkenyl or $(C_2-C_6)$-alkynyl each of which is unsubstituted or substituted with a substituent selected from the group consisting of:
  - i) $(C_1-C_4)$-alkylthio,
  - ii) $(C_1-C_4)$-alkoxy,
  - iii) $CF_3$,
  - iv) $CF_2CF_3$, or
  - v) $(C_3-C_5)$-cycloalkyl,
- (b) $(C_1-C_4)$-perfluoroalkyl, or
- (c) $(C_3-C_5)$-cycloalkyl; and E is:
- (a) single bond,
- (b) —S—, or
- (c) —O—; and n is 0, 1, or 2; and J is: (a) —C(=M)—, (b) J and L are connected together to form a 6-membered aromatic ring substituted with $R^{7a}$, $R^{7b}$, $R^{8a}$ and $R^{8b}$ or (c) J and L are connected together to form a 6-membered aromatic ring containing one nitrogen atom not at J, substituted with $R^{7a}$, $R^{7b}$, $R^{8a}$ and $R^{8b}$; and K is: (a) —C(=M)—, or (b) K and L are connected together to form a 6-membered aromatic ring substituted with $R^{7a}$, $R^{7b}$, $R^{8a}$ and $R^{8b}$, or (c) K and L are connected together to form a six-membered aromatic ring containing one nitrogen atom substituted with $R^{7a}$, $R^{7b}$ and $R^{8a}$ provided that one and only one of J and K is —C(=M)—; and one of a or b is a double bond in Formula I provided that when J is —C(=M)— then b is a double bond and when K is —C(=M)— then a is a double bond;

L is the point of attachment of the 6-membered fused aromatic ring optionally containing one nitrogen atom; and M is: O, S or $NR^{15}$; and $R^2$ is:
- (a) H,
- (b) $(C_1-C_6)$-alkyl; and $R^{2a}$ is:
- (a) $R^2$,
- (b) $CH_2$aryl, or
- (c) aryl; and $R^{7a}$ and $R^{7b}$ are independently:
- (a) H,
- (b) $(C_1-C_6)$-alkyl, $(C_2-C_6)$-alkenyl or $(C_2-C_6)$-alkynyl,
- (c) Cl, Br, I, F,
- (d) $CF_3$, or
- (e) when $R^{7a}$ and $R^{7b}$ are bonded to adjacent carbon atoms, they can be joined to form a phenyl ring;

$R^{8a}$ and $R^{8b}$ are independently:
- (a) H,
- (b) aryl-$(C_1-C_4)$-alkyl,
- (c) heteroaryl-$(C_1-C_4)$-alkyl,
- (d) $(C_1-C_6)$-alkyl, is unsubstituted or substituted with a substituent selected from the group consisting of: —CON$(R^{2a})_2$, —heteroaryl, —S(O)$_n$—$R^{16}$, —tetrazol-5-yl, —CONHSO$_2R^{16}$, —SO$_2$NH-heteroaryl, —SO$_2$NHCOR$^{16}$, —PO(OR$^2)_2$, —PO(OR$^{2a})_2$, —SO$_2$NH—CN, —NR$^2$COOR$^{16}$, —OH, —NH$_2$, guanidino, $(C_1-C_4)$-alkoxy, $(C_1-C_4)$-alkylthio, $(C_1-C_4)$-alkylamino, $(C_1-C_4)$-dialkylamino, —COOR$^{2a}$, —CONHR$^{2a}$, —O—COR$^{2a}$, or aryl,
- (e) —CO-aryl,
- (f) $(C_3-C_7)$-cycloalkyl,
- (g) Cl, Br, I, F,
- (h) —OH,
- (i) —OR$^{16}$,
- (j) —SH,
- (k) —S(O)$_n$—$(C_1-C_4)$-alkyl,
- (l) —COR$^{2a}$,
- (m) —CO$_2$H,
- (n) —CO$_2$—$(C_1-C_4)$-alkyl,
- (o) —SO$_3$H,
- (p) —NR$^2R^{16}$,
- (q) —NR$^2$COR$^{16}$,
- (r) —NR$^2$COOR$^{16}$,
- (s) —SO$_2$NR$^{2a}$,
- (t) —SO$_2$NR$^2R^{2a}$,
- (u) —NO$_2$,
- (v) —NHSO$_2$CF$_3$,
- (w) —CONR$^{2a}R^{2a}$,
- (x) —$(C_1-C_4)$-perfluoroalkyl,
- (y) —COOR$^2$,
- (z) —SO$_3$H,
- (aa) —N(R$^2$)SO$_2R^{16}$,
- (bb) —NR$^2$CONR$^{2a}R^{16}$,
- (cc) —OC(=O)NR$^{16}R^{2a}$,
- (dd) —aryl,
- (ee) —NHSO$_2$CF$_3$,
- (ff) —SO$_2$NH-heteroaryl,
- (gg) —SO$_2$NHCOR$^{16}$,
- (hh) —CONHSO$_2R^{16}$,
- (ii) —PO(OR$^2)_2$,
- (jj) —tetrazol-5-yl,
- (kk) —CONH(tetrazol-5-yl),
- (ll) —SO$_2$NHCN, or
- (mm) —heteroaryl; and $R^9$ and $R^{10}$ are independently:
- (a) H,
- (b) $(C_1-C_6)$-alkyl, unsubstituted or substituted with $(C_3-C_7)$-cycloalkyl,
- (c) $(C_2-C_6)$-alkenyl,
- (d) $(C_2-C_6)$-alkynyl,
- (e) Cl, Br, F, I,
- (f) $(C_1-C_6)$-alkoxy,
- (g) when $R^9$ and $R^{10}$ are on adjacent carbons, they can be joined to form a phenyl ring,
- (h) $(C_1-C_6)$-perfluoroalkyl,
- (i) $(C_3-C_7)$-cycloalkyl, unsubstituted or substituted with $(C_1-C_6)$-alkyl,
- (j) aryl,
- (k) $(C_1-C_6)$-alkyl—S(O)$_n$—(CH$_2$)$_n$—,
- (l) hydroxy-$(C_1-C_6)$-alkyl,
- (m) —CF$_3$,
- (n) —CO$_2R^{2a}$,
- (o) —OH,
- (p) —NR$^2R^{16}$,
- (q) —[$(C_1-C_6)$-alkyl]NR$^2R^{16}$,
- (r) —NO$_2$,
- (s) —(CH$_2$)$_n$—SO$_2$—N(R$^2)_2$, (t) —NR²CO—(C₁-C₄)-alkyl, or
(u) —CON(R²)₂; and X is:
(a) —O—,
(b) —S(O)$_n$—,
(c) —NR¹³—,
(d) —CH₂O—,
(e) —CH₂S(O)$_n$,
(f) —CH₂NR¹³—,
(g) —OCH₂—,
(h) —NR¹³CH₂—,
(i) —S(O)$_n$CH₂—, or
(j) single bond; and Y is:
(a) single bond,
(b) —O—,
(c) —S(O)$_n$—, or
(d) —NR¹³—; and except that X and Y are not defined in such a way that the carbon atom to which Z is attached also simultaneously is bonded to two heteroatoms (O, N, S, SO, SO₂);

R¹¹ and R¹² are independently:
(a) H,
(b) (C₁-C₆)-alkyl, unsubstituted or substituted with a substituent selected from the group consisting of:
  (i) aryl,
  (ii) (C₃-C₇)-cycloalkyl,
  (iii) NR²R¹⁶,
  (iv) morpholin-4-yl,
  (v) OH,
  (vi) CO₂R²$^a$, or
  (vii) CON(R²)₂,
(c) aryl or aryl-(C₁-C₂)-alkyl, unsubstituted or substituted with 1 to 3 substituents selected from the group consisting of:
  (i) Cl, Br, I, F,
  (ii) (C₁-C₆)-alkyl,
  (iii) [(C₁-C₅)-alkenyl]CH₂—,
  (iv) [(C₁-C₅)-alkynyl]CH₂—,
  (v) (C₁-C₆)-alkyl—S(O)$_n$—(CH₂)$_n$—,
  (vi) —CF₃,
  (vii) —CO₂R²$^a$,
  (viii) —OH,
  (ix) —NR²R¹⁶,
  (x) —NO₂,
  (xi) —NR²COR²,
  (xii) —CON(R²)2,
  (xiii) —G—[(C₁-C₆)-alkyl]-R¹⁸,
  (xiv) —N[CH₂CH₂]₂Q, or
  (xv) —P(O)[O—(C₁-C₄)-alkyl]₂, and can additionally be substituted with 1 or 2 substituents selected from the group consisting of: Br, Cl or F,
(d) (C₃-C₇)-cycloalkyl, or
(e) when Y is single bond, R¹¹ and R¹² can be joined to form a ring of 5 to 7 carbon atoms, the ring can be benzo-fused and one carbon of which can be replaced with a heteroatom selected from the group consisting of: O, S(O)$_n$ and NR¹⁷; and G is: a single bond, O, S(O)$_n$ or NR¹⁸; and
Q is: O, S(O)$_n$ or NR¹⁷; and R¹³ is:
(a) H,
(b) (C₁-C₆)-alkyl,
(c) aryl,
(d) aryl-(C₁-C₆)-alkyl-(C═O)—,
(e) (C₁-C₆)-alkyl-(C═O)—,
(f) [(C₂-C₅)-alkenyl]CH₂—,
(g) [(C₂-C₅)-alkynyl]CH₂—, or
(h) aryl-CH₂—; and Z is:
(a) —CO₂H,
(b) —CO₂R¹⁹,
(c) —tetrazol-5-yl,
(d) —CONH(tetrazol-5-yl),
(e) —CONHSO₂-aryl, wherein aryl is phenyl or naphthyl, which is unsubstituted or substituted as defined in R¹(b),
(f) —CONHSO₂-(C₁-C₈)-alkyl, wherein the alkyl group is unsubstituted or substituted with a substituent selected from the group consisting of: —OH, —SH, —O(C₁-C₄)-alkyl, —S—(C₁-C₄)-alkyl, —CF₃, Cl, Br, F, I, —NO₂, —CO₂H, —CO₂-(C₁-C₄)-alkyl, —NH₂, —NH[(C₁-C₄)-alkyl], —N[(C₁-C₄)-alkyl]₂; and
(g) —CONHSO₂-(C₁-C₄)-perfluoroalkyl,
(h) —CONHSO₂-heteroaryl, wherein heteroaryl is unsubstituted or substituted as defined in R¹(c),
(i) —CONHSO₂NR²$^a$R²$^a$,
(j) —SO₂NHCO-aryl, wherein aryl is phenyl or naphthyl, which is unsubstituted or substituted as defined in R¹(b),
(k) —SO₂NHCO-(C₁-C₈)-alkyl, wherein the alkyl group is unsubstituted or substituted with a substituent selected from the group consisting of: —OH, —SH, —O(C₁-C₄)-alkyl, —S—(C₁-C₄)-alkyl, —CF₃, Cl, Br, F, I, —NO₂, —CO₂H, —CO₂-(C₁-C₄)-alkyl, —NH₂, —NH[(C₁-C₄)-alkyl], —N[(C₁-C₄)-alkyl]₂; and
(l) —SO₂NHCO-(C₁-C₄)-perfluoroalkyl,
(m) —SO₂NHCO-heteroaryl, wherein heteroaryl is unsubstituted or substituted as defined in R¹(c), or
(n) —SO₂NHCONR²$^a$R²$^a$; and R¹⁵ is:
(a) H,
(b) aryl, is unsubstituted or substituted with 1 or 2 substituents selected from the group consisting of Cl, Br, I, F, —O—(C₁-C₄)-alkyl, (C₁-C₄)-alkyl, —NO₂, —CF₃, —SO₂NR²R²$^a$, —S—(C₁-C₄)-alkyl, —OH, —NH₂, (C₃-C₇)-cycloalkyl, (C₃-C₁₀)-alkenyl;
(c) (C₁-C₆)-alkyl, (C₂-C₆)-alkenyl or (C₂-C₆)-alkynyl each of which is unsubstituted or substituted with one or more substituents selected from the group consisting of: aryl, (C₃-C₇)-cycloalkyl, Cl, Br, I, F, —OH, —NH₂, —NH[(C₁-C₄)-alkyl], —N[(C₁-C₄)-alkyl]₂, —NH—SO₂R²$^a$, —COOR²$^a$, —SO₂NHR²$^a$; or
(d) an unsubstituted, monosubstituted or disubstituted aromatic 5 or 6 membered ring which contains one or two heteroatoms selected from the group consisting of N, O, S, and wherein the substituents are members selected from the group consisting of —OH, —SH, (C₁-C₄)-alkyl, (C₁-C₄)-alkyloxy —CF₃, Cl, Br, I, F, or NO₂; and R¹⁶ is:
(a) aryl, or
(b) (C₁-C₄)-alkyl which is unsubstituted or substituted with:
  i) NH₂,
  ii) NH[(C₁-C₄)-alkyl],
  iii) N[(C₁-C₄)-alkyl]₂, iv) CO₂H,
v) CO₂(C₁-C₄)-alkyl,
vi) OH,
vii) SO₃H, or
viii) SO₂NH₂; and R¹⁷ is:
(a) H,
(b) (C₁-C₄)-alkyl,
(c) (C₁-C₄)-alkoxyl,
(d) aryl,
(e) aryl-(C₁-C₄)-alkyl,
(f) CO₂R²ᵃ,
(g) CON(R²)₂,
(h) SO₂R²ᵃ,
(i) SO₂N(R²)₂,
(j) P(O)[(C₁-C₄)-alkoxyl]₂, or
(k) imidazol-2-yl or imidazol-4-yl, in which the imidazolyl can be substituted with (C₁-C₄)-alkyl; and R¹⁸ is:
(a) OH,
(b) NR²R¹⁶,
(c) CO₂R²ᵃ,
(d) CON(R²)₂,
(e) S(O)ₙ—(C₁-C₄)-alkyl, or
(f) N[CH₂CH₂]₂Q; and R¹⁹ is:
(a) (C₁-C₄)-alkyl,
(b) CHR²⁰—O—COR²¹,
(c) CH₂CH₂—N[(C₁-C₂)-alkyl]₂,
(d) CH₂CH₂—N[CH₂CH₂]₂O,
(e) (CH₂CH₂O)ᵧ—O—[(C₁-C₄)-alkyl], wherein y is 1 or 2,
(f) aryl or CH₂-aryl, where aryl is as defined above or optionally substituted with CO₂(C₁-C₄)-alkyl,

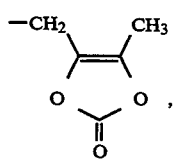

(g)

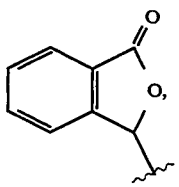

(h)

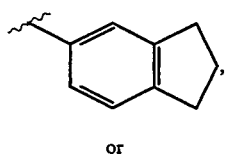

or

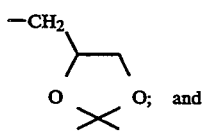

; and

R²⁰ and R²¹ independently are (C₁-C₆)-alkyl or phenyl.

4. The method as recited in claim 1 of structural formula

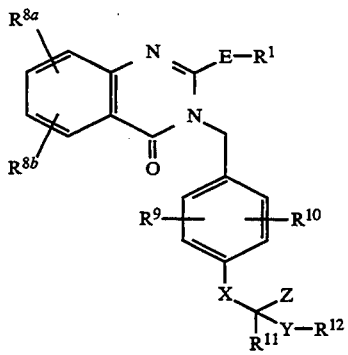

or a pharmaceutically acceptable salt thereof.

5. The method as recited in claim 1 of structural formula

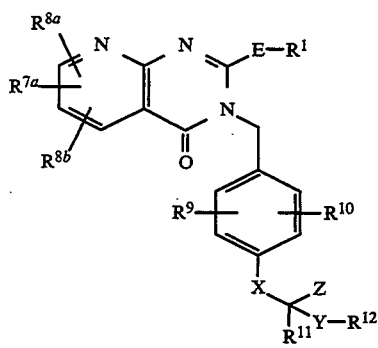

or a pharmaceutically acceptable salt thereof.

6. The method as recited in claim 1 of structural formula

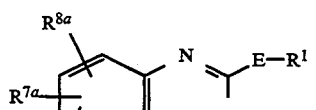

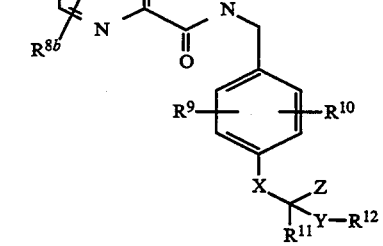

or a pharmaceutically acceptable salt thereof.

7. A method of treating a condition in a mammal, the treatment of which is effected or facilitated by a decrease in endothelin mediated actions, comprising the administration, in an amount that is effective for antagonizing the effect of endothelin, of a compound of structural formula, wherein:

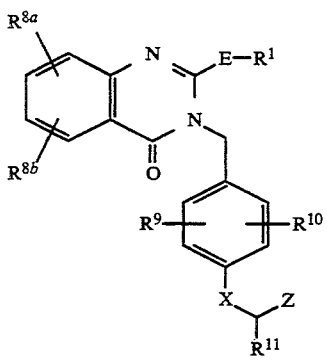

or a pharmaceutically acceptable salt thereof wherein:

$R^1$ is:
(a) $(C_1-C_6)$-alkyl, $(C_2-C_6)$-alkenyl or $(C_2-C_6)$-alkynyl each of which is unsubstituted or substituted with a substituent selected from the group consisting of:
 i) aryl as defined below,
 ii) $(C_3-C_7)$-cycloalkyl,
 iii) Cl, Br, I, F,
 iv) OH,
 v) $NH_2$,
 vi) $NH(C_1-C_4)$-alkyl,
 vii) $N[((C_1-C_4)$-alkyl)]_2$,
 viii) $NHSO_2R^2$,
 ix) $CF_3$,
 x) $COOR^2$, or
 xi) $SO_2NHR^{2a}$; and
(b) aryl, wherein aryl is defined as phenyl or naphthyl unsubstituted or substituted with 1 or 2 substituents selected from the group consisting of:
 i) Br, I, Cl, F,
 ii) $(C_1-C_4)$-alkyl,
 iii) $(C_1-C_4)$-alkoxy,
 iv) $NO_2$,
 v) $CF_3$,
 vi) $SO_2NR^{2a}R^{2a}$,
 vii) $(C_1-C_4)$-alkylthio,
 viii) hydroxy,
 ix) amino,
 x) $(C_3-C_7)$-cycloalkyl,
 xi) $(C_3-C_{10})$-alkenyl; and
(c) heteroaryl, wherein heteroaryl is defined as an unsubstituted, monosubstituted or disubstituted heteroaromatic 5- or 6-membered cyclic moiety, which can contain one or two members selected from the group consisting of N, O, S and wherein the substituents are members selected from the group consisting of:
 i) Cl, Br, I, F,
 ii) OH,
 iii) SH,
 iv) $NO_2$,
 v) $(C_1-C_4)$-alkyl,
 vi) $(C_2-C_4)$-alkenyl,
 vii) $(C_2-C_4)$-alkynyl,
 viii) $(C_1-C_4)$-alkoxy, or
 ix) $CF_3$, or
(d) $(C_1-C_4)$-perfluoroalkyl; and E is:
(a) single bond,
(b) S, or
(c) O; and $R^2$ is:
(a) H, or
(b) $(C_1-C_6)$-alkyl; and $R^{2a}$ is:
(a) $R^2$,
(b) $CH_2$-aryl, or
(c) aryl; and $R^{8a}$ and $R^{8b}$ are independently
(a) H,
(b) aryl-$(C_1-C_4)$-alkyl,
(c) heteroaryl-$(C_1-C_4)$-alkyl,
(d) $(C_1-C_6)$-alkyl, which is unsubstituted or substituted with a substituent selected from the group consisting of: $-CON(R^{2a})_2$, —heteroaryl, $-S(O)_n-R^{16}$, —tetrazol-5-yl, $-CONHSO_2R^{16}$, $-SO_2NH$-heteroaryl, $-SO_2NHCOR^{16}$, $-PO(OR^2)_2$, $-PO(OR^{2a})_2$, $-SO_2NH-CN$, $-NR^2COOR^{16}$, —OH, $-NH_2$, guanidino, $(C_1-C_4)$-alkoxy, $(C_1-C_4)$-alkylthio, $(C_1-C_4)$-alkylamino, $(C_1-C_4)$-dialkylamino, $-COOR^{2a}$, $-CONHR^{2a}$, $-O-COR^{2a}$, or aryl,
(e) —CO-aryl,
(f) $(C_3-C_7)$-cycloalkyl,
(g) Cl, Br, I, F,
(h) —OH,
(i) $-OR^{16}$,
(j) —SH,
(k) $-S(O)_n-(C_1-C_4)$-alkyl,
(l) $-COR^{2a}$,
(m) $-CO_2H$,
(n) $-CO_2-(C_1-C_4)$-alkyl,
(o) $-SO_3H$,
(p) $-NR^2R^{16}$,
(q) $-NR^2COR^{16}$,
(r) $-NR^2COOR^{16}$,
(s) $-SO_2NR^{2a}$,
(t) $-SO_2NR^2R^{2a}$,
(u) $-NO_2$,
(v) $-NHSO_2CF_3$,
(w) $-CONR^{2a}R^{2a}$,
(x) $-(C_1-C_4)$-perfluoroalkyl,
(y) $-COOR^2$,
(z) $-SO_3H$,
(aa) $-N(R^2)SO_2R^{16}$,
(bb) $-NR^2CONR^{2a}R^{16}$,
(cc) $-OC(=O)NR^{16}R^{2a}$,
(dd) —aryl,
(ee) $-NHSO_2CF_3$,
(ff) $-SO_2NH$-heteroaryl,
(gg) $-SO_2NHCOR^{16}$,
(hh) $-CONHSO_2R^{16}$,
(ii) $-PO(OR^2)_2$,
(jj) —tetrazol-5-yl,
(kk) —CONH(tetrazol-5-yl),
(ll) $-SO_2NHCN$, or
(mm) —heteroaryl; and $R^9$ and $R^{10}$ are independently:
(a) H,
(b) $(C_1-C_6)$-alkyl, unsubstituted or substituted with $(C_3-C_7)$cycloalkyl,
(c) $(C_2-C_6)$-alkenyl,
(d) $(C_2-C_6)$-alkynyl,
(e) Cl, Br, F, I,
(f) $(C_1-C_6)$-alkoxy,
(g) when $R^9$ and $R^{10}$ are on adjacent carbons, they can be joined to form a phenyl ring,
(h) $(C_1-C_6)$-perfluoroalkyl, (i) (C$_3$-C$_7$)-cycloalkyl, unsubstituted or substituted with
(j) aryl,
(k) (C$_1$-C$_6$)-alkyl—S(O)$_n$—(CH$_2$)$_n$—,
(l) hydroxy-(C$_1$-C$_6$)-alkyl,
(m) —CF$_3$,
(n) —CO$_2$R$^{2a}$,
(o) —OH,
(p) —NR$^2$R$^{16}$,
(q) —[(C$_1$-C$_6$)-alkyl]NR$^2$R$^{16}$,
(r) —NO$_2$,
(s) —(CH$_2$)$_n$—SO$_2$—N(R$^2$)$_2$,
(t) —NR$^2$CO—(C$_1$-C$_4$)-alkyl, or
(u) —CON(R$^2$)$_2$; and X is:
(a) —O—,
(b) —S(O)$_n$—,
(c) —NR$^{13}$—,
(d) —CH$_2$O—,
(e) —CH$_2$S(O)$_n$,
(f) —CH$_2$NR$^{13}$—,
(g) —OCH$_2$—,
(h) —NR$^{13}$CH$_2$—,
(i) —S(O)$_n$CH$_2$—,
(j) single bond; and R$^{11}$ is:
(a) H,
(b) (C$_1$-C$_6$)-alkyl, unsubstituted or substituted with a substituent selected from the group consisting of:
  (i) aryl,
  (ii) (C$_3$-C$_7$)-cycloalkyl,
  (iii) NR$^2$R$^{16}$,
  (iv) morpholin-4-yl,
  (v) OH,
  (vi) CO$_2$R$^{2a}$, or
  (vii) CON(R$^2$)$_2$,
(c) aryl or aryl-(C$_1$-C$_2$)-alkyl, unsubstituted or substituted with 1 to 3 substitutents selected from the group consisting of:
  (i) Cl, Br, I, F,
  (ii) (C$_1$-C$_6$)-alkyl,
  (iii) [(C$_1$-C$_5$)-alkenyl]CH$_2$—,
  (iv) [(C$_1$-C$_5$)-alkynyl]CH$_2$—,
  (v) (C$_1$-C$_6$)-alkyl—S(O)$_n$—(CH$_2$)$_n$—,
  (vi) —CF$_3$,
  (vii) —CO$_2$R$^{2a}$,
  (viii) —OH,
  (ix) —NR$^2$R$^{16}$,
  (x) —NO$_2$,
  (xi) —NR$^2$COR$^2$,
  (xii) —CON(R$^2$)$_2$,
  (xiii) —G—[(C$_1$-C$_6$)-alkyl]-R$^{18}$,
  (xiv) —N[CH$_2$CH$_2$]$_2$Q, or
  (xv) —P(O)[O-(C$_1$-C$_4$)-alkyl]$_2$,
  and can additionally be substituted with 1 or 2 substituents selected from the group consisting of: Br, Cl or F,
(d) (C$_3$-C$_7$)-cycloalkyl, or
(e) when Y is single bond, R$^{11}$ and R$^{12}$ can be joined to form a ring of 5 to 7 carbon atoms, the ring can be benzo-fused and one carbon of which can be replaced with a heteroatom selected from the group consisting of: O, S(O)$_n$ and NR$^{17}$; and G is: a single bond, O, S(O)$_n$ or NR$^{18}$; and
Q is: O, S(O)$_n$ or NR$^{17}$; and
R$^{13}$ is:
(a) H,
(b) (C$_1$-C$_6$)-alkyl,
(c) aryl,
(d) aryl-(C$_1$-C$_6$)-alkyl-(C=O)—,
(e) (C$_1$-C$_6$)-alkyl-(C=O)—,
(f) [(C$_2$-C$_5$)-alkenyl]CH$_2$—,
(g) [(C$_2$-C$_5$)-alkynyl]CH$_2$—, or
(h) aryl-CH$_2$—; and Z is:
(a) —CO$_2$H,
(b) —CO$_2$R$^{19}$,
(c) —tetrazol-5-yl,
(d) —CONH(tetrazol-5-yl),
(e) —CONHSO$_2$-aryl,
(f) —CONHSO$_2$—(C$_1$-C$_8$)-alkyl, wherein the alkyl group is unsubstituted or substituted with a substituent selected from the group consisting of: —OH, —SH, —O(C$_1$-C$_4$)-alkyl, —S—(C$_1$-C$_4$)-alkyl, —CF$_3$, Cl, Br, F, I, —NO$_2$, —CO$_2$H, —CO$_2$—(C$_1$-C$_4$)-alkyl, —NH$_2$, —NH[(C$_1$-C$_4$)-alkyl], —N[(C$_1$-C$_4$)-alkyl]$_2$; and
(g) —CONHSO$_2$—(C$_1$-C$_4$)-perfluoroalkyl,
(h) —CONHSO$_2$-heteroaryl,
(i) —CONHSO$_2$NR$^{2a}$R$^{2a}$; and
(j) —SO$_2$NHCO-aryl,
(k) —SO$_2$NHCO-(C$_1$-C$_8$)-alkyl, wherein the alkyl group is unsubstituted or substituted with a substituent selected from the group consisting of: —OH, —SH, —O(C$_1$-C$_4$)-alkyl, —S—(C$_1$-C$_4$)-alkyl, —CF$_3$, Cl, Br, F, I, —NO$_2$, —CO$_2$H, —CO$_2$—(C$_1$-C$_4$)-alkyl, —NH$_2$, —NH[(C$_1$-C$_4$)-alkyl], —N[(C$_1$-C$_4$)-alkyl]$_2$; and
(l) —SO$_2$NHCO—(C$_1$-C$_4$)-perfluoroalkyl,
(m) —SO$_2$NHCO-heteroaryl,
(n) —SO$_2$NHCONR$^{2a}$R$^{2a}$;
(o) —PO(OH)$_2$,
(p) —PO(OR$^2$)$_2$, or
(q) —PO(OH)(OR$^2$); and R$^{16}$ is:
(a) H, or
(b) (C$_1$-C$_4$)-alkyl, is unsubstituted or substituted with:
  i) NH$_2$,
  ii) NH[(C$_1$-C$_4$)-alkyl],
  iii) N[(C$_1$-C$_4$)-alkyl]$_2$,
  iv) CO$_2$H,
  v) CO$_2$(C$_1$-C$_4$)-alkyl,
  vi) OH,
  vii) SO$_3$H, or
  viii) SO$_2$NH$_2$; and R$^{17}$ is:
(a) H,
(b) (C$_1$-C$_4$)-alkyl,
(c) (C$_1$-C$_4$)-alkoxyl,
(d) aryl,
(e) aryl-(C$_1$-C$_4$)-alkyl,
(f) CO$_2$R$^{2a}$,
(g) CON(R$^2$)$_2$,
(h) SO$_2$R$^{2a}$,
(i) SO$_2$N(R$^2$)$_2$,
(j) P(O)[(C$_1$-C$_4$)-alkoxyl]$_2$, or
(k) imidazol-2-yl or imidazol-4-yl, in which the imidazolyl can be substituted with (C$_1$-C$_4$)-alkyl; and R$^{17}$ is:
(a) OH,
(b) NR$^2$R$^{16}$,
(c) CO$_2$R$^{2a}$,
(d) CON(R$^2$)$_2$, (e) $S(O)_n$—$(C_1-C_4)$-alkyl, or
(f) $N(CH_2CH_2)_2Q$; and $R^{19}$ is:
(a) $(C_1-C_4)$-alkyl,
(b) $CHR^{20}$—O—$COR^{21}$,
(c) $CH_2CH_2$—$N[(C_1-C_2)$-alkyl$]_2$,
(d) $CH_2CH_2$—$N[CH_2CH_2]_2O$,
(e) $(CH_2CH_2O)_y$—O—$[(C_1-C_4)$-alkyl], wherein y is 1 or 2,
(f) aryl or $CH_2$-aryl, where aryl is as defined above or optionally substituted with $CO_2$—$(C_1-C_4)$-alkyl, (g) [structure]

(h) [structure]

(i) [structure]

or

[structure]

$R^{20}$ and $R^{21}$ independently are $(C_1-C_6)$-alkyl or phenyl.

8. A method of treating a condition in a mammal, the treatment of which is effected or facilitated by a decrease in endothelin mediated actions, comprising the administration, in an amount that is effective for antagonizing the effect of endothelin, of a compound of structural formula, wherein:

[structure I]

or a pharmaceutically acceptable salt thereof wherein:

$R^1$ is:
(a) $(C_1-C_6)$-alkyl, $(C_2-C_6)$-alkenyl or $(C_2-C_6)$-alkynyl each of which is unsubstituted or substituted with a substituent selected from the group consisting of:
  i) aryl as defined below,
  ii) $(C_3-C_7)$-cycloalkyl,
  iii) Cl, Br, I, F,
  iv) OH,
  v) $NH_2$,
  vi) $NH(C_1-C_4)$-alkyl,
  vii) $N[((C_1-C_4)$-alkyl$)]_2$,
  viii) $NHSO_2R^2$,
  ix) $CF_3$,
  x) $COOR^2$, or
  xi) $SO_2NHR^{2a}$; and
(b) aryl, wherein aryl is defined as phenyl or naphthyl unsubstituted or substituted with 1 or 2 substituents selected from the group consisting of:
  i) Br, I, Cl, F,
  ii) $(C_1-C_4)$-alkyl,
  iii) $(C_1-C_4)$-alkoxy,
  iv) $NO_2$,
  v) $CF_3$,
  vi) $SO_2NR^{2a}R^{2a}$,
  vii) $(C_1-C_4)$-alkylthio,
  viii) hydroxy,
  ix) amino,
  x) $(C_3-C_7)$-cycloalkyl,
  xi) $(C_3-C_{10})$-alkenyl, or
(c) $(C_1-C_4)$-perfluoroalkyl; and
n is 0 to 2; and $R^2$ is:
(a) H, or
(b) $(C_1-C_6)$-alkyl; and $R^{2a}$ is:
(a) $R^2$,
(b) $CH_2$-aryl, or
(c) aryl; and $R^{8b}$ is:
(a) H,
(d) $(C_1-C_6)$-alkyl, which is unsubstituted or substituted with a substituent selected from the group consisting of: —$CON(R^{2a})_2$, —heteroaryl, —$S(O)_n$—$R^{16}$, —tetrazol-5-yl, —$CONHSO_2R^{16}$, —$SO_2NH$—heteroaryl, —$SO_2NHCOR^{16}$, —$PO(OR^2)_2$, —$PO(OR^{2a})_2$, —$SO_2NH$—CN, —$NR^2COOR^{16}$, —OH, —$NH_2$, guanidino, $(C_1-C_4)$-alkoxy, $(C_1-C_4)$-alkylthio, $(C_1-C_4)$-alkylamino, $(C_1-C_4)$-dialkylamino, —$COOR^{2a}$, —$CONHR^{2a}$, —O—$COR^{2a}$, or aryl,
(g) Cl, Br, I, F,
(h) —$OR^{16}$,
(i) —$S(O)_n$—$(C_1-C_4)$-alkyl,
(j) —$COR^{2a}$,
(k) —$NR^2R^{16}$,
(l) —$NR^2COR^{16}$,
(m) —$NR^2COOR^{16}$,
(n) —$NO_2$,
(o) —$COOR^2$, or
(p) —$NR^2CONR^{2a}R^{16}$; and $R^9$ and $R^{10}$ are independently:
(a) H,
(b) $(C_1-C_6)$-alkyl, unsubstituted or substituted with $(C_3-C_7)$-cycloalkyl,
(c) $(C_2-C_6)$-alkenyl,
(d) $(C_2-C_6)$-alkynyl,
(e) Cl, Br, F, I,
(f) $(C_1-C_6)$-alkoxy,
(i) $(C_3-C_7)$-cycloalkyl, unsubstituted or substituted with $(C_1-C_6)$-alkyl, X is:
  (a) —O—,
  (b) —S(O)$_n$—, or
  (c) —NR$^{13}$—; and R$^{11}$:
  (a) H,
  (b) (C$_1$–C$_6$)-alkyl, unsubstituted or substituted with a substituent selected from the group consisting of:
    (i) aryl,
    (ii) (C$_3$–C$_7$)-cycloalkyl,
    (iii) NR$^2$R$^{21}$,
    (iv) morpholin-4-yl,
    (v) OH,
    (vi) CO$_2$R$^{2a}$, or
    (vii) CON(R$^2$)$_2$,
  (c) phenyl or phenyl-(C$_1$–C$_2$)-alkyl, unsubstituted or substituted with 1 to 3 substituents selected from the group consisting of:
    (i) Cl, Br, I, F,
    (ii) (C$_1$–C$_6$)-alkyl,
    (iii) [(C$_1$–C$_5$)-alkenyl]CH$_2$—,
    (iv) [(C$_1$–C$_5$)-alkynyl]CH$_2$—,
    (v) (C$_1$–C$_6$)-alkyl—S(O)$_n$—(CH$_2$)$_n$—,
    (vi) —CF$_3$,
    (vii) —CO$_2$R$^{2a}$,
    (viii) —OH,
    (ix) —NR$^2$R$^{16}$,
    (x) —NO$_2$,
    (xi) —NR$^2$COR$^2$,
    (xii) —CON(R$^2$)2,
    (xiii) —G—[(C$_1$–C$_6$)-alkyl]-R$^{18}$,
    (xiv) —N[CH$_2$CH$_2$]$_2$Q, or
    (xv) —P(O)[O—(C$_1$–C$_4$)-alkyl]$_2$, or and can additionally be substituted with 1 or 2 substituents selected from the group consisting of: Br, Cl or F,
  (d) (C$_3$–C$_7$)-cycloalkyl; and G is: a single bond, O, S(O)$_n$ or NR$^{18}$; and
Q is: O, S(O)$_n$ or NR$^{17}$; and R$^{13}$ is:
  (a) H,
  (b) (C$_1$–C$_6$)-alkyl,
  (c) phenyl or naphthyl,
  (d) phenyl-(C$_1$–C$_6$)-alkyl-(C=O)—,
  (e) (C$_1$–C$_6$)-alkyl-(C=O)—,
  (f) [(C$_2$–C$_5$)-alkenyl]CH$_2$—,
  (g) [(C$_2$–C$_5$)-alkynyl]CH$_2$—, or
  (h) phenyl—CH$_2$—; and Z is:
  (a) —CO$_2$H,
  (b) —CO$_2$R$^{19}$,
  (c) —tetrazol-5-yl,
  (d) —CONH(tetrazol-5-yl),
  (e) —CONHSO$_2$-aryl,
  (f) —CONHSO$_2$—heteroaryl, heteroaryl is defined as an unsubstituted, monosubstituted or disubstituted heteroaromatic 5- or 6-membered cyclic moiety, which can contain one or two members selected from the group consisting of N, O, S and wherein the substituents are members selected from the group consisting of:
    i) Cl, Br, F, I,
    ii) OH,
    iii) SH,
    iv) NO$_2$,
    v) (C$_1$–C$_4$)-alkyl,
    vi) (C$_2$–C$_4$)-alkenyl,
    vii) (C$_2$–C$_4$)-alkynyl,
    viii) (C$_1$–C$_4$)-alkoxy, or
    ix) CF$_3$,
  (g) —CONHSO$_2$—(C$_1$–C$_8$)-alkyl, wherein the alkyl group is unsubstituted or substituted with a substituent selected from the group consisting of: —OH, —SH, —O—(C$_1$–C$_4$)-alkyl, —S—(C$_1$–C$_4$)-alkyl, —CF$_3$, Cl, Br, F, I, —NO$_2$, —CO$_2$H, —CO$_2$—(C$_1$–C$_4$)-alkyl, —NH$_2$, —NH[(C$_1$–C$_4$)-alkyl] or —N[(C$_1$–C$_4$)-alkyl]$_2$, or
  (h) CONHSO$_2$—(C$_1$–C$_4$)-perfluoroalkyl, or
  (i) CONHSO$_2$NR$^{2a}$R$^{2a}$; and R$^{16}$ is:
  (a) H, or
  (b) (C$_1$–C$_4$)-alkyl, is unsubstituted or substituted with:
    i) NH$_2$,
    ii) NH[(C$_1$–C$_4$)-alkyl],
    iii) N[(C$_1$–C$_4$)-alkyl]$_2$,
    iv) CO$_2$H,
    v) CO$_2$(C$_1$–C$_4$)-alkyl,
    vi) OH,
    vii) SO$_3$H, or
    viii) SO$_2$NH$_2$; and R$^{17}$ is:
  (a) H,
  (b) (C$_1$–C$_4$)-alkyl,
  (c) (C$_1$–C$_4$)-alkoxyl,
  (d) aryl,
  (e) aryl-(C$_1$–C$_4$)-alkyl,
  (f) CO$_2$R$^{2a}$,
  (g) CON(R$^2$)$_2$,
  (h) SO$_2$R$^{2a}$,
  (i) SO$_2$N(R$^2$)$_2$,
  (j) P(O)[(C$_1$–C$_4$)-alkoxyl]$_2$, or
  (k) imidazol-2-yl or imidazol-4-yl, in which the imidazolyl can be substituted with (C$_1$–C$_4$)-alkyl; and R$^{18}$ is:
  (a) OH,
  (b) NR$^2$R$^{16}$,
  (c) CO$_2$R$^{2a}$,
  (d) CON(R$^2$)$_2$,
  (e) S(O)$_n$—(C$_1$–C$_4$)-alkyl, or
  (f) N(CH$_2$CH$_2$)$_2$Q; and R$^{19}$ is:
  (a) (C$_1$–C$_4$)-alkyl,
  (b) CHR$^{20}$—O—COR$^{21}$,
  (c) CH$_2$CH$_2$—N[(C$_1$–C$_2$)-alkyl]$_2$,
  (d) CH$_2$CH$_2$—N[CH$_2$CH$_2$]$_2$O,
  (e) (CH$_2$CH$_2$O)$_y$—O—[(C$_1$–C$_4$)-alkyl], wherein y is 1 or 2,
  (f) aryl or CH$_2$-aryl, where aryl is as defined above or optionally substituted with CO$_2$-(C$_1$–C$_4$)-alkyl,

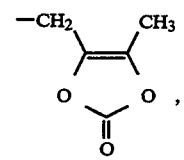 (g)

(h) 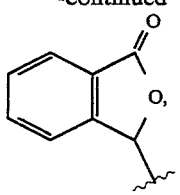

(i) 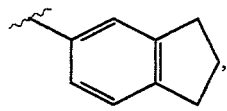 or

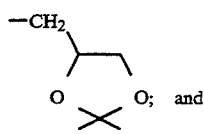

$R^{20}$ and $R^{21}$ independently are $(C_1-C_6)$-alkyl or phenyl.

9. The method as recited in claim 8 in which the structural formula is:

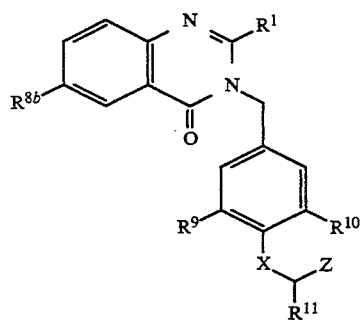    I or a pharmaceutically acceptable salt thereof wherein:

$R^1$ is:
- (a) $(C_1-C_6)$-alkyl, $(C_2-C_6)$-alkenyl or $(C_2-C_6)$-alkynyl each of which is unsubstituted or substituted with a substituent selected from the group consisting of:
  - i) phenyl,
  - ii) $(C_3-C_7)$-cycloalkyl,
  - iii) Cl, Br, I, F,
  - iv) $CF_3$,
- (b) phenyl, unsubstituted or substituted with 1 or 2 substituents selected from the group consisting of:
  - i) Br, I, Cl, F,
  - ii) $(C_1-C_4)$-alkyl,
  - iii) $(C_1-C_4)$-alkoxy,
  - iv) $NO_2$
  - v) $CF_3$
  - vi) $SO_2NR^{2a}R^{2a}$,
  - vii) $(C_1-C_4)$-alkylthio, or
  - viii) $(C_3-C_{10})$-alkenyl, or
- (c) perfluoro-$(C_1-C_4)$-alkyl; and $R^2$ is:
- (a) H, or
- (b) $(C_1-C_6)$-alkyl; and $R^{2a}$ is:
- (a) $R^2$,
- (b) $CH_2$-phenyl, or
- (c) phenyl; and $R^{8b}$ is:
- (a) H,
- (b) $(C_1-C_6)$-alkyl, which is unsubstituted or substituted with a substituent selected from the group consisting of: $-CON(R^{2a})_2$, $-CONHSO_2R^{16}$, $-NR^2COOR^{16}$, $(C_1-C_4)$-alkoxy, $(C_1-C_4)$-alkylthio, $-COOR^{2a}$, $-CONHR^{2a}$
- (c) $-CO$-aryl,
- (d) Cl, Br, I, F,
- (e) $-OR^{21}$,
- (f) $-S(O)_n-(C_1-C_4)$-alkyl,
- (g) $-NR^2R^{16}$,
- (h) $-NR^2COR^{16}$,
- (i) $-NR^2COOR^{16}$,
- (j) $-NO_2$,
- (k) $-NHSO_2CF_3$,
- (l) $-(C_1-C_4)$-perfluoroalkyl,
- (m) $-N(R^2)SO_2R^{16}$,
- (n) $-NR^2CONR^4R^{16}$, n is 0 to 2; and $R^9$ and $R^{10}$ are independently:
- (a) H,
- (b) $(C_1-C_6)$-alkyl, unsubstituted or substituted with $(C_3-C_7)$-cycloalkyl,
- (c) $(C_2-C_6)$-alkenyl,
- (d) $(C_2-C_6)$-alkynyl,
- (e) Cl, Br, F, I,
- (f) $(C_1-C_6)$-alkoxy,
- (g) $(C_1-C_6)$-perfluoroalkyl,
- (h) $(C_3-C_7)$-cycloalkyl, unsubstituted or substituted with $(C_1-C_6)$-alkyl, X is:
- (a) $-O-$,
- (b) $-S(O)_n-$, or
- (c) $-NR^{13}-$; and $R^{11}$ is:
- (a) H,
- (b) phenyl, unsubstituted or substituted with 1 to 5 substitutents selected from the group consisting of:
  - i) Cl, Br, I, F,
  - ii) $(C_1-C_6)$-alkyl,
  - iii) $[(C_1-C_5)$-alkenyl$]CH_2-$,
  - iv) $[(C_1-C_5)$-alkynyl$]CH_2-$,
  - v) $(C_1-C_6)$-alkoxy,
  - vi) $(C_1-C_6)$-alkyl-$S(O)_n-(CH_2)_n-$,
  - vii) hydroxy-$(C_1-C_6)$-alkyl,
  - viii) $-CF_3$,
  - ix) $-CO_2R^{2a}$,
  - x) $-OH$,
  - xi) $-NR^2R^{16}$,
  - xii) $-[(C_1-C_6)$-alkyl$]NR^2R^{16}$,
  - xiii) $-NO_2$,
  - xiv) $-(CH_2)_n-SO_2-N(R^2)_2$,
  - xv) $-NR^2CO-(C_1-C_4)$-alkyl, or
  - xvi) $-CON(R^2)_2$;
- (c) phenyl-$(C_1-C_2)$-alkyl, unsubstituted or substituted with 1 to 5 substituents selected from the group consisting of:
  - i) Cl, Br, I, F,
  - ii) $(C_1-C_6)$-alkyl,
  - iii) $[(C_1-C_5)$-alkenyl$]CH_2-$,
  - iv) $[(C_1-C_5)$-alkynyl$]CH_2-$,
  - v) $(C_1-C_4)$-alkoxy,
  - vi) $(C_1-C_4)$-alkylthio,
  - vii) hydroxy-$(C_1-C_6)$-alkyl, viii) —$CF_3$,
ix) —$CO_2R^{2a}$,
x) —OH,
xi) —$NR^2R^{16}$,
xii) —[($C_1$-$C_6$)-alkyl]$NR^2R^{16}$,
xiii) —$NO_2$,
xiv) —$(CH_2)_n$—$SO_2$—$N(R^2)_2$,
xv) —$NR^2CO$—($C_1$-$C_4$)-alkyl, or
xvi) —$CON(R^2)_2$,
(d) ($C_3$-$C_7$)-cycloalkyl; and Z is:
(a) —$CO_2H$,
(b) —$CO_2$—($C_1$-$C_6$)-alkyl,
(c) —tetrazol-5-yl,
(d) —CONH(tetrazol-5-yl),
(e) —$CONHSO_2$-phenyl,
(f) —$CONHSO_2$—($C_1$-$C_8$)-alkyl, wherein the alkyl group is unsubstituted or substituted with a substituent selected from the group consisting of: —OH, —SH, —O-($C_1$-$C_4$)-alkyl, —S—($C_1$-$C_4$)-alkyl, —$CF_3$, Cl, Br, F, I, —$NO_2$, —$CO_2H$, —$CO_2$-($C_1$-$C_4$)-alkyl, —$NH_2$, —NH[($C_1$-$C_4$)-alkyl], —N[($C_1$-$C_4$)-alkyl]$_2$,
(g) —$CONHSO_2$-($C_1$-$C_4$)-perfluoroalkyl,
(h) —$CONHSO_2$-heteroaryl, heteroaryl is defined as an unsubstituted, monosubstituted or disubstituted heteroaromatic 5- or 6-membered cyclic moiety, which can contain one or two members selected from the group consisting of N, O, S and wherein the substituents are members selected from the group consisting of:
i) Cl, Br, F, I,
ii) OH,
iii) SH,
iv) $NO_2$,
v) ($C_1$-$C_4$)-alkyl,
vi) ($C_2$-$C_4$)-alkenyl,
vii) ($C_2$-$C_4$)-alkynyl,
viii) ($C_1$-$C_4$)-alkoxy, or
ix) $CF_3$, or
i) —$CONHSO_2NR^{2a}R^{2a}$; and $R^{16}$ is:
(a) H, or
(b) ($C_1$-$C_4$)-alkyl.

10. The method as recited in claim 1, wherein the condition is selected from the group consisting of: hypertension, pulmonary hypertension, Raynaud's disease, myocardial infarction, angina pectoris, acute renal failure, cerebral infarction, cerebral vasospasm, arteriosclerosis, vascular restenosis, asthma, endotoxic shock, endotoxin-induced multiple organ failure or disseminated intravascular coagulation, or cyclosporin-induced renal failure or hypertension.

11. The method as recited in claim 10, wherein the condition is hypertension.

12. The method as recited in claim 11, wherein the mammal is human.

13. A method of treating cardiovascular disorders by administering to a person in need of such treatment a therapeutically effective amount of a compound of Formula I as recited in claim 1.

14. The method as recited in claim 1 comprising a pharmaceutical composition of therapeutically effective amount of the compound of formula I and a pharmaceutically acceptable carrier.

* * * * *